United States Patent
Alexander et al.

(10) Patent No.: US 12,351,977 B2
(45) Date of Patent: Jul. 8, 2025

(54) ACTIVELY HEATED OR COOLED GARMENTS OR FOOTWEAR

(71) Applicant: Ember Technologies, Inc., Westlake Village, CA (US)

(72) Inventors: Clayton Alexander, Westlake Village, CA (US); Daren John Leith, Agoura Hills, CA (US); Holland Young Alexander, Westlake Village, CA (US); Rahul Mulinti, Westlake Village, CA (US); Christopher Thomas Wakeham, Solana Beach, CA (US); Mikko Juhani Timperi, San Marcos, CA (US); Jacob William Emmert, Westchester, CA (US)

(73) Assignee: Ember Technologies, Inc., Westlake Village, CA (US)

( * ) Notice: Subject to any disclaimer, the term of this patent is extended or adjusted under 35 U.S.C. 154(b) by 831 days.

(21) Appl. No.: 17/593,126

(22) PCT Filed: Mar. 12, 2020

(86) PCT No.: PCT/US2020/022441
§ 371 (c)(1),
(2) Date: Sep. 9, 2021

(87) PCT Pub. No.: WO2020/190651
PCT Pub. Date: Sep. 24, 2020

(65) Prior Publication Data
US 2022/0154389 A1      May 19, 2022

Related U.S. Application Data

(60) Provisional application No. 62/819,230, filed on Mar. 15, 2019.

(51) Int. Cl.
*D06F 59/02*   (2006.01)
*A41D 1/00*   (2018.01)
(Continued)

(52) U.S. Cl.
CPC ............. *D06F 59/02* (2013.01); *A41D 1/002* (2013.01); *A41D 13/005* (2013.01); *A47G 25/20* (2013.01)

(58) Field of Classification Search
CPC .. A41D 1/002; A41D 13/005; A47G 25/0671; A47G 25/0692; A47G 25/14;
(Continued)

(56) References Cited

U.S. PATENT DOCUMENTS

| | | |
|---|---|---|
| 1,284,378 A | 11/1918 | Lemercier |
| 1,328,229 A | 1/1920 | Hewitt |

(Continued)

FOREIGN PATENT DOCUMENTS

| | | |
|---|---|---|
| AU | 2007100666 A4 | 9/2007 |
| BR | PI0803168 A2 | 3/2011 |

(Continued)

OTHER PUBLICATIONS

Office Action received in Chinese Patent Application No. 202080031974.X, dated Sep. 19, 2023, in 31 pages.
(Continued)

*Primary Examiner* — Chris Q Liu
*Assistant Examiner* — James F Sims, III
(74) *Attorney, Agent, or Firm* — Knobbe, Martens, Olson & Bear LLP

(57) ABSTRACT

Garments or footwear with active temperature control include one or more heating or cooling elements, one or more batteries, and one or more power receivers. Circuitry of the garment of footwear is configured to control the delivery of power to the one or more heating or cooling
(Continued)

elements to heat or cool one or more portions of the garment associated with the one or more heating or cooling elements.

21 Claims, 24 Drawing Sheets

(51) Int. Cl.
    *A41D 13/005*     (2006.01)
    *A47G 25/20*     (2006.01)

(58) Field of Classification Search
    CPC .. A47G 25/20; A61B 5/02055; A61B 5/6804; D06F 59/02; H02J 13/00022; H02J 2310/23; H02J 7/0063; Y02B 90/20; Y04S 40/126
    USPC .................................................. 219/211, 520
    See application file for complete search history.

(56) References Cited

U.S. PATENT DOCUMENTS

| | | | |
|---|---|---|---|
| 1,691,472 | A | 11/1928 | Graham et al. |
| 1,761,829 | A | 6/1930 | Heinemann |
| 2,277,772 | A | 3/1942 | Marick |
| 2,329,766 | A | 9/1943 | Jacobsen |
| 2,342,744 | A | 2/1944 | Mccready |
| 2,460,433 | A | 2/1949 | Ripley |
| 2,579,383 | A | 12/1951 | Goudsmit |
| 3,000,190 | A | 9/1961 | Stark |
| 3,084,241 | A | 4/1963 | Carrona |
| 3,293,405 | A | 12/1966 | Costanzo |
| 3,392,264 | A | 7/1968 | Stanley |
| 3,501,616 | A | 3/1970 | Stanley |
| 3,507,321 | A | 4/1970 | Palma |
| 3,513,297 | A | 5/1970 | Jordan |
| 3,513,824 | A | 5/1970 | Fitzgerald et al. |
| 3,519,791 | A | 7/1970 | Basseches et al. |
| 3,569,666 | A | 3/1971 | Murphy et al. |
| 3,644,705 | A | 2/1972 | Johnson |
| 3,663,796 | A | 5/1972 | Hines et al. |
| 3,663,797 | A | 5/1972 | Marsh |
| 3,729,613 | A | 4/1973 | Deloire et al. |
| 3,745,301 | A | 7/1973 | Sherrill et al. |
| 3,751,620 | A | 8/1973 | Yuasa |
| 3,778,590 | A | 12/1973 | Iizuka et al. |
| 3,781,514 | A | 12/1973 | Olson et al. |
| 3,858,028 | A | 12/1974 | Kerr |
| 3,946,193 | A | 3/1976 | Giese |
| 3,978,183 | A | 8/1976 | Erickson |
| 3,989,924 | A | 11/1976 | Kurtzer |
| 3,999,037 | A | 12/1976 | Metcalf, Sr. |
| 4,021,640 | A | 5/1977 | Gross et al. |
| 4,061,898 | A | 12/1977 | Murray et al. |
| 4,087,675 | A | 5/1978 | Sansonetti |
| 4,273,989 | A | 6/1981 | Hinton et al. |
| 4,404,460 | A | 9/1983 | Kerr |
| 4,533,418 | A | 8/1985 | Appling |
| 4,551,857 | A | 11/1985 | Galvin |
| 4,713,531 | A | 12/1987 | Fennekels et al. |
| 4,764,665 | A | 8/1988 | Orban |
| 4,777,344 | A | 10/1988 | Nash et al. |
| 4,825,039 | A | 4/1989 | Yoo |
| 4,948,951 | A | 8/1990 | Balzano |
| 4,950,868 | A | 8/1990 | Moss et al. |
| 5,032,705 | A | 7/1991 | Batcheller et al. |
| 5,075,983 | A | 12/1991 | Mabboux et al. |
| 5,105,067 | A | 4/1992 | Brekkestran et al. |
| 5,148,002 | A | 9/1992 | Kuo et al. |
| 5,302,807 | A | 4/1994 | Zhao |
| 5,422,462 | A | 6/1995 | Kishimoto |
| 5,541,388 | A | 7/1996 | Gadd |
| 5,620,621 | A | 4/1997 | Sontag |
| 5,777,296 | A | 7/1998 | Bell |
| 5,800,490 | A | 9/1998 | Patz et al. |
| 5,893,991 | A | 4/1999 | Newell |
| 5,906,004 | A | 5/1999 | Lebby et al. |
| 5,977,517 | A | 11/1999 | Grosjean |
| 6,005,222 | A | 12/1999 | Hicks |
| 6,041,518 | A | 3/2000 | Polycarpe |
| 6,049,062 | A | 4/2000 | Jones |
| 6,060,693 | A | 5/2000 | Brown |
| 6,172,344 | B1 * | 1/2001 | Gordon .................... H05B 3/36 219/545 |
| 6,218,644 | B1 | 4/2001 | Zorn et al. |
| 6,239,410 | B1 | 5/2001 | Tackore |
| 6,331,695 | B1 | 12/2001 | West |
| 6,501,055 | B2 | 12/2002 | Rock et al. |
| 6,550,471 | B2 | 4/2003 | Szymocha et al. |
| 6,649,873 | B1 | 11/2003 | Cintron, Jr. et al. |
| 6,760,925 | B1 | 7/2004 | Maxwell |
| 6,941,775 | B2 | 9/2005 | Sharma |
| 6,963,055 | B2 | 11/2005 | Rock et al. |
| 7,120,938 | B2 | 10/2006 | Ichigaya |
| 7,230,206 | B1 | 6/2007 | Randall |
| 7,560,664 | B2 | 7/2009 | Ford et al. |
| 7,816,628 | B2 | 10/2010 | Fernandez et al. |
| 7,891,019 | B2 | 2/2011 | Goldfine |
| 7,935,911 | B2 | 5/2011 | Kaesler |
| 8,052,630 | B2 | 11/2011 | Kloecker et al. |
| 8,097,832 | B2 | 1/2012 | Huang et al. |
| 8,308,489 | B2 | 11/2012 | Lee et al. |
| 8,360,904 | B2 | 1/2013 | Oleson et al. |
| 9,123,216 | B2 | 9/2015 | Chang et al. |
| 9,153,985 | B1 | 10/2015 | Gjøvik et al. |
| 9,339,066 | B2 | 5/2016 | Codner et al. |
| 9,516,907 | B2 | 12/2016 | Guidry |
| 9,564,638 | B2 | 2/2017 | Uemura |
| 9,735,168 | B2 | 8/2017 | Shukuri |
| 9,913,500 | B1 | 3/2018 | Matthews |
| 9,961,723 | B2 | 5/2018 | Chen |
| 9,962,122 | B2 | 5/2018 | Augustine et al. |
| 10,004,283 | B1 | 6/2018 | Baude et al. |
| 10,034,456 | B2 | 7/2018 | Pomponio |
| 10,201,195 | B1 | 2/2019 | Khaliuta et al. |
| 10,212,763 | B2 | 2/2019 | Kurley et al. |
| 10,292,438 | B2 | 5/2019 | Fortenbacher |
| 2004/0087881 | A1 | 5/2004 | Gross |
| 2004/0244090 | A1 | 12/2004 | Langer |
| 2005/0159055 | A1 | 7/2005 | Nakase |
| 2005/0167412 | A1 | 8/2005 | Anson et al. |
| 2006/0191270 | A1 | 8/2006 | Warrer |
| 2006/0213895 | A1 | 9/2006 | Dennis |
| 2007/0045269 | A1 | 3/2007 | Vassallo |
| 2007/0113564 | A1 | 5/2007 | Whitney et al. |
| 2007/0283481 | A1 | 12/2007 | Rawlings |
| 2008/0000890 | A1 | 1/2008 | Chen |
| 2008/0223844 | A1 | 9/2008 | Cronn |
| 2008/0229476 | A1 | 9/2008 | Sanders |
| 2009/0032520 | A1 | 2/2009 | Cronn |
| 2009/0056107 | A1 | 3/2009 | Williams |
| 2009/0057289 | A1 | 3/2009 | Williams |
| 2009/0057290 | A1 | 3/2009 | Williams |
| 2009/0114632 | A1 | 5/2009 | Shiue |
| 2009/0144887 | A1 | 6/2009 | Orandi |
| 2009/0188905 | A1 | 7/2009 | Williams |
| 2009/0264970 | A1 | 10/2009 | Mickel |
| 2009/0282908 | A1 | 11/2009 | Homayoun et al. |
| 2009/0289046 | A1 | 11/2009 | Richmond |
| 2009/0306748 | A1 | 12/2009 | Mollendorf et al. |
| 2010/0107657 | A1 | 5/2010 | Vistakula |
| 2010/0257655 | A1 | 10/2010 | Nilforushan et al. |
| 2011/0047957 | A1 | 3/2011 | Richard |
| 2011/0108538 | A1 | 5/2011 | Gray et al. |
| 2013/0001212 | A1 | 1/2013 | Mangoubi |
| 2013/0037531 | A1 | 2/2013 | Gray et al. |
| 2013/0306614 | A1 | 11/2013 | Fey, Jr. |
| 2014/0158673 | A1 | 6/2014 | Gou |
| 2014/0180624 | A1 | 6/2014 | Nikonov et al. |
| 2014/0246416 | A1 | 9/2014 | White |
| 2014/0318699 | A1 | 10/2014 | Longinotti-Buitoni et al. |
| 2015/0060430 | A1 | 3/2015 | Tsuge et al. |
| 2015/0083705 | A1 | 3/2015 | Cronn et al. |
| 2015/0122791 | A1 | 5/2015 | Hung et al. |

(56) References Cited

U.S. PATENT DOCUMENTS

| | | |
|---|---|---|
| 2015/0136753 A1 | 5/2015 | Cronn et al. |
| 2015/0230524 A1 | 8/2015 | Stevens et al. |
| 2015/0237927 A1 | 8/2015 | Nelson et al. |
| 2015/0272236 A1 | 10/2015 | Chen et al. |
| 2015/0272251 A1 | 10/2015 | Welsh |
| 2015/0312965 A1 | 10/2015 | Chen |
| 2015/0382402 A1 | 12/2015 | Chen |
| 2016/0095369 A1 | 4/2016 | Roberts |
| 2016/0106162 A1 | 4/2016 | Gluckman |
| 2016/0235139 A1 | 8/2016 | Gramlin |
| 2017/0196275 A1 | 7/2017 | Tam et al. |
| 2017/0265533 A1 | 9/2017 | Gueritee et al. |
| 2017/0338533 A1 | 11/2017 | Chungli et al. |
| 2017/0340028 A1 | 11/2017 | Roh |
| 2018/0014585 A1 | 1/2018 | Polonio et al. |
| 2018/0280190 A1 | 10/2018 | Betkowski et al. |
| 2018/0299954 A1 | 10/2018 | Brunnbauer et al. |
| 2019/0029337 A1 | 1/2019 | DeGanello |
| 2019/0142086 A1 | 5/2019 | Dunlop |
| 2019/0191792 A1 | 6/2019 | Hoppel et al. |
| 2020/0383394 A1* | 12/2020 | Bean .................. A41D 13/005 |

FOREIGN PATENT DOCUMENTS

| | | |
|---|---|---|
| BR | 202013030128 U2 | 3/2016 |
| CH | 642265 A5 | 4/1984 |
| CN | 85201360 U | 3/1986 |
| CN | 85203320 U | 4/1986 |
| CN | 85203395 U | 12/1986 |
| CN | 85205170 U | 1/1987 |
| CN | 86203366 U | 1/1987 |
| CN | 86204144 U | 7/1987 |
| CN | 87202600 U | 1/1988 |
| CN | 87209948 U | 6/1988 |
| CN | 87213008 U | 7/1988 |
| CN | 85103443 B | 8/1988 |
| CN | 1034661 A | 8/1989 |
| CN | 2126662 Y | 2/1993 |
| CN | 2128444 Y | 3/1993 |
| CN | 2131317 Y | 5/1993 |
| CN | 2131323 Y | 5/1993 |
| CN | 2138410 Y | 7/1993 |
| CN | 2139779 Y | 8/1993 |
| CN | 2151632 Y | 1/1994 |
| CN | 2155687 Y | 2/1994 |
| CN | 2155688 Y | 2/1994 |
| CN | 2156695 Y | 2/1994 |
| CN | 2169991 Y | 6/1994 |
| CN | 2170649 Y | 7/1994 |
| CN | 2179701 Y | 10/1994 |
| CN | 2188861 Y | 2/1995 |
| CN | 2195207 Y | 4/1995 |
| CN | 2196381 Y | 5/1995 |
| CN | 2206044 Y | 8/1995 |
| CN | 2206748 Y | 9/1995 |
| CN | 2207090 Y | 9/1995 |
| CN | 2209882 Y | 10/1995 |
| CN | 2210842 Y | 10/1995 |
| CN | 2220174 Y | 2/1996 |
| CN | 2223566 Y | 4/1996 |
| CN | 2229147 Y | 6/1996 |
| CN | 2231493 Y | 7/1996 |
| CN | 2238557 Y | 10/1996 |
| CN | 1034661 C | 4/1997 |
| CN | 2253897 Y | 5/1997 |
| CN | 2253916 Y | 5/1997 |
| CN | 2254611 Y | 5/1997 |
| CN | 2256224 Y | 6/1997 |
| CN | 2260430 Y | 8/1997 |
| CN | 2273505 Y | 2/1998 |
| CN | 2274083 Y | 2/1998 |
| CN | 2279042 Y | 4/1998 |
| CN | 2282320 Y | 5/1998 |
| CN | 2283371 Y | 6/1998 |
| CN | 2285069 Y | 7/1998 |
| CN | 2286554 Y | 7/1998 |
| CN | 2311151 Y | 3/1999 |
| CN | 2311156 Y | 3/1999 |
| CN | 2311964 Y | 3/1999 |
| CN | 2314614 Y | 4/1999 |
| CN | 2320057 Y | 5/1999 |
| CN | 2321194 Y | 5/1999 |
| CN | 2323614 Y | 6/1999 |
| CN | 2324743 Y | 6/1999 |
| CN | 2334198 Y | 8/1999 |
| CN | 2340213 Y | 9/1999 |
| CN | 2342621 Y | 10/1999 |
| CN | 2342624 Y | 10/1999 |
| CN | 2343822 Y | 10/1999 |
| CN | 2349817 Y | 11/1999 |
| CN | 2351987 Y | 12/1999 |
| CN | 2357531 Y | 1/2000 |
| CN | 2361111 Y | 2/2000 |
| CN | 2376755 Y | 5/2000 |
| CN | 2377860 Y | 5/2000 |
| CN | 2384449 Y | 6/2000 |
| CN | 2391441 Y | 8/2000 |
| CN | 2391442 Y | 8/2000 |
| CN | 2392390 Y | 8/2000 |
| CN | 2396655 Y | 9/2000 |
| CN | 2397753 Y | 9/2000 |
| CN | 2397756 Y | 9/2000 |
| CN | 2399944 Y | 10/2000 |
| CN | 2404368 Y | 11/2000 |
| CN | 2419846 Y | 2/2001 |
| CN | 2435954 Y | 6/2001 |
| CN | 2439205 Y | 7/2001 |
| CN | 2439790 Y | 7/2001 |
| CN | 2446791 Y | 9/2001 |
| CN | 2448133 Y | 9/2001 |
| CN | 2448134 Y | 9/2001 |
| CN | 2450928 Y | 10/2001 |
| CN | 1322837 A | 11/2001 |
| CN | 2472523 Y | 1/2002 |
| CN | 2478300 Y | 2/2002 |
| CN | 2478385 Y | 2/2002 |
| CN | 2494608 Y | 6/2002 |
| CN | 2496255 Y | 6/2002 |
| CN | 2496266 Y | 6/2002 |
| CN | 2500122 Y | 7/2002 |
| CN | 2506099 Y | 8/2002 |
| CN | 2507274 Y | 8/2002 |
| CN | 2509885 Y | 9/2002 |
| CN | 2509893 Y | 9/2002 |
| CN | 2520693 Y | 11/2002 |
| CN | 2524524 Y | 12/2002 |
| CN | 2524525 Y | 12/2002 |
| CN | 2527118 Y | 12/2002 |
| CN | 2537242 Y | 2/2003 |
| CN | 2544546 Y | 4/2003 |
| CN | 2546310 Y | 4/2003 |
| CN | 2547157 Y | 4/2003 |
| CN | 2547158 Y | 4/2003 |
| CN | 1416754 A | 5/2003 |
| CN | 2567903 Y | 8/2003 |
| CN | 2569580 Y | 9/2003 |
| CN | 2572708 Y | 9/2003 |
| CN | 2572790 Y | 9/2003 |
| CN | 1131660 C | 12/2003 |
| CN | 2595200 Y | 12/2003 |
| CN | 2613159 Y | 4/2004 |
| CN | 2615046 Y | 5/2004 |
| CN | 2618459 Y | 6/2004 |
| CN | 2629477 Y | 8/2004 |
| CN | 2634848 Y | 8/2004 |
| CN | 1164213 C | 9/2004 |
| CN | 2636642 Y | 9/2004 |
| CN | 2636644 Y | 9/2004 |
| CN | 2642068 Y | 9/2004 |
| CN | 2642069 Y | 9/2004 |
| CN | 1170029 C | 10/2004 |
| CN | 2649410 Y | 10/2004 |
| CN | 2652173 Y | 11/2004 |
| CN | 2660929 Y | 12/2004 |

(56) References Cited

FOREIGN PATENT DOCUMENTS

| | | | |
|---|---|---|---|
| CN | 2660930 | Y | 12/2004 |
| CN | 1568846 | A | 1/2005 |
| CN | 2673141 | Y | 1/2005 |
| CN | 2678409 | Y | 2/2005 |
| CN | 2705028 | Y | 6/2005 |
| CN | 2710396 | Y | 7/2005 |
| CN | 2712030 | Y | 7/2005 |
| CN | 2720846 | Y | 8/2005 |
| CN | 2722657 | Y | 9/2005 |
| CN | 2724446 | Y | 9/2005 |
| CN | 2726344 | Y | 9/2005 |
| CN | 1702576 | A | 11/2005 |
| CN | 2741390 | Y | 11/2005 |
| CN | 2747924 | Y | 12/2005 |
| CN | 2750683 | Y | 1/2006 |
| CN | 2750690 | Y | 1/2006 |
| CN | 2751598 | Y | 1/2006 |
| CN | 2758168 | Y | 2/2006 |
| CN | 2759228 | Y | 2/2006 |
| CN | 2764181 | Y | 3/2006 |
| CN | 2764184 | Y | 3/2006 |
| CN | 1761369 | A | 4/2006 |
| CN | 2768499 | Y | 4/2006 |
| CN | 2770402 | Y | 4/2006 |
| CN | 2776083 | Y | 5/2006 |
| CN | 2776088 | Y | 5/2006 |
| CN | 2785951 | Y | 6/2006 |
| CN | 2790203 | Y | 6/2006 |
| CN | 2810233 | Y | 8/2006 |
| CN | 2814867 | Y | 9/2006 |
| CN | 2834219 | Y | 11/2006 |
| CN | 2852743 | Y | 1/2007 |
| CN | 2857512 | Y | 1/2007 |
| CN | 2857516 | Y | 1/2007 |
| CN | 2859980 | Y | 1/2007 |
| CN | 2860986 | Y | 1/2007 |
| CN | 2865329 | Y | 2/2007 |
| CN | 2865334 | Y | 2/2007 |
| CN | 2870507 | Y | 2/2007 |
| CN | 2872890 | Y | 2/2007 |
| CN | 2875114 | Y | 3/2007 |
| CN | 2877350 | Y | 3/2007 |
| CN | 2877353 | Y | 3/2007 |
| CN | 2879695 | Y | 3/2007 |
| CN | 2879696 | Y | 3/2007 |
| CN | 2884770 | Y | 3/2007 |
| CN | 2888920 | Y | 4/2007 |
| CN | 2896921 | Y | 5/2007 |
| CN | 2901916 | Y | 5/2007 |
| CN | 2904694 | Y | 5/2007 |
| CN | 1322837 | C | 6/2007 |
| CN | 2907287 | Y | 6/2007 |
| CN | 1994168 | A | 7/2007 |
| CN | 2917350 | Y | 7/2007 |
| CN | 2922516 | Y | 7/2007 |
| CN | 2925133 | Y | 7/2007 |
| CN | 101001487 | A | 7/2007 |
| CN | 2927728 | Y | 8/2007 |
| CN | 2930351 | Y | 8/2007 |
| CN | 2935862 | Y | 8/2007 |
| CN | 2938678 | Y | 8/2007 |
| CN | 200938859 | Y | 8/2007 |
| CN | 101032350 | A | 9/2007 |
| CN | 200950668 | Y | 9/2007 |
| CN | 200950851 | Y | 9/2007 |
| CN | 200962845 | Y | 10/2007 |
| CN | 200962860 | Y | 10/2007 |
| CN | 200966333 | Y | 10/2007 |
| CN | 200966345 | Y | 10/2007 |
| CN | 200969872 | Y | 11/2007 |
| CN | 200969873 | Y | 11/2007 |
| CN | 200973376 | Y | 11/2007 |
| CN | 200973378 | Y | 11/2007 |
| CN | 200973379 | Y | 11/2007 |
| CN | 200973385 | Y | 11/2007 |
| CN | 200976849 | Y | 11/2007 |
| CN | 200980346 | Y | 11/2007 |
| CN | 200980348 | Y | 11/2007 |
| CN | 101081096 | A | 12/2007 |
| CN | 101091589 | A | 12/2007 |
| CN | 200990871 | Y | 12/2007 |
| CN | 200994426 | Y | 12/2007 |
| CN | 101098572 | A | 1/2008 |
| CN | 201005063 | Y | 1/2008 |
| CN | 201005066 | Y | 1/2008 |
| CN | 201011880 | Y | 1/2008 |
| CN | 201015427 | Y | 2/2008 |
| CN | 201018935 | Y | 2/2008 |
| CN | 101147626 | A | 3/2008 |
| CN | 201029448 | Y | 3/2008 |
| CN | 201029462 | Y | 3/2008 |
| CN | 201036327 | Y | 3/2008 |
| CN | 201039758 | Y | 3/2008 |
| CN | 201045869 | Y | 4/2008 |
| CN | 201051872 | Y | 4/2008 |
| CN | 201051879 | Y | 4/2008 |
| CN | 201054991 | Y | 5/2008 |
| CN | 201054997 | Y | 5/2008 |
| CN | 201062069 | Y | 5/2008 |
| CN | 201073010 | Y | 6/2008 |
| CN | 101209133 | A | 7/2008 |
| CN | 201089493 | Y | 7/2008 |
| CN | 101247679 | A | 8/2008 |
| CN | 201094297 | Y | 8/2008 |
| CN | 201094322 | Y | 8/2008 |
| CN | 201097630 | Y | 8/2008 |
| CN | 201104500 | Y | 8/2008 |
| CN | 101254035 | A | 9/2008 |
| CN | 101268868 | A | 9/2008 |
| CN | 101268869 | A | 9/2008 |
| CN | 201108052 | Y | 9/2008 |
| CN | 201119439 | Y | 9/2008 |
| CN | 201119444 | Y | 9/2008 |
| CN | 101278762 | A | 10/2008 |
| CN | 201131331 | Y | 10/2008 |
| CN | 201139076 | Y | 10/2008 |
| CN | 201142951 | Y | 11/2008 |
| CN | 201146839 | Y | 11/2008 |
| CN | 201146848 | Y | 11/2008 |
| CN | 201146850 | Y | 11/2008 |
| CN | 201146860 | Y | 11/2008 |
| CN | 201160514 | Y | 12/2008 |
| CN | 201164022 | Y | 12/2008 |
| CN | 201165279 | Y | 12/2008 |
| CN | 201167420 | Y | 12/2008 |
| CN | 201171373 | Y | 12/2008 |
| CN | 201171743 | Y | 12/2008 |
| CN | 101336755 | A | 1/2009 |
| CN | 201178707 | Y | 1/2009 |
| CN | 201178729 | Y | 1/2009 |
| CN | 201182219 | Y | 1/2009 |
| CN | 201185668 | Y | 1/2009 |
| CN | 201186980 | Y | 1/2009 |
| CN | 201188890 | Y | 2/2009 |
| CN | 201188891 | Y | 2/2009 |
| CN | 101380145 | A | 3/2009 |
| CN | 201207928 | Y | 3/2009 |
| CN | 201207931 | Y | 3/2009 |
| CN | 201210871 | Y | 3/2009 |
| CN | 201213457 | Y | 4/2009 |
| CN | 201226822 | Y | 4/2009 |
| CN | 101433377 | A | 5/2009 |
| CN | 101433378 | A | 5/2009 |
| CN | 201235883 | Y | 5/2009 |
| CN | 201238629 | Y | 5/2009 |
| CN | 201249842 | Y | 6/2009 |
| CN | 201252836 | Y | 6/2009 |
| CN | 201270778 | Y | 7/2009 |
| CN | 201270820 | Y | 7/2009 |
| CN | 201286367 | Y | 8/2009 |
| CN | 201286375 | Y | 8/2009 |
| CN | 201290353 | Y | 8/2009 |
| CN | 201290364 | Y | 8/2009 |
| CN | 201294644 | Y | 8/2009 |

(56) References Cited

FOREIGN PATENT DOCUMENTS

| | | | |
|---|---|---|---|
| CN | 201299115 Y | 9/2009 |
| CN | 201303612 Y | 9/2009 |
| CN | 201308119 Y | 9/2009 |
| CN | 201312566 Y | 9/2009 |
| CN | 201313602 Y | 9/2009 |
| CN | 201319888 Y | 10/2009 |
| CN | 201319890 Y | 10/2009 |
| CN | 201319896 Y | 10/2009 |
| CN | 201328381 Y | 10/2009 |
| CN | 201329928 Y | 10/2009 |
| CN | 201332701 Y | 10/2009 |
| CN | 201332702 Y | 10/2009 |
| CN | 101584505 A | 11/2009 |
| CN | 101585383 A | 11/2009 |
| CN | 201336968 Y | 11/2009 |
| CN | 201341442 Y | 11/2009 |
| CN | 201341450 Y | 11/2009 |
| CN | 201341451 Y | 11/2009 |
| CN | 201341507 Y | 11/2009 |
| CN | 201345907 Y | 11/2009 |
| CN | 201349556 Y | 11/2009 |
| CN | 201356081 Y | 12/2009 |
| CN | 201356083 Y | 12/2009 |
| CN | 201360579 Y | 12/2009 |
| CN | 201370131 Y | 12/2009 |
| CN | 201388565 Y | 1/2010 |
| CN | 201393308 Y | 1/2010 |
| CN | 201393563 Y | 2/2010 |
| CN | 201393572 Y | 2/2010 |
| CN | 201393573 Y | 2/2010 |
| CN | 201403603 Y | 2/2010 |
| CN | 201409472 Y | 2/2010 |
| CN | 201414446 Y | 3/2010 |
| CN | 201422428 Y | 3/2010 |
| CN | 201426368 Y | 3/2010 |
| CN | 101695408 A | 4/2010 |
| CN | 201440939 U | 4/2010 |
| CN | 201440940 U | 4/2010 |
| CN | 201444951 U | 5/2010 |
| CN | 201451485 U | 5/2010 |
| CN | 201468003 U | 5/2010 |
| CN | 201468004 U | 5/2010 |
| CN | 201468005 U | 5/2010 |
| CN | 201468038 U | 5/2010 |
| CN | 201480015 U | 5/2010 |
| CN | 201480018 U | 5/2010 |
| CN | 201480020 U | 5/2010 |
| CN | 201491294 U | 5/2010 |
| CN | 101731762 A | 6/2010 |
| CN | 101731773 A | 6/2010 |
| CN | 101758912 A | 6/2010 |
| CN | 201491807 U | 6/2010 |
| CN | 201499607 U | 6/2010 |
| CN | 201499655 U | 6/2010 |
| CN | 201504577 U | 6/2010 |
| CN | 201509658 U | 6/2010 |
| CN | 201515697 U | 6/2010 |
| CN | 101766342 A | 7/2010 |
| CN | 101785586 A | 7/2010 |
| CN | 201518789 U | 7/2010 |
| CN | 201525448 U | 7/2010 |
| CN | 201530442 U | 7/2010 |
| CN | 201536655 U | 8/2010 |
| CN | 201541732 U | 8/2010 |
| CN | 201541754 U | 8/2010 |
| CN | 201541758 U | 8/2010 |
| CN | 201557264 U | 8/2010 |
| CN | 201557572 U | 8/2010 |
| CN | 201557594 U | 8/2010 |
| CN | 101828782 A | 9/2010 |
| CN | 201563636 U | 9/2010 |
| CN | 201571532 U | 9/2010 |
| CN | 101292781 B | 10/2010 |
| CN | 201602153 U | 10/2010 |
| CN | 201602158 U | 10/2010 |
| CN | 201602167 U | 10/2010 |
| CN | 101874652 A | 11/2010 |
| CN | 101887927 A | 11/2010 |
| CN | 101889735 A | 11/2010 |
| CN | 201617214 U | 11/2010 |
| CN | 201617217 U | 11/2010 |
| CN | 201630289 U | 11/2010 |
| CN | 201640458 U | 11/2010 |
| CN | 201657786 U | 12/2010 |
| CN | 201657794 U | 12/2010 |
| CN | 201663938 U | 12/2010 |
| CN | 201670308 U | 12/2010 |
| CN | 201675007 U | 12/2010 |
| CN | 201675040 U | 12/2010 |
| CN | 201675054 U | 12/2010 |
| CN | 201675060 U | 12/2010 |
| CN | 201683084 U | 12/2010 |
| CN | 101933684 A | 1/2011 |
| CN | 101959329 A | 1/2011 |
| CN | 201691099 U | 1/2011 |
| CN | 201691135 U | 1/2011 |
| CN | 201691138 U | 1/2011 |
| CN | 201709438 U | 1/2011 |
| CN | 201709454 U | 1/2011 |
| CN | 201709457 U | 1/2011 |
| CN | 201718510 U | 1/2011 |
| CN | 201718511 U | 1/2011 |
| CN | 101966017 A | 2/2011 |
| CN | 101972047 A | 2/2011 |
| CN | 201726884 U | 2/2011 |
| CN | 201733922 U | 2/2011 |
| CN | 201742938 U | 2/2011 |
| CN | 201742967 U | 2/2011 |
| CN | 201742985 U | 2/2011 |
| CN | 201752243 U | 3/2011 |
| CN | 201758793 U | 3/2011 |
| CN | 201767036 U | 3/2011 |
| CN | 201769959 U | 3/2011 |
| CN | 101999765 A | 4/2011 |
| CN | 201782002 U | 4/2011 |
| CN | 201782064 U | 4/2011 |
| CN | 201789971 U | 4/2011 |
| CN | 201798042 U | 4/2011 |
| CN | 201798043 U | 4/2011 |
| CN | 201798060 U | 4/2011 |
| CN | 201805955 U | 4/2011 |
| CN | 201805956 U | 4/2011 |
| CN | 201805979 U | 4/2011 |
| CN | 201 840 251 U | 5/2011 |
| CN | 102038298 A | 5/2011 |
| CN | 102048268 A | 5/2011 |
| CN | 102068064 A | 5/2011 |
| CN | 201813851 U | 5/2011 |
| CN | 201821977 U | 5/2011 |
| CN | 201821981 U | 5/2011 |
| CN | 201830907 U | 5/2011 |
| CN | 102078050 A | 6/2011 |
| CN | 201846792 U | 6/2011 |
| CN | 201846793 U | 6/2011 |
| CN | 201846837 U | 6/2011 |
| CN | 201846840 U | 6/2011 |
| CN | 201846842 U | 6/2011 |
| CN | 201860759 U | 6/2011 |
| CN | 201860764 U | 6/2011 |
| CN | 201860804 U | 6/2011 |
| CN | 201869799 U | 6/2011 |
| CN | 201878803 U | 6/2011 |
| CN | 201878819 U | 6/2011 |
| CN | 201887962 U | 6/2011 |
| CN | 102113711 A | 7/2011 |
| CN | 201898910 U | 7/2011 |
| CN | 201905231 U | 7/2011 |
| CN | 201911346 U | 8/2011 |
| CN | 201919664 U | 8/2011 |
| CN | 201919679 U | 8/2011 |
| CN | 201919700 U | 8/2011 |
| CN | 201929030 U | 8/2011 |
| CN | 201929056 U | 8/2011 |
| CN | 201932289 U | 8/2011 |

(56) References Cited

FOREIGN PATENT DOCUMENTS

| | | |
|---|---|---|
| CN | 201939821 U | 8/2011 |
| CN | 201947984 U | 8/2011 |
| CN | 201947988 U | 8/2011 |
| CN | 201948008 U | 8/2011 |
| CN | 201948013 U | 8/2011 |
| CN | 102188054 A | 9/2011 |
| CN | 102197890 A | 9/2011 |
| CN | 201957813 U | 9/2011 |
| CN | 201957816 U | 9/2011 |
| CN | 201957820 U | 9/2011 |
| CN | 201967720 U | 9/2011 |
| CN | 201967741 U | 9/2011 |
| CN | 201967746 U | 9/2011 |
| CN | 201967750 U | 9/2011 |
| CN | 201976800 U | 9/2011 |
| CN | 201976805 U | 9/2011 |
| CN | 201986740 U | 9/2011 |
| CN | 102217806 A | 10/2011 |
| CN | 102226311 A | 10/2011 |
| CN | 201995603 U | 10/2011 |
| CN | 201996990 U | 10/2011 |
| CN | 202014384 U | 10/2011 |
| CN | 202014614 U | 10/2011 |
| CN | 102240077 A | 11/2011 |
| CN | 202019788 U | 11/2011 |
| CN | 202026832 U | 11/2011 |
| CN | 202035478 U | 11/2011 |
| CN | 202043308 U | 11/2011 |
| CN | 202043633 U | 11/2011 |
| CN | 202050930 U | 11/2011 |
| CN | 202051042 U | 11/2011 |
| CN | 202068984 U | 12/2011 |
| CN | 202069010 U | 12/2011 |
| CN | 202077599 U | 12/2011 |
| CN | 202077617 U | 12/2011 |
| CN | 202085748 U | 12/2011 |
| CN | 202085759 U | 12/2011 |
| CN | 202085770 U | 12/2011 |
| CN | 202085784 U | 12/2011 |
| CN | 202085815 U | 12/2011 |
| CN | 102318914 A | 1/2012 |
| CN | 102318915 A | 1/2012 |
| CN | 202095549 U | 1/2012 |
| CN | 202095593 U | 1/2012 |
| CN | 202104224 U | 1/2012 |
| CN | 202112328 U | 1/2012 |
| CN | 202112366 U | 1/2012 |
| CN | 102362706 A | 2/2012 |
| CN | 101773308 B | 3/2012 |
| CN | 102366171 A | 3/2012 |
| CN | 102370267 A | 3/2012 |
| CN | 102379459 A | 3/2012 |
| CN | 202154073 U | 3/2012 |
| CN | 202154091 U | 3/2012 |
| CN | 202160706 U | 3/2012 |
| CN | 202172891 U | 3/2012 |
| CN | 102396802 A | 4/2012 |
| CN | 102406251 A | 4/2012 |
| CN | 202179144 U | 4/2012 |
| CN | 202179167 U | 4/2012 |
| CN | 202179349 U | 4/2012 |
| CN | 202190779 U | 4/2012 |
| CN | 202197873 U | 4/2012 |
| CN | 202205472 U | 4/2012 |
| CN | 102429387 A | 5/2012 |
| CN | 102462006 A | 5/2012 |
| CN | 102462015 A | 5/2012 |
| CN | 202218625 U | 5/2012 |
| CN | 202222466 U | 5/2012 |
| CN | 202233106 U | 5/2012 |
| CN | 202233107 U | 5/2012 |
| CN | 102485073 A | 6/2012 |
| CN | 102485077 A | 6/2012 |
| CN | 202262455 U | 6/2012 |
| CN | 202262456 U | 6/2012 |
| CN | 202269444 U | 6/2012 |
| CN | 102524985 A | 7/2012 |
| CN | 102524991 A | 7/2012 |
| CN | 102573141 A | 7/2012 |
| CN | 102612179 A | 7/2012 |
| CN | 202286395 U | 7/2012 |
| CN | 202286398 U | 7/2012 |
| CN | 202286430 U | 7/2012 |
| CN | 202286441 U | 7/2012 |
| CN | 202311204 U | 7/2012 |
| CN | 202311263 U | 7/2012 |
| CN | 202311315 U | 7/2012 |
| CN | 202311319 U | 7/2012 |
| CN | 202311320 U | 7/2012 |
| CN | 202311323 U | 7/2012 |
| CN | 202311324 U | 7/2012 |
| CN | 202334936 U | 7/2012 |
| CN | 202340887 U | 7/2012 |
| CN | 202340890 U | 7/2012 |
| CN | 202353830 U | 7/2012 |
| CN | 102613731 A | 8/2012 |
| CN | 102613735 A | 8/2012 |
| CN | 102631036 A | 8/2012 |
| CN | 102641003 A | 8/2012 |
| CN | 102641006 A | 8/2012 |
| CN | 202354393 U | 8/2012 |
| CN | 202354399 U | 8/2012 |
| CN | 202354495 U | 8/2012 |
| CN | 202364868 U | 8/2012 |
| CN | 202364869 U | 8/2012 |
| CN | 202375040 U | 8/2012 |
| CN | 202375077 U | 8/2012 |
| CN | 202375097 U | 8/2012 |
| CN | 202375098 U | 8/2012 |
| CN | 202375166 U | 8/2012 |
| CN | 202385785 U | 8/2012 |
| CN | 202396486 U | 8/2012 |
| CN | 202396511 U | 8/2012 |
| CN | 202396513 U | 8/2012 |
| CN | 102687915 A | 9/2012 |
| CN | 202407202 U | 9/2012 |
| CN | 202407327 U | 9/2012 |
| CN | 202409469 U | 9/2012 |
| CN | 202425613 U | 9/2012 |
| CN | 202425614 U | 9/2012 |
| CN | 202436153 U | 9/2012 |
| CN | 202436181 U | 9/2012 |
| CN | 202436184 U | 9/2012 |
| CN | 202436190 U | 9/2012 |
| CN | 202445148 U | 9/2012 |
| CN | 202445228 U | 9/2012 |
| CN | 102711296 A | 10/2012 |
| CN | 102726856 A | 10/2012 |
| CN | 202456454 U | 10/2012 |
| CN | 202456455 U | 10/2012 |
| CN | 202456465 U | 10/2012 |
| CN | 202476580 U | 10/2012 |
| CN | 202489249 U | 10/2012 |
| CN | 202496076 U | 10/2012 |
| CN | 202497542 U | 10/2012 |
| CN | 202504240 U | 10/2012 |
| CN | 202504241 U | 10/2012 |
| CN | 101396176 B | 11/2012 |
| CN | 102763908 A | 11/2012 |
| CN | 202514608 U | 11/2012 |
| CN | 202514634 U | 11/2012 |
| CN | 202514642 U | 11/2012 |
| CN | 202525104 U | 11/2012 |
| CN | 202525166 U | 11/2012 |
| CN | 202525234 U | 11/2012 |
| CN | 202525235 U | 11/2012 |
| CN | 202536132 U | 11/2012 |
| CN | 202536147 U | 11/2012 |
| CN | 202536148 U | 11/2012 |
| CN | 202536169 U | 11/2012 |
| CN | 202536175 U | 11/2012 |
| CN | 202536194 U | 11/2012 |
| CN | 202536235 U | 11/2012 |
| CN | 202552221 U | 11/2012 |

(56) References Cited

FOREIGN PATENT DOCUMENTS

| | | |
|---|---|---|
| CN | 202552255 U | 11/2012 |
| CN | 202566375 U | 12/2012 |
| CN | 202566376 U | 12/2012 |
| CN | 202566412 U | 12/2012 |
| CN | 202566460 U | 12/2012 |
| CN | 202588382 U | 12/2012 |
| CN | 202588391 U | 12/2012 |
| CN | 202603677 U | 12/2012 |
| CN | 202618285 U | 12/2012 |
| CN | 202618355 U | 12/2012 |
| CN | 202618382 U | 12/2012 |
| CN | 202618401 U | 12/2012 |
| CN | 202618402 U | 12/2012 |
| CN | 102860592 A | 1/2013 |
| CN | 102871243 A | 1/2013 |
| CN | 102894505 A | 1/2013 |
| CN | 202635651 U | 1/2013 |
| CN | 202635655 U | 1/2013 |
| CN | 202635678 U | 1/2013 |
| CN | 202637599 U | 1/2013 |
| CN | 202652567 U | 1/2013 |
| CN | 202653226 U | 1/2013 |
| CN | 202653229 U | 1/2013 |
| CN | 202664239 U | 1/2013 |
| CN | 202664255 U | 1/2013 |
| CN | 202665776 U | 1/2013 |
| CN | 202680516 U | 1/2013 |
| CN | 202680596 U | 1/2013 |
| CN | 202680610 U | 1/2013 |
| CN | 202697762 U | 1/2013 |
| CN | 202697783 U | 1/2013 |
| CN | 202697827 U | 1/2013 |
| CN | 101396179 B | 2/2013 |
| CN | 102920073 A | 2/2013 |
| CN | 102922822 A | 2/2013 |
| CN | 102935899 A | 2/2013 |
| CN | 102940326 A | 2/2013 |
| CN | 102945990 A | 2/2013 |
| CN | 202722552 U | 2/2013 |
| CN | 202722555 U | 2/2013 |
| CN | 202738126 U | 2/2013 |
| CN | 202738878 U | 2/2013 |
| CN | 202750724 U | 2/2013 |
| CN | 202750755 U | 2/2013 |
| CN | 202750768 U | 2/2013 |
| CN | 102972894 A | 3/2013 |
| CN | 102987607 A | 3/2013 |
| CN | 202760232 U | 3/2013 |
| CN | 202774235 U | 3/2013 |
| CN | 202774236 U | 3/2013 |
| CN | 202774266 U | 3/2013 |
| CN | 202774280 U | 3/2013 |
| CN | 202774823 U | 3/2013 |
| CN | 202800126 U | 3/2013 |
| CN | 202800173 U | 3/2013 |
| CN | 202800228 U | 3/2013 |
| CN | 202819642 U | 3/2013 |
| CN | 202819684 U | 3/2013 |
| CN | 202819735 U | 3/2013 |
| CN | 103027393 A | 4/2013 |
| CN | 202842430 U | 4/2013 |
| CN | 202857918 U | 4/2013 |
| CN | 202857986 U | 4/2013 |
| CN | 202873822 U | 4/2013 |
| CN | 202873832 U | 4/2013 |
| CN | 202890500 U | 4/2013 |
| CN | 202890505 U | 4/2013 |
| CN | 202890579 U | 4/2013 |
| CN | 202890586 U | 4/2013 |
| CN | 202890596 U | 4/2013 |
| CN | 202907220 U | 4/2013 |
| CN | 103120429 A | 5/2013 |
| CN | 202907835 U | 5/2013 |
| CN | 202907856 U | 5/2013 |
| CN | 202917999 U | 5/2013 |
| CN | 202919088 U | 5/2013 |
| CN | 202932081 U | 5/2013 |
| CN | 202932113 U | 5/2013 |
| CN | 202941426 U | 5/2013 |
| CN | 202941449 U | 5/2013 |
| CN | 202945469 U | 5/2013 |
| CN | 103158842 A | 6/2013 |
| CN | 103169169 A | 6/2013 |
| CN | 103169180 A | 6/2013 |
| CN | 202958912 U | 6/2013 |
| CN | 202958917 U | 6/2013 |
| CN | 202958919 U | 6/2013 |
| CN | 202958920 U | 6/2013 |
| CN | 202958932 U | 6/2013 |
| CN | 202958934 U | 6/2013 |
| CN | 202959019 U | 6/2013 |
| CN | 202980261 U | 6/2013 |
| CN | 202980262 U | 6/2013 |
| CN | 202980276 U | 6/2013 |
| CN | 202980312 U | 6/2013 |
| CN | 202999329 U | 6/2013 |
| CN | 202999362 U | 6/2013 |
| CN | 203015887 U | 6/2013 |
| CN | 203015910 U | 6/2013 |
| CN | 203015912 U | 6/2013 |
| CN | 103190718 A | 7/2013 |
| CN | 203040789 U | 7/2013 |
| CN | 203040791 U | 7/2013 |
| CN | 203047442 U | 7/2013 |
| CN | 203058369 U | 7/2013 |
| CN | 203058372 U | 7/2013 |
| CN | 203058373 U | 7/2013 |
| CN | 203058374 U | 7/2013 |
| CN | 203058420 U | 7/2013 |
| CN | 203078668 U | 7/2013 |
| CN | 203087552 U | 7/2013 |
| CN | 203087553 U | 7/2013 |
| CN | 203087574 U | 7/2013 |
| CN | 203087615 U | 7/2013 |
| CN | 203087620 U | 7/2013 |
| CN | 203087625 U | 7/2013 |
| CN | 103251171 A | 8/2013 |
| CN | 103263089 A | 8/2013 |
| CN | 203105651 U | 8/2013 |
| CN | 203105658 U | 8/2013 |
| CN | 203105719 U | 8/2013 |
| CN | 203105728 U | 8/2013 |
| CN | 203111384 U | 8/2013 |
| CN | 203116149 U | 8/2013 |
| CN | 203121063 U | 8/2013 |
| CN | 203121064 U | 8/2013 |
| CN | 203121065 U | 8/2013 |
| CN | 203121066 U | 8/2013 |
| CN | 203121092 U | 8/2013 |
| CN | 203121093 U | 8/2013 |
| CN | 203121098 U | 8/2013 |
| CN | 203137126 U | 8/2013 |
| CN | 203137137 U | 8/2013 |
| CN | 203168048 U | 9/2013 |
| CN | 203168066 U | 9/2013 |
| CN | 203182051 U | 9/2013 |
| CN | 203194607 U | 9/2013 |
| CN | 203194692 U | 9/2013 |
| CN | 203207215 U | 9/2013 |
| CN | 203207238 U | 9/2013 |
| CN | 203207260 U | 9/2013 |
| CN | 103355770 A | 10/2013 |
| CN | 203219947 U | 10/2013 |
| CN | 203228886 U | 10/2013 |
| CN | 203234889 U | 10/2013 |
| CN | 103404979 A | 11/2013 |
| CN | 203262310 U | 11/2013 |
| CN | 203290250 U | 11/2013 |
| CN | 203290264 U | 11/2013 |
| CN | 103445339 A | 12/2013 |
| CN | 203314152 U | 12/2013 |
| CN | 203314165 U | 12/2013 |
| CN | 203327971 U | 12/2013 |
| CN | 203327975 U | 12/2013 |

(56) References Cited

FOREIGN PATENT DOCUMENTS

| | | |
|---|---|---|
| CN | 203328067 U | 12/2013 |
| CN | 203341034 U | 12/2013 |
| CN | 203353709 U | 12/2013 |
| CN | 203353739 U | 12/2013 |
| CN | 103504631 A | 1/2014 |
| CN | 103504635 A | 1/2014 |
| CN | 203378058 U | 1/2014 |
| CN | 203407524 U | 1/2014 |
| CN | 103561494 A | 2/2014 |
| CN | 103564680 A | 2/2014 |
| CN | 103564879 A | 2/2014 |
| CN | 103584374 A | 2/2014 |
| CN | 103584377 A | 2/2014 |
| CN | 103600794 A | 2/2014 |
| CN | 203416829 U | 2/2014 |
| CN | 203424328 U | 2/2014 |
| CN | 203435709 U | 2/2014 |
| CN | 203446797 U | 2/2014 |
| CN | 103629874 A | 3/2014 |
| CN | 103653342 A | 3/2014 |
| CN | 103653382 A | 3/2014 |
| CN | 103653383 A | 3/2014 |
| CN | 203467707 U | 3/2014 |
| CN | 203467720 U | 3/2014 |
| CN | 203467721 U | 3/2014 |
| CN | 203467774 U | 3/2014 |
| CN | 203482922 U | 3/2014 |
| CN | 203482924 U | 3/2014 |
| CN | 203482925 U | 3/2014 |
| CN | 103705334 A | 4/2014 |
| CN | 103720074 A | 4/2014 |
| CN | 103720088 A | 4/2014 |
| CN | 103750576 A | 4/2014 |
| CN | 203505633 U | 4/2014 |
| CN | 203507471 U | 4/2014 |
| CN | 203523837 U | 4/2014 |
| CN | 203523882 U | 4/2014 |
| CN | 203538437 U | 4/2014 |
| CN | 203544242 U | 4/2014 |
| CN | 203555192 U | 4/2014 |
| CN | 203555193 U | 4/2014 |
| CN | 103767163 A | 5/2014 |
| CN | 103767180 A | 5/2014 |
| CN | 103783686 A | 5/2014 |
| CN | 103799576 A | 5/2014 |
| CN | 203575673 U | 5/2014 |
| CN | 203575674 U | 5/2014 |
| CN | 103844402 A | 6/2014 |
| CN | 103859624 A | 6/2014 |
| CN | 103876323 A | 6/2014 |
| CN | 203633551 U | 6/2014 |
| CN | 203646538 U | 6/2014 |
| CN | 203646554 U | 6/2014 |
| CN | 203662071 U | 6/2014 |
| CN | 203662074 U | 6/2014 |
| CN | 103892483 A | 7/2014 |
| CN | 203676165 U | 7/2014 |
| CN | 203676168 U | 7/2014 |
| CN | 203676192 U | 7/2014 |
| CN | 203676194 U | 7/2014 |
| CN | 203692594 U | 7/2014 |
| CN | 203692595 U | 7/2014 |
| CN | 203692624 U | 7/2014 |
| CN | 203709338 U | 7/2014 |
| CN | 203747519 U | 7/2014 |
| CN | 103976482 A | 8/2014 |
| CN | 104000322 A | 8/2014 |
| CN | 203748763 U | 8/2014 |
| CN | 203762389 U | 8/2014 |
| CN | 203762411 U | 8/2014 |
| CN | 203776189 U | 8/2014 |
| CN | 104013142 A | 9/2014 |
| CN | 104013143 A | 9/2014 |
| CN | 203801743 U | 9/2014 |
| CN | 203814627 U | 9/2014 |
| CN | 203814634 U | 9/2014 |
| CN | 104116155 A | 10/2014 |
| CN | 104116161 A | 10/2014 |
| CN | 104116172 A | 10/2014 |
| CN | 104116222 A | 10/2014 |
| CN | 104116242 A | 10/2014 |
| CN | 203851830 U | 10/2014 |
| CN | 203860518 U | 10/2014 |
| CN | 203884730 U | 10/2014 |
| CN | 203897362 U | 10/2014 |
| CN | 104126891 A | 11/2014 |
| CN | 104126926 A | 11/2014 |
| CN | 104146407 A | 11/2014 |
| CN | 203913479 U | 11/2014 |
| CN | 203942658 U | 11/2014 |
| CN | 203942659 U | 11/2014 |
| CN | 203943107 U | 11/2014 |
| CN | 104188122 A | 12/2014 |
| CN | 104188140 A | 12/2014 |
| CN | 104212172 A | 12/2014 |
| CN | 104223436 A | 12/2014 |
| CN | 203986148 U | 12/2014 |
| CN | 203986179 U | 12/2014 |
| CN | 203986189 U | 12/2014 |
| CN | 203986250 U | 12/2014 |
| CN | 203986256 U | 12/2014 |
| CN | 204015150 U | 12/2014 |
| CN | 204048077 U | 12/2014 |
| CN | 204048165 U | 12/2014 |
| CN | 204048246 U | 12/2014 |
| CN | 204063232 U | 12/2014 |
| CN | 104256917 A | 1/2015 |
| CN | 104256930 A | 1/2015 |
| CN | 104256935 A | 1/2015 |
| CN | 104305581 A | 1/2015 |
| CN | 104305584 A | 1/2015 |
| CN | 104315878 A | 1/2015 |
| CN | 204070590 U | 1/2015 |
| CN | 204091047 U | 1/2015 |
| CN | 204091049 U | 1/2015 |
| CN | 204091051 U | 1/2015 |
| CN | 204091070 U | 1/2015 |
| CN | 104323496 A | 2/2015 |
| CN | 104366746 A | 2/2015 |
| CN | 104366748 A | 2/2015 |
| CN | 204132461 U | 2/2015 |
| CN | 204132462 U | 2/2015 |
| CN | 204157684 U | 2/2015 |
| CN | 204157761 U | 2/2015 |
| CN | 204167412 U | 2/2015 |
| CN | 204169080 U | 2/2015 |
| CN | 204169081 U | 2/2015 |
| CN | 204169106 U | 2/2015 |
| CN | 204169149 U | 2/2015 |
| CN | 104413753 A | 3/2015 |
| CN | 104413782 A | 3/2015 |
| CN | 104432549 A | 3/2015 |
| CN | 104432550 A | 3/2015 |
| CN | 104432552 A | 3/2015 |
| CN | 104432553 A | 3/2015 |
| CN | 104432556 A | 3/2015 |
| CN | 104432557 A | 3/2015 |
| CN | 104432566 A | 3/2015 |
| CN | 104432567 A | 3/2015 |
| CN | 104432573 A | 3/2015 |
| CN | 104432574 A | 3/2015 |
| CN | 104432575 A | 3/2015 |
| CN | 104432576 A | 3/2015 |
| CN | 104432577 A | 3/2015 |
| CN | 104432610 A | 3/2015 |
| CN | 104432626 A | 3/2015 |
| CN | 104432810 A | 3/2015 |
| CN | 204181018 U | 3/2015 |
| CN | 204191614 U | 3/2015 |
| CN | 204191624 U | 3/2015 |
| CN | 204191625 U | 3/2015 |
| CN | 204191626 U | 3/2015 |
| CN | 204191637 U | 3/2015 |
| CN | 204191657 U | 3/2015 |

(56) References Cited

FOREIGN PATENT DOCUMENTS

| | | |
|---|---|---|
| CN | 204191660 U | 3/2015 |
| CN | 204193321 U | 3/2015 |
| CN | 204207074 U | 3/2015 |
| CN | 204217947 U | 3/2015 |
| CN | 204217949 U | 3/2015 |
| CN | 104490004 A | 4/2015 |
| CN | 104509993 A | 4/2015 |
| CN | 104544636 A | 4/2015 |
| CN | 104544712 A | 4/2015 |
| CN | 104571218 A | 4/2015 |
| CN | 204232341 U | 4/2015 |
| CN | 204232360 U | 4/2015 |
| CN | 204245230 U | 4/2015 |
| CN | 204259874 U | 4/2015 |
| CN | 204259876 U | 4/2015 |
| CN | 204259897 U | 4/2015 |
| CN | 204273393 U | 4/2015 |
| CN | 204279893 U | 4/2015 |
| CN | 204292272 U | 4/2015 |
| CN | 204292275 U | 4/2015 |
| CN | 104621799 A | 5/2015 |
| CN | 104621801 A | 5/2015 |
| CN | 104621802 A | 5/2015 |
| CN | 104621845 A | 5/2015 |
| CN | 104643306 A | 5/2015 |
| CN | 104643327 A | 5/2015 |
| CN | 204306094 U | 5/2015 |
| CN | 204317547 U | 5/2015 |
| CN | 204335909 U | 5/2015 |
| CN | 103251171 B | 6/2015 |
| CN | 103653382 B | 6/2015 |
| CN | 104664633 A | 6/2015 |
| CN | 104664649 A | 6/2015 |
| CN | 104664725 A | 6/2015 |
| CN | 104664729 A | 6/2015 |
| CN | 104664784 A | 6/2015 |
| CN | 104664817 A | 6/2015 |
| CN | 104664956 A | 6/2015 |
| CN | 104665026 A | 6/2015 |
| CN | 104687286 A | 6/2015 |
| CN | 104687317 A | 6/2015 |
| CN | 104687340 A | 6/2015 |
| CN | 104687422 A | 6/2015 |
| CN | 104705857 A | 6/2015 |
| CN | 104709404 A | 6/2015 |
| CN | 104720122 A | 6/2015 |
| CN | 204363039 U | 6/2015 |
| CN | 204363077 U | 6/2015 |
| CN | 204367511 U | 6/2015 |
| CN | 204393404 U | 6/2015 |
| CN | 204409673 U | 6/2015 |
| CN | 204409681 U | 6/2015 |
| CN | 204421756 U | 6/2015 |
| CN | 204423189 U | 6/2015 |
| CN | 104757712 A | 7/2015 |
| CN | 104757738 A | 7/2015 |
| CN | 204426803 U | 7/2015 |
| CN | 204444286 U | 7/2015 |
| CN | 204444375 U | 7/2015 |
| CN | 204452884 U | 7/2015 |
| CN | 204466997 U | 7/2015 |
| CN | 204468675 U | 7/2015 |
| CN | 204483105 U | 7/2015 |
| CN | 204483110 U | 7/2015 |
| CN | 204483111 U | 7/2015 |
| CN | 204483158 U | 7/2015 |
| CN | 204499544 U | 7/2015 |
| CN | 204499568 U | 7/2015 |
| CN | 204499571 U | 7/2015 |
| CN | 204501603 U | 7/2015 |
| CN | 103584374 B | 8/2015 |
| CN | 204519378 U | 8/2015 |
| CN | 204519403 U | 8/2015 |
| CN | 204536940 U | 8/2015 |
| CN | 204539497 U | 8/2015 |
| CN | 204540866 U | 8/2015 |
| CN | 204540867 U | 8/2015 |
| CN | 204540884 U | 8/2015 |
| CN | 204548326 U | 8/2015 |
| CN | 204561042 U | 8/2015 |
| CN | 204561045 U | 8/2015 |
| CN | 204561046 U | 8/2015 |
| CN | 204561048 U | 8/2015 |
| CN | 204561051 U | 8/2015 |
| CN | 204579923 U | 8/2015 |
| CN | 204579924 U | 8/2015 |
| CN | 204587129 U | 8/2015 |
| CN | 103653383 B | 9/2015 |
| CN | 104872825 A | 9/2015 |
| CN | 104872862 A | 9/2015 |
| CN | 104886808 A | 9/2015 |
| CN | 104921353 A | 9/2015 |
| CN | 204599368 U | 9/2015 |
| CN | 204617118 U | 9/2015 |
| CN | 204635163 U | 9/2015 |
| CN | 204653824 U | 9/2015 |
| CN | 204653848 U | 9/2015 |
| CN | 204653879 U | 9/2015 |
| CN | 104957781 A | 10/2015 |
| CN | 104958179 A | 10/2015 |
| CN | 104997168 A | 10/2015 |
| CN | 104997194 A | 10/2015 |
| CN | 204682558 U | 10/2015 |
| CN | 204682574 U | 10/2015 |
| CN | 204697317 U | 10/2015 |
| CN | 204697952 U | 10/2015 |
| CN | 204708067 U | 10/2015 |
| CN | 204709554 U | 10/2015 |
| CN | 105011416 A | 11/2015 |
| CN | 105054370 A | 11/2015 |
| CN | 105054388 A | 11/2015 |
| CN | 105054390 A | 11/2015 |
| CN | 105077731 A | 11/2015 |
| CN | 204742791 U | 11/2015 |
| CN | 204763437 U | 11/2015 |
| CN | 204763502 U | 11/2015 |
| CN | 204763553 U | 11/2015 |
| CN | 204763570 U | 11/2015 |
| CN | 204796807 U | 11/2015 |
| CN | 105146787 A | 12/2015 |
| CN | 105146802 A | 12/2015 |
| CN | 204812088 U | 12/2015 |
| CN | 204812091 U | 12/2015 |
| CN | 204812092 U | 12/2015 |
| CN | 204812227 U | 12/2015 |
| CN | 204812236 U | 12/2015 |
| CN | 204812280 U | 12/2015 |
| CN | 204861240 U | 12/2015 |
| CN | 204861279 U | 12/2015 |
| CN | 204861439 U | 12/2015 |
| CN | 204864390 U | 12/2015 |
| CN | 204888787 U | 12/2015 |
| CN | 204908022 U | 12/2015 |
| CN | 204908069 U | 12/2015 |
| CN | 204908075 U | 12/2015 |
| CN | 204908144 U | 12/2015 |
| CN | 102342600 B | 1/2016 |
| CN | 103629874 B | 1/2016 |
| CN | 105212344 A | 1/2016 |
| CN | 105231532 A | 1/2016 |
| CN | 105280982 A | 1/2016 |
| CN | 204937333 U | 1/2016 |
| CN | 204949575 U | 1/2016 |
| CN | 204949576 U | 1/2016 |
| CN | 204949577 U | 1/2016 |
| CN | 204965221 U | 1/2016 |
| CN | 204969572 U | 1/2016 |
| CN | 204969573 U | 1/2016 |
| CN | 204969711 U | 1/2016 |
| CN | 204972977 U | 1/2016 |
| CN | 204994657 U | 1/2016 |
| CN | 204994684 U | 1/2016 |
| CN | 105286123 A | 2/2016 |
| CN | 105286143 A | 2/2016 |

(56) References Cited

FOREIGN PATENT DOCUMENTS

| | | |
|---|---|---|
| CN | 105338668 A | 2/2016 |
| CN | 205005973 U | 2/2016 |
| CN | 205031414 U | 2/2016 |
| CN | 105361295 A | 3/2016 |
| CN | 105361298 A | 3/2016 |
| CN | 105361317 A | 3/2016 |
| CN | 105394838 A | 3/2016 |
| CN | 105411034 A | 3/2016 |
| CN | 105411051 A | 3/2016 |
| CN | 105433459 A | 3/2016 |
| CN | 205082764 U | 3/2016 |
| CN | 205093615 U | 3/2016 |
| CN | 205093667 U | 3/2016 |
| CN | 205106468 U | 3/2016 |
| CN | 104223458 B | 4/2016 |
| CN | 104720122 B | 4/2016 |
| CN | 105455247 A | 4/2016 |
| CN | 105455259 A | 4/2016 |
| CN | 105466057 A | 4/2016 |
| CN | 105476090 A | 4/2016 |
| CN | 105495716 A | 4/2016 |
| CN | 105495756 A | 4/2016 |
| CN | 205125121 U | 4/2016 |
| CN | 205125166 U | 4/2016 |
| CN | 205125167 U | 4/2016 |
| CN | 205142544 U | 4/2016 |
| CN | 205143656 U | 4/2016 |
| CN | 205162061 U | 4/2016 |
| CN | 205180439 U | 4/2016 |
| CN | 205180442 U | 4/2016 |
| CN | 103600794 B | 5/2016 |
| CN | 105533844 A | 5/2016 |
| CN | 105559208 A | 5/2016 |
| CN | 105581402 A | 5/2016 |
| CN | 205233527 U | 5/2016 |
| CN | 205250398 U | 5/2016 |
| CN | 205250425 U | 5/2016 |
| CN | 102612179 B | 6/2016 |
| CN | 104490004 B | 6/2016 |
| CN | 105615014 A | 6/2016 |
| CN | 105615017 A | 6/2016 |
| CN | 105615020 A | 6/2016 |
| CN | 105641784 A | 6/2016 |
| CN | 105661681 A | 6/2016 |
| CN | 205285078 U | 6/2016 |
| CN | 205285108 U | 6/2016 |
| CN | 205286665 U | 6/2016 |
| CN | 205306050 U | 6/2016 |
| CN | 205321309 U | 6/2016 |
| CN | 205321383 U | 6/2016 |
| CN | 205337659 U | 6/2016 |
| CN | 205337686 U | 6/2016 |
| CN | 205337735 U | 6/2016 |
| CN | 105795545 A | 7/2016 |
| CN | 205358269 U | 7/2016 |
| CN | 205358271 U | 7/2016 |
| CN | 205358276 U | 7/2016 |
| CN | 205358356 U | 7/2016 |
| CN | 205360251 U | 7/2016 |
| CN | 205378881 U | 7/2016 |
| CN | 205385877 U | 7/2016 |
| CN | 205385895 U | 7/2016 |
| CN | 205390431 U | 7/2016 |
| CN | 104315878 B | 8/2016 |
| CN | 105815847 A | 8/2016 |
| CN | 105852231 A | 8/2016 |
| CN | 105852275 A | 8/2016 |
| CN | 105876917 A | 8/2016 |
| CN | 105878010 A | 8/2016 |
| CN | 205409760 U | 8/2016 |
| CN | 205409799 U | 8/2016 |
| CN | 205409800 U | 8/2016 |
| CN | 205432220 U | 8/2016 |
| CN | 205432288 U | 8/2016 |
| CN | 205456088 U | 8/2016 |
| CN | 205456174 U | 8/2016 |
| CN | 205456207 U | 8/2016 |
| CN | 205456212 U | 8/2016 |
| CN | 205456215 U | 8/2016 |
| CN | 205456216 U | 8/2016 |
| CN | 205456217 U | 8/2016 |
| CN | 205456284 U | 8/2016 |
| CN | 205456292 U | 8/2016 |
| CN | 205456294 U | 8/2016 |
| CN | 205492749 U | 8/2016 |
| CN | 205512457 U | 8/2016 |
| CN | 205524659 U | 8/2016 |
| CN | 105962475 A | 9/2016 |
| CN | 105962476 A | 9/2016 |
| CN | 205547479 U | 9/2016 |
| CN | 205547481 U | 9/2016 |
| CN | 205549156 U | 9/2016 |
| CN | 205568012 U | 9/2016 |
| CN | 205585355 U | 9/2016 |
| CN | 205597177 U | 9/2016 |
| CN | 205601997 U | 9/2016 |
| CN | 105996219 A | 10/2016 |
| CN | 205611821 U | 10/2016 |
| CN | 205611822 U | 10/2016 |
| CN | 205611825 U | 10/2016 |
| CN | 205611837 U | 10/2016 |
| CN | 205624517 U | 10/2016 |
| CN | 205624602 U | 10/2016 |
| CN | 205624614 U | 10/2016 |
| CN | 205624619 U | 10/2016 |
| CN | 205624631 U | 10/2016 |
| CN | 205624728 U | 10/2016 |
| CN | 205648952 U | 10/2016 |
| CN | 205648986 U | 10/2016 |
| CN | 205658412 U | 10/2016 |
| CN | 205658414 U | 10/2016 |
| CN | 106072896 A | 11/2016 |
| CN | 106076957 A | 11/2016 |
| CN | 106102192 A | 11/2016 |
| CN | 106108148 A | 11/2016 |
| CN | 106108161 A | 11/2016 |
| CN | 106108182 A | 11/2016 |
| CN | 106136354 A | 11/2016 |
| CN | 106137517 A | 11/2016 |
| CN | 205695837 U | 11/2016 |
| CN | 205695839 U | 11/2016 |
| CN | 205695884 U | 11/2016 |
| CN | 205695892 U | 11/2016 |
| CN | 205695902 U | 11/2016 |
| CN | 205728215 U | 11/2016 |
| CN | 106174752 A | 12/2016 |
| CN | 106211382 A | 12/2016 |
| CN | 106255240 A | 12/2016 |
| CN | 205757339 U | 12/2016 |
| CN | 205757340 U | 12/2016 |
| CN | 205757342 U | 12/2016 |
| CN | 205757343 U | 12/2016 |
| CN | 205757396 U | 12/2016 |
| CN | 205757398 U | 12/2016 |
| CN | 205757401 U | 12/2016 |
| CN | 205792306 U | 12/2016 |
| CN | 205793408 U | 12/2016 |
| CN | 205794891 U | 12/2016 |
| CN | 205794896 U | 12/2016 |
| CN | 205813614 U | 12/2016 |
| CN | 205813650 U | 12/2016 |
| CN | 205829267 U | 12/2016 |
| CN | 205831108 U | 12/2016 |
| CN | 205831128 U | 12/2016 |
| CN | 205831155 U | 12/2016 |
| CN | 104305584 B | 1/2017 |
| CN | 105167241 B | 1/2017 |
| CN | 106263128 A | 1/2017 |
| CN | 106263130 A | 1/2017 |
| CN | 106307686 A | 1/2017 |
| CN | 106307719 A | 1/2017 |
| CN | 205848742 U | 1/2017 |
| CN | 205849602 U | 1/2017 |
| CN | 205856854 U | 1/2017 |

(56) References Cited

FOREIGN PATENT DOCUMENTS

| | | |
|---|---|---|
| CN | 205866029 U | 1/2017 |
| CN | 205866068 U | 1/2017 |
| CN | 205884753 U | 1/2017 |
| CN | 205902104 U | 1/2017 |
| CN | 106388070 A | 2/2017 |
| CN | 106418753 A | 2/2017 |
| CN | 205922985 U | 2/2017 |
| CN | 205923021 U | 2/2017 |
| CN | 205923022 U | 2/2017 |
| CN | 205923025 U | 2/2017 |
| CN | 205924294 U | 2/2017 |
| CN | 205947244 U | 2/2017 |
| CN | 205962924 U | 2/2017 |
| CN | 205962927 U | 2/2017 |
| CN | 205962972 U | 2/2017 |
| CN | 206006027 U | 3/2017 |
| CN | 206025276 U | 3/2017 |
| CN | 206025305 U | 3/2017 |
| CN | 206025306 U | 3/2017 |
| CN | 206025310 U | 3/2017 |
| CN | 206025311 U | 3/2017 |
| CN | 206043517 U | 3/2017 |
| CN | 206043595 U | 3/2017 |
| CN | 105455242 B | 4/2017 |
| CN | 106551748 A | 4/2017 |
| CN | 106579589 A | 4/2017 |
| CN | 206062198 U | 4/2017 |
| CN | 206062200 U | 4/2017 |
| CN | 206079087 U | 4/2017 |
| CN | 206079103 U | 4/2017 |
| CN | 206101685 U | 4/2017 |
| CN | 206101686 U | 4/2017 |
| CN | 206101690 U | 4/2017 |
| CN | 206101691 U | 4/2017 |
| CN | 206136324 U | 4/2017 |
| CN | 106617403 A | 5/2017 |
| CN | 106690482 A | 5/2017 |
| CN | 106690596 A | 5/2017 |
| CN | 106690597 A | 5/2017 |
| CN | 106723469 A | 5/2017 |
| CN | 106723470 A | 5/2017 |
| CN | 106723473 A | 5/2017 |
| CN | 106723533 A | 5/2017 |
| CN | 106741738 A | 5/2017 |
| CN | 206137253 U | 5/2017 |
| CN | 206137275 U | 5/2017 |
| CN | 206150513 U | 5/2017 |
| CN | 206150539 U | 5/2017 |
| CN | 206165897 U | 5/2017 |
| CN | 206182392 U | 5/2017 |
| CN | 206182431 U | 5/2017 |
| CN | 206197049 U | 5/2017 |
| CN | 206197120 U | 5/2017 |
| CN | 206197154 U | 5/2017 |
| CN | 106 859 204 A | 6/2017 |
| CN | 106820311 A | 6/2017 |
| CN | 106858777 A | 6/2017 |
| CN | 106889685 A | 6/2017 |
| CN | 106901439 A | 6/2017 |
| CN | 206227742 U | 6/2017 |
| CN | 206238527 U | 6/2017 |
| CN | 206247946 U | 6/2017 |
| CN | 206251954 U | 6/2017 |
| CN | 206251978 U | 6/2017 |
| CN | 206273146 U | 6/2017 |
| CN | 206294903 U | 7/2017 |
| CN | 206294923 U | 7/2017 |
| CN | 206303242 U | 7/2017 |
| CN | 206303294 U | 7/2017 |
| CN | 206324267 U | 7/2017 |
| CN | 206354489 U | 7/2017 |
| CN | 107014108 A | 8/2017 |
| CN | 107019272 A | 8/2017 |
| CN | 107019285 A | 8/2017 |
| CN | 107087833 A | 8/2017 |
| CN | 107095375 A | 8/2017 |
| CN | 206365512 U | 8/2017 |
| CN | 206371563 U | 8/2017 |
| CN | 206390317 U | 8/2017 |
| CN | 206403236 U | 8/2017 |
| CN | 206413761 U | 8/2017 |
| CN | 206413785 U | 8/2017 |
| CN | 206413786 U | 8/2017 |
| CN | 206413787 U | 8/2017 |
| CN | 206413809 U | 8/2017 |
| CN | 206433799 U | 8/2017 |
| CN | 206433804 U | 8/2017 |
| CN | 107156933 A | 9/2017 |
| CN | 107157006 A | 9/2017 |
| CN | 107183808 A | 9/2017 |
| CN | 206472893 U | 9/2017 |
| CN | 206498978 U | 9/2017 |
| CN | 206498979 U | 9/2017 |
| CN | 206507385 U | 9/2017 |
| CN | 107224012 A | 10/2017 |
| CN | 107232658 A | 10/2017 |
| CN | 107259669 A | 10/2017 |
| CN | 107280100 A | 10/2017 |
| CN | 206547913 U | 10/2017 |
| CN | 206565325 U | 10/2017 |
| CN | 206576324 U | 10/2017 |
| CN | 206576325 U | 10/2017 |
| CN | 206576327 U | 10/2017 |
| CN | 206576396 U | 10/2017 |
| CN | 206586423 U | 10/2017 |
| CN | 206586443 U | 10/2017 |
| CN | 206586444 U | 10/2017 |
| CN | 107307475 A | 11/2017 |
| CN | 107348577 A | 11/2017 |
| CN | 107348579 A | 11/2017 |
| CN | 107361431 A | 11/2017 |
| CN | 107361432 A | 11/2017 |
| CN | 107361433 A | 11/2017 |
| CN | 107373806 A | 11/2017 |
| CN | 107373815 A | 11/2017 |
| CN | 107373849 A | 11/2017 |
| CN | 107374811 A | 11/2017 |
| CN | 107397667 A | 11/2017 |
| CN | 206612236 U | 11/2017 |
| CN | 206620846 U | 11/2017 |
| CN | 206621623 U | 11/2017 |
| CN | 206623972 U | 11/2017 |
| CN | 206651424 U | 11/2017 |
| CN | 206651429 U | 11/2017 |
| CN | 206659172 U | 11/2017 |
| CN | 206659195 U | 11/2017 |
| CN | 206675025 U | 11/2017 |
| CN | 206685449 U | 11/2017 |
| CN | 106307719 B | 12/2017 |
| CN | 107432500 A | 12/2017 |
| CN | 107455817 A | 12/2017 |
| CN | 107510159 A | 12/2017 |
| CN | 206699452 U | 12/2017 |
| CN | 206699456 U | 12/2017 |
| CN | 206699522 U | 12/2017 |
| CN | 206699532 U | 12/2017 |
| CN | 206699547 U | 12/2017 |
| CN | 206714101 U | 12/2017 |
| CN | 206714141 U | 12/2017 |
| CN | 206721424 U | 12/2017 |
| CN | 206727717 U | 12/2017 |
| CN | 206729233 U | 12/2017 |
| CN | 206760793 U | 12/2017 |
| CN | 206761682 U | 12/2017 |
| CN | 206776781 U | 12/2017 |
| CN | 206776808 U | 12/2017 |
| CN | 206791710 U | 12/2017 |
| CN | 206791748 U | 12/2017 |
| CN | 206808715 U | 12/2017 |
| CN | 206808718 U | 12/2017 |
| CN | 206808740 U | 12/2017 |
| CN | 105466057 B | 1/2018 |
| CN | 105962475 B | 1/2018 |
| CN | 107594701 A | 1/2018 |

(56) References Cited

FOREIGN PATENT DOCUMENTS

| | | |
|---|---|---|
| CN | 206822061 U | 1/2018 |
| CN | 206836285 U | 1/2018 |
| CN | 206836286 U | 1/2018 |
| CN | 206852071 U | 1/2018 |
| CN | 206852112 U | 1/2018 |
| CN | 206880097 U | 1/2018 |
| CN | 206880106 U | 1/2018 |
| CN | 206893751 U | 1/2018 |
| CN | 206895096 U | 1/2018 |
| CN | 206895882 U | 1/2018 |
| CN | 206908872 U | 1/2018 |
| CN | 206909791 U | 1/2018 |
| CN | 206932049 U | 1/2018 |
| CN | 206933414 U | 1/2018 |
| CN | 107692369 A | 2/2018 |
| CN | 107692398 A | 2/2018 |
| CN | 107713057 A | 2/2018 |
| CN | 107713129 A | 2/2018 |
| CN | 107736656 A | 2/2018 |
| CN | 107736689 A | 2/2018 |
| CN | 107736963 A | 2/2018 |
| CN | 206949605 U | 2/2018 |
| CN | 206962316 U | 2/2018 |
| CN | 206964045 U | 2/2018 |
| CN | 206964046 U | 2/2018 |
| CN | 206978790 U | 2/2018 |
| CN | 206994481 U | 2/2018 |
| CN | 207011737 U | 2/2018 |
| CN | 207023305 U | 2/2018 |
| CN | 207023320 U | 2/2018 |
| CN | 207039262 U | 2/2018 |
| CN | 207040986 U | 2/2018 |
| CN | 105054390 B | 3/2018 |
| CN | 107772565 A | 3/2018 |
| CN | 107811333 A | 3/2018 |
| CN | 107836761 A | 3/2018 |
| CN | 207054873 U | 3/2018 |
| CN | 207084155 U | 3/2018 |
| CN | 207084195 U | 3/2018 |
| CN | 207084196 U | 3/2018 |
| CN | 207084220 U | 3/2018 |
| CN | 207084225 U | 3/2018 |
| CN | 207084240 U | 3/2018 |
| CN | 207100615 U | 3/2018 |
| CN | 207118623 U | 3/2018 |
| CN | 207118625 U | 3/2018 |
| CN | 207123730 U | 3/2018 |
| CN | 207125344 U | 3/2018 |
| CN | 207125352 U | 3/2018 |
| CN | 207135291 U | 3/2018 |
| CN | 207136293 U | 3/2018 |
| CN | 207151977 U | 3/2018 |
| CN | 207151978 U | 3/2018 |
| CN | 107927937 A | 4/2018 |
| CN | 107927939 A | 4/2018 |
| CN | 107960691 A | 4/2018 |
| CN | 207185976 U | 4/2018 |
| CN | 207201016 U | 4/2018 |
| CN | 207202071 U | 4/2018 |
| CN | 207220195 U | 4/2018 |
| CN | 207220200 U | 4/2018 |
| CN | 207233916 U | 4/2018 |
| CN | 207236181 U | 4/2018 |
| CN | 207252801 U | 4/2018 |
| CN | 207252836 U | 4/2018 |
| CN | 207252858 U | 4/2018 |
| CN | 207269901 U | 4/2018 |
| CN | 106723472 B | 5/2018 |
| CN | 107978697 A | 5/2018 |
| CN | 107997257 A | 5/2018 |
| CN | 108024582 A | 5/2018 |
| CN | 108041713 A | 5/2018 |
| CN | 108041723 A | 5/2018 |
| CN | 207285262 U | 5/2018 |
| CN | 207285265 U | 5/2018 |
| CN | 207322729 U | 5/2018 |
| CN | 207322768 U | 5/2018 |
| CN | 207322780 U | 5/2018 |
| CN | 207341262 U | 5/2018 |
| CN | 207355520 U | 5/2018 |
| CN | 207400364 U | 5/2018 |
| CN | 207411527 U | 5/2018 |
| CN | 108113071 A | 6/2018 |
| CN | 108113072 A | 6/2018 |
| CN | 108158076 A | 6/2018 |
| CN | 108185544 A | 6/2018 |
| CN | 108196172 A | 6/2018 |
| CN | 108208962 A | 6/2018 |
| CN | 108208963 A | 6/2018 |
| CN | 108208978 A | 6/2018 |
| CN | 207428538 U | 6/2018 |
| CN | 207429255 U | 6/2018 |
| CN | 207442969 U | 6/2018 |
| CN | 207444311 U | 6/2018 |
| CN | 207461443 U | 6/2018 |
| CN | 207466937 U | 6/2018 |
| CN | 207476993 U | 6/2018 |
| CN | 207476995 U | 6/2018 |
| CN | 207477022 U | 6/2018 |
| CN | 207492147 U | 6/2018 |
| CN | 207519673 U | 6/2018 |
| CN | 207531918 U | 6/2018 |
| CN | 105996219 B | 7/2018 |
| CN | 108260887 A | 7/2018 |
| CN | 108294375 A | 7/2018 |
| CN | 108308750 A | 7/2018 |
| CN | 108308766 A | 7/2018 |
| CN | 207561427 U | 7/2018 |
| CN | 207574550 U | 7/2018 |
| CN | 207639701 U | 7/2018 |
| CN | 108366440 A | 8/2018 |
| CN | 108396527 A | 8/2018 |
| CN | 108433208 A | 8/2018 |
| CN | 108433209 A | 8/2018 |
| CN | 108433241 A | 8/2018 |
| CN | 108451073 A | 8/2018 |
| CN | 207705870 U | 8/2018 |
| CN | 207707333 U | 8/2018 |
| CN | 207707341 U | 8/2018 |
| CN | 207707344 U | 8/2018 |
| CN | 207707345 U | 8/2018 |
| CN | 207721259 U | 8/2018 |
| CN | 207754565 U | 8/2018 |
| CN | 207754597 U | 8/2018 |
| CN | 207767577 U | 8/2018 |
| CN | 207784339 U | 8/2018 |
| CN | 108 576 965 A | 9/2018 |
| CN | 108497576 A | 9/2018 |
| CN | 108497577 A | 9/2018 |
| CN | 108598619 A | 9/2018 |
| CN | 207803459 U | 9/2018 |
| CN | 207803511 U | 9/2018 |
| CN | 207836808 U | 9/2018 |
| CN | 207885694 U | 9/2018 |
| CN | 207885708 U | 9/2018 |
| CN | 207887201 U | 9/2018 |
| CN | 207897956 U | 9/2018 |
| CN | 207897957 U | 9/2018 |
| CN | 207912092 U | 9/2018 |
| CN | 106820310 B | 10/2018 |
| CN | 108685223 A | 10/2018 |
| CN | 207927901 U | 10/2018 |
| CN | 207940381 U | 10/2018 |
| CN | 207948969 U | 10/2018 |
| CN | 207949985 U | 10/2018 |
| CN | 207969687 U | 10/2018 |
| CN | 207969703 U | 10/2018 |
| CN | 2081182 U | 11/2018 |
| CN | 108720122 A | 11/2018 |
| CN | 108720135 A | 11/2018 |
| CN | 108741318 A | 11/2018 |
| CN | 108771293 A | 11/2018 |
| CN | 208030355 U | 11/2018 |
| CN | 208048066 U | 11/2018 |

(56) References Cited

FOREIGN PATENT DOCUMENTS

| | | |
|---|---|---|
| CN | 208064535 U | 11/2018 |
| CN | 208064538 U | 11/2018 |
| CN | 208114000 U | 11/2018 |
| CN | 208114107 U | 11/2018 |
| CN | 208129496 U | 11/2018 |
| CN | 208129525 U | 11/2018 |
| CN | 208144446 U | 11/2018 |
| CN | 208144464 U | 11/2018 |
| CN | 208144481 U | 11/2018 |
| CN | 208144482 U | 11/2018 |
| CN | 208144483 U | 11/2018 |
| CN | 208144519 U | 11/2018 |
| CN | 208160059 U | 11/2018 |
| CN | 208160079 U | 11/2018 |
| CN | 208160080 U | 11/2018 |
| CN | 108936853 A | 12/2018 |
| CN | 108936898 A | 12/2018 |
| CN | 109090734 A | 12/2018 |
| CN | 208176067 U | 12/2018 |
| CN | 208192320 U | 12/2018 |
| CN | 208242937 U | 12/2018 |
| CN | 208259071 U | 12/2018 |
| CN | 208259105 U | 12/2018 |
| CN | 208272040 U | 12/2018 |
| CN | 208286455 U | 12/2018 |
| CN | 106690482 B | 1/2019 |
| CN | 107373794 B | 1/2019 |
| CN | 109105984 A | 1/2019 |
| CN | 109123834 A | 1/2019 |
| CN | 109185959 A | 1/2019 |
| CN | 109222264 A | 1/2019 |
| CN | 109222289 A | 1/2019 |
| CN | 109224303 A | 1/2019 |
| CN | 208318300 U | 1/2019 |
| CN | 208318324 U | 1/2019 |
| CN | 208318325 U | 1/2019 |
| CN | 208318356 U | 1/2019 |
| CN | 208318359 U | 1/2019 |
| CN | 208354649 U | 1/2019 |
| CN | 208371053 U | 1/2019 |
| CN | 208387909 U | 1/2019 |
| CN | 208387923 U | 1/2019 |
| CN | 107361416 B | 2/2019 |
| CN | 107440177 B | 2/2019 |
| CN | 109315848 A | 2/2019 |
| CN | 109315853 A | 2/2019 |
| CN | 109315854 A | 2/2019 |
| CN | 109315857 A | 2/2019 |
| CN | 208446700 U | 2/2019 |
| CN | 208490912 U | 2/2019 |
| CN | 208490913 U | 2/2019 |
| CN | 208490941 U | 2/2019 |
| CN | 208490952 U | 2/2019 |
| CN | 208510093 U | 2/2019 |
| CN | 208523818 U | 2/2019 |
| CN | 109430975 A | 3/2019 |
| CN | 109452704 A | 3/2019 |
| CN | 109495988 A | 3/2019 |
| CN | 208597748 U | 3/2019 |
| CN | 208609957 U | 3/2019 |
| CN | 208624704 U | 3/2019 |
| CN | 208724950 U | 3/2019 |
| CN | 109588805 A | 4/2019 |
| CN | 109602100 A | 4/2019 |
| CN | 109606586 A | 4/2019 |
| CN | 109645590 A | 4/2019 |
| CN | 109674119 A | 4/2019 |
| CN | 109691703 A | 4/2019 |
| CN | 208798734 U | 4/2019 |
| CN | 109717527 A | 5/2019 |
| CN | 109731214 A | 5/2019 |
| CN | 109737628 A | 5/2019 |
| CN | 109744621 A | 5/2019 |
| CN | 109820261 A | 5/2019 |
| CN | 109820264 A | 5/2019 |
| CN | 208807660 U | 5/2019 |
| CN | 109832697 A | 6/2019 |
| CN | 109878663 A | 6/2019 |
| CN | 109892718 A | 6/2019 |
| CN | 109907403 A | 6/2019 |
| CN | 109907602 A | 6/2019 |
| CN | 208925280 U | 6/2019 |
| CN | 208925282 U | 6/2019 |
| CN | 208972700 U | 6/2019 |
| CN | 208987842 U | 6/2019 |
| CN | 106211382 B | 7/2019 |
| DE | 2922620 A1 | 12/1980 |
| DE | 3416366 A1 | 11/1985 |
| DE | 3837198 A1 | 5/1990 |
| DE | 3905570 A1 | 8/1990 |
| DE | 4104098 A1 | 8/1991 |
| DE | 199420307 U1 | 3/1995 |
| DE | 3837198 C2 | 10/1998 |
| DE | 19745889 A1 | 4/1999 |
| DE | 29918065 U1 | 2/2000 |
| DE | 20313577 U1 | 3/2004 |
| DE | 202004000874 U1 | 4/2004 |
| DE | 102005007598 A1 | 8/2006 |
| DE | 202009008352 U1 | 10/2009 |
| DE | 202009015379 U1 | 4/2010 |
| DE | 202010015873 U1 | 2/2011 |
| DE | 102011108323 A1 | 3/2012 |
| DE | 102011007419 A1 | 10/2012 |
| DE | 202012103836 U1 | 12/2012 |
| DE | 202012012440 U1 | 3/2013 |
| DE | 202015001940 U1 | 5/2015 |
| DE | 202015102699 U1 | 7/2015 |
| DE | 10 2014 205722 A1 | 10/2015 |
| DE | 202016004641 U1 | 9/2016 |
| DE | 102015113788 A1 | 2/2017 |
| DE | 102015113789 A1 | 2/2017 |
| DE | 202016005264 U1 | 6/2017 |
| DE | 10 2016 211 692 A1 | 1/2018 |
| DE | 202018103306 U1 | 10/2018 |
| DE | 102015113788 B4 | 2/2019 |
| EP | 124174 A1 | 11/1984 |
| EP | 203437 A2 | 12/1986 |
| EP | 203437 A3 | 1/1987 |
| EP | 124174 B1 | 3/1987 |
| EP | 243504 A1 | 11/1987 |
| EP | 243504 A4 | 3/1988 |
| EP | 287294 A1 | 10/1988 |
| EP | 203437 B1 | 2/1990 |
| EP | 580946 A1 | 2/1994 |
| EP | 580946 B1 | 5/1996 |
| EP | 803206 A1 | 10/1997 |
| EP | 834936 A1 | 4/1998 |
| EP | 803206 A4 | 5/1998 |
| EP | 948908 A2 | 10/1999 |
| EP | 948908 A3 | 12/1999 |
| EP | 979023 A1 | 2/2000 |
| EP | 1021064 A2 | 7/2000 |
| EP | 1049354 A1 | 11/2000 |
| EP | 1021064 A3 | 4/2001 |
| EP | 1164815 A1 | 12/2001 |
| EP | 1197722 A2 | 4/2002 |
| EP | 1201806 A2 | 5/2002 |
| EP | 1201806 A3 | 5/2002 |
| EP | 979023 B1 | 10/2002 |
| EP | 1197722 A3 | 5/2003 |
| EP | 1335830 A2 | 8/2003 |
| EP | 1335831 A1 | 8/2003 |
| EP | 1339259 A1 | 8/2003 |
| EP | 948908 B1 | 10/2003 |
| EP | 1358831 A1 | 11/2003 |
| EP | 803206 B1 | 12/2003 |
| EP | 1437438 A1 | 7/2004 |
| EP | 1537821 A2 | 6/2005 |
| EP | 1543275 A2 | 6/2005 |
| EP | 1552759 A1 | 7/2005 |
| EP | 1021064 B1 | 9/2005 |
| EP | 1358831 B1 | 11/2005 |
| EP | 1049354 B1 | 12/2005 |
| EP | 1201806 B1 | 12/2005 |

(56) References Cited

FOREIGN PATENT DOCUMENTS

| | | |
|---|---|---|
| EP | 1335830 A4 | 2/2006 |
| EP | 1629694 A1 | 3/2006 |
| EP | 1437438 A4 | 6/2006 |
| EP | 1537821 A3 | 6/2006 |
| EP | 1679984 A1 | 7/2006 |
| EP | 1 693 863 A1 | 8/2006 |
| EP | 1698242 A1 | 9/2006 |
| EP | 1703818 A1 | 9/2006 |
| EP | 1705956 A1 | 9/2006 |
| EP | 834936 A4 | 11/2006 |
| EP | 1437438 B1 | 1/2007 |
| EP | 1552759 A4 | 8/2007 |
| EP | 1882388 A2 | 1/2008 |
| EP | 1882391 A2 | 1/2008 |
| EP | 1914333 A1 | 4/2008 |
| EP | 1679984 B1 | 5/2008 |
| EP | 1698242 A4 | 6/2008 |
| EP | 1933655 A1 | 6/2008 |
| EP | 1679984 B8 | 8/2008 |
| EP | 2008498 A1 | 12/2008 |
| EP | 1335831 A4 | 1/2009 |
| EP | 2068667 A2 | 6/2009 |
| EP | 1537821 B1 | 11/2009 |
| EP | 2114185 A1 | 11/2009 |
| EP | 2133890 A2 | 12/2009 |
| EP | 2181614 A1 | 5/2010 |
| EP | 2182772 A1 | 5/2010 |
| EP | 2237752 A1 | 10/2010 |
| EP | 1335831 B1 | 1/2011 |
| EP | 1914333 A4 | 1/2011 |
| EP | 2133890 A3 | 3/2011 |
| EP | 2348947 A1 | 8/2011 |
| EP | 2348947 B1 | 7/2012 |
| EP | 2068667 A4 | 8/2012 |
| EP | 2481309 A1 | 8/2012 |
| EP | 1629694 B1 | 9/2012 |
| EP | 2237752 B1 | 12/2012 |
| EP | 2133890 B1 | 4/2013 |
| EP | 1914333 B1 | 5/2013 |
| EP | 2612420 A1 | 7/2013 |
| EP | 2633674 A1 | 9/2013 |
| EP | 2644045 A1 | 10/2013 |
| EP | 2679075 A1 | 1/2014 |
| EP | 2685954 A2 | 1/2014 |
| EP | 2687113 A1 | 1/2014 |
| EP | 2720656 A1 | 4/2014 |
| EP | 2679075 B1 | 6/2014 |
| EP | 2181614 B1 | 12/2014 |
| EP | 2834577 A2 | 2/2015 |
| EP | 2843634 A1 | 3/2015 |
| EP | 264404 5 B1 | 5/2015 |
| EP | 2866600 A1 | 5/2015 |
| EP | 2182772 B1 | 6/2015 |
| EP | 2685954 A4 | 7/2015 |
| EP | 2720656 A4 | 7/2015 |
| EP | 2917972 A1 | 9/2015 |
| EP | 2923592 A1 | 9/2015 |
| EP | 2481309 B1 | 1/2016 |
| EP | 2687113 B1 | 1/2016 |
| EP | 2967169 A1 | 1/2016 |
| EP | 3068189 A1 | 9/2016 |
| EP | 2967169 A4 | 11/2016 |
| EP | 2612420 A4 | 3/2017 |
| EP | 3172978 A1 | 5/2017 |
| EP | 3195744 A1 | 7/2017 |
| EP | 3202231 A2 | 8/2017 |
| EP | 3213599 A1 | 9/2017 |
| EP | 3225120 A1 | 10/2017 |
| EP | 3266279 A1 | 1/2018 |
| EP | 2917972 B1 | 3/2018 |
| EP | 3195744 A4 | 5/2018 |
| EP | 3326431 A1 | 5/2018 |
| EP | 2612420 B1 | 6/2018 |
| EP | 3213599 A4 | 6/2018 |
| EP | 3389124 A1 | 10/2018 |
| EP | 3391766 A1 | 10/2018 |
| EP | 3225120 B1 | 11/2018 |
| EP | 3407745 A1 | 12/2018 |
| EP | 3389124 B1 | 3/2019 |
| FR | 1605035 A | 8/1972 |
| FR | 2577116 A1 | 8/1986 |
| FR | 2577116 B1 | 3/1989 |
| FR | 2645410 A1 | 10/1990 |
| FR | 2837344 A3 | 9/2003 |
| FR | 2837344 B3 | 2/2004 |
| GB | 336270 A | 10/1930 |
| GB | 537351 A | 6/1941 |
| GB | 546812 A | 7/1942 |
| GB | 547842 A | 9/1942 |
| GB | 555125 A | 8/1943 |
| GB | 587189 A | 4/1947 |
| GB | 625218 A | 6/1949 |
| GB | 839916 A | 6/1960 |
| GB | 1415836 A | 11/1975 |
| GB | 2362803 A | 12/2001 |
| GB | 2442528 A | 4/2008 |
| GB | 2456489 A | 7/2009 |
| GB | 2457486 A | 8/2009 |
| GB | 201210819 | 8/2012 |
| IN | 290136 B | 12/2017 |
| JP | 3019730 A | 1/1991 |
| JP | 3053100 A | 3/1991 |
| JP | 3019730 Y2 | 4/1991 |
| JP | 3077692 A | 4/1991 |
| JP | 3087959 A | 4/1991 |
| JP | 3103005 A | 4/1991 |
| JP | 3111194 A | 5/1991 |
| JP | 3118697 A | 5/1991 |
| JP | 3121105 A | 5/1991 |
| JP | 3184363 A | 8/1991 |
| JP | 3188373 A | 8/1991 |
| JP | 3198957 A | 8/1991 |
| JP | 3205584 A | 9/1991 |
| JP | 3212963 A | 9/1991 |
| JP | 3220578 A | 9/1991 |
| JP | 3053100 Y2 | 11/1991 |
| JP | 3077692 B2 | 12/1991 |
| JP | 6250201 A | 9/1994 |
| JP | 03019730 U | 1/1996 |
| JP | 9111515 A | 4/1997 |
| JP | H09-259933 A | 10/1997 |
| JP | 03053100 U | 10/1998 |
| JP | 11189903 A | 7/1999 |
| JP | 11335909 A | 12/1999 |
| JP | 03019730 B2 | 3/2000 |
| JP | 03053100 B2 | 6/2000 |
| JP | 03077692 B1 | 8/2000 |
| JP | 03087959 B2 | 9/2000 |
| JP | 2000-290812 A | 10/2000 |
| JP | 03103005 B2 | 10/2000 |
| JP | 03111194 B2 | 11/2000 |
| JP | 03118697 B2 | 12/2000 |
| JP | 03121105 B2 | 12/2000 |
| JP | 03077692 U | 5/2001 |
| JP | 03184363 B2 | 7/2001 |
| JP | 03188373 B2 | 7/2001 |
| JP | 03198957 B2 | 8/2001 |
| JP | 03205584 B2 | 9/2001 |
| JP | 03212963 B2 | 9/2001 |
| JP | 03220578 B2 | 10/2001 |
| JP | 2002161410 A | 6/2002 |
| JP | 03087959 U | 8/2002 |
| JP | 03103005 U | 7/2004 |
| JP | 2004263325 A | 9/2004 |
| JP | 03111194 U | 7/2005 |
| JP | 2005344272 A | 12/2005 |
| JP | 03118697 U | 2/2006 |
| JP | 2006026266 A | 2/2006 |
| JP | 03121105 U | 4/2006 |
| JP | 03763039 B2 | 4/2006 |
| JP | 2006207099 A | 8/2006 |
| JP | 2008000304 A | 1/2008 |
| JP | 2009062638 A | 3/2009 |
| JP | 2009097106 A | 5/2009 |

(56) References Cited

FOREIGN PATENT DOCUMENTS

| | | | |
|---|---|---|---|
| JP | 2011094246 | A | 5/2011 |
| JP | 2011162931 | A | 8/2011 |
| JP | 03184363 | U | 6/2013 |
| JP | 2013227682 | A | 11/2013 |
| JP | 03188373 | U | 1/2014 |
| JP | 05397828 | B2 | 1/2014 |
| JP | 2014025157 | A | 2/2014 |
| JP | 2015036465 | A | 2/2015 |
| JP | 03198957 | U | 7/2015 |
| JP | 03205584 | U | 8/2016 |
| JP | 2016-156121 | A | 9/2016 |
| JP | 2017045577 | A | 3/2017 |
| JP | 2017110324 | A | 6/2017 |
| JP | 2017140343 | A | 8/2017 |
| JP | 03212963 | U | 10/2017 |
| JP | 06250201 | B2 | 12/2017 |
| JP | 2018-501771 | A | 1/2018 |
| JP | 2018048418 | A | 3/2018 |
| JP | 2018141256 | A | 9/2018 |
| JP | 2018141259 | A | 9/2018 |
| JP | 2018178268 | A | 11/2018 |
| JP | 2019-505699 | A | 2/2019 |
| JP | 03220578 | U | 3/2019 |
| JP | 06479551 | B2 | 3/2019 |
| JP | 2019039120 | A | 3/2019 |
| KR | 1999035271 | A | 5/1999 |
| KR | 1999035568 | A | 5/1999 |
| KR | 2000003647 | A | 1/2000 |
| KR | 2000044061 | A | 7/2000 |
| KR | 2000059195 | A | 10/2000 |
| KR | 2001099828 | A | 11/2001 |
| KR | 2002001702 | A | 1/2002 |
| KR | 2002019489 | A | 3/2002 |
| KR | 2002022210 | A | 3/2002 |
| KR | 2002027603 | A | 4/2002 |
| KR | 2002040352 | A | 5/2002 |
| KR | 350434 | B1 | 8/2002 |
| KR | 2002067481 | A | 8/2002 |
| KR | 2002073044 | A | 9/2002 |
| KR | 357754 | B1 | 10/2002 |
| KR | 2002075946 | A | 10/2002 |
| KR | 2002077834 | A | 10/2002 |
| KR | 2002083166 | A | 11/2002 |
| KR | 2002095967 | A | 12/2002 |
| KR | 2003001604 | A | 1/2003 |
| KR | 2003004365 | A | 1/2003 |
| KR | 2003008021 | A | 1/2003 |
| KR | 2003035902 | A | 5/2003 |
| KR | 2003037247 | A | 5/2003 |
| KR | 2003039405 | A | 5/2003 |
| KR | 2003042616 | A | 6/2003 |
| KR | 2003046028 | A | 6/2003 |
| KR | 2003053738 | A | 7/2003 |
| KR | 2003067802 | A | 8/2003 |
| KR | 2003069478 | A | 8/2003 |
| KR | 2003076025 | A | 9/2003 |
| KR | 2003079218 | A | 10/2003 |
| KR | 2003089640 | A | 11/2003 |
| KR | 2003092696 | A | 12/2003 |
| KR | 2003096190 | A | 12/2003 |
| KR | 2003096191 | A | 12/2003 |
| KR | 2004011160 | A | 2/2004 |
| KR | 2004018262 | A | 3/2004 |
| KR | 2004027372 | A | 4/2004 |
| KR | 2004032347 | A | 4/2004 |
| KR | 2004035572 | A | 4/2004 |
| KR | 2004041041 | A | 5/2004 |
| KR | 2004046738 | A | 6/2004 |
| KR | 357754 | Y1 | 7/2004 |
| KR | 2004057487 | A | 7/2004 |
| KR | 2004062152 | A | 7/2004 |
| KR | 2004066484 | A | 7/2004 |
| KR | 2004066485 | A | 7/2004 |
| KR | 2004073962 | A | 8/2004 |
| KR | 2004077858 | A | 9/2004 |
| KR | 2005040873 | A | 5/2005 |
| KR | 2005049433 | A | 5/2005 |
| KR | 2005055559 | A | 6/2005 |
| KR | 2006040798 | A | 5/2006 |
| KR | 2006058172 | A | 5/2006 |
| KR | 2006069778 | A | 6/2006 |
| KR | 2007036273 | A | 4/2007 |
| KR | 721723 | B1 | 5/2007 |
| KR | 721724 | B1 | 5/2007 |
| KR | 2007106671 | A | 11/2007 |
| KR | 781319 | B1 | 12/2007 |
| KR | 2008000802 | A | 1/2008 |
| KR | 838577 | B1 | 6/2008 |
| KR | 865847 | B1 | 10/2008 |
| KR | 886001 | B1 | 3/2009 |
| KR | 2010003642 | A | 1/2010 |
| KR | 2010007868 | A | 2/2010 |
| KR | 2010088044 | A | 8/2010 |
| KR | 984504 | B1 | 9/2010 |
| KR | 2010118047 | A | 11/2010 |
| KR | 2011001806 | A | 1/2011 |
| KR | 2011006320 | A | 1/2011 |
| KR | 1040962 | B1 | 6/2011 |
| KR | 2011079602 | A | 7/2011 |
| KR | 2011080190 | A | 7/2011 |
| KR | 2011080207 | A | 7/2011 |
| KR | 2011109083 | A | 10/2011 |
| KR | 2011137534 | A | 12/2011 |
| KR | 201201633 | U | 3/2012 |
| KR | 1201633 | B1 | 11/2012 |
| KR | 2013020178 | A | 2/2013 |
| KR | 1326218 | B1 | 11/2013 |
| KR | 1334394 | B1 | 12/2013 |
| KR | 1344033 | B1 | 1/2014 |
| KR | 1414532 | B1 | 7/2014 |
| KR | 1434609 | B1 | 9/2014 |
| KR | 1434610 | B1 | 9/2014 |
| KR | 1464871 | B1 | 11/2014 |
| KR | 2015039666 | A | 4/2015 |
| KR | 1521898 | B1 | 5/2015 |
| KR | 1525726 | B1 | 6/2015 |
| KR | 1540477 | B1 | 7/2015 |
| KR | 1552654 | B1 | 9/2015 |
| KR | 10-2015-0118254 | | 10/2015 |
| KR | 1568673 | B1 | 11/2015 |
| KR | 1570875 | B1 | 12/2015 |
| KR | 1612921 | B1 | 4/2016 |
| KR | 1629280 | B1 | 6/2016 |
| KR | 1660178 | B1 | 9/2016 |
| KR | 1715221 | B1 | 3/2017 |
| KR | 2017023413 | A | 3/2017 |
| KR | 1747247 | B1 | 6/2017 |
| KR | 1755618 | B1 | 7/2017 |
| KR | 10-2018-0001659 | | 1/2018 |
| KR | 1843454 | B1 | 3/2018 |
| KR | 2018069149 | A | 6/2018 |
| KR | 1890690 | B1 | 8/2018 |
| KR | 1918202 | B1 | 11/2018 |
| KR | 1940654 | B1 | 4/2019 |
| KR | 2019044461 | A | 4/2019 |
| KR | 2019055358 | A | 5/2019 |
| KR | 2019057812 | A | 5/2019 |
| KR | 2019073230 | A | 6/2019 |
| MX | 351746 | B | 10/2017 |
| RU | 9123 | U1 | 2/1999 |
| RU | 58860 | U1 | 12/2006 |
| RU | 72823 | U1 | 5/2008 |
| RU | 137805 | U1 | 2/2014 |
| RU | 166793 | U1 | 12/2016 |
| TW | M250560 | U | 11/2004 |
| TW | M266714 | U | 6/2005 |
| TW | M272398 | U | 8/2005 |
| TW | M310601 | U | 5/2007 |
| TW | M319743 | U | 10/2007 |
| TW | M333803 | U | 5/2009 |
| TW | M356396 | U | 5/2009 |
| TW | M359473 | U | 2/2010 |
| TW | M373838 | U | 2/2010 |
| TW | M374271 | U | 2/2010 |

(56) References Cited

FOREIGN PATENT DOCUMENTS

| | | |
|---|---|---|
| TW | M383311 U | 7/2010 |
| TW | M402002 U | 4/2011 |
| TW | M415099 U | 11/2011 |
| TW | M424790 U | 3/2012 |
| TW | M431584 U | 6/2012 |
| TW | I368017 B | 7/2012 |
| TW | M440662 U | 11/2012 |
| TW | M441346 U | 11/2012 |
| TW | I387116 B | 2/2013 |
| TW | M489484 U | 11/2014 |
| TW | M491313 U | 12/2014 |
| TW | M501742 U | 6/2015 |
| TW | M522013 U | 5/2016 |
| TW | M524084 U | 6/2016 |
| TW | M528614 U | 9/2016 |
| TW | 201701786 A | 1/2017 |
| TW | M559606 U | 5/2018 |
| WO | WO 1995021547 A1 | 8/1995 |
| WO | WO 1996019125 A1 | 6/1996 |
| WO | WO 2003028408 A1 | 4/2003 |
| WO | WO 2003059099 A1 | 7/2003 |
| WO | WO 2005028736 A1 | 3/2005 |
| WO | WO 2005122807 A1 | 12/2005 |
| WO | WO 2008006731 A1 | 1/2008 |
| WO | WO 2008036283 A2 | 3/2008 |
| WO | WO 2008036283 A3 | 7/2008 |
| WO | WO 2012034416 A1 | 3/2012 |
| WO | WO 2012144742 A2 | 10/2012 |
| WO | WO 2012144742 A3 | 1/2013 |
| WO | WO 2014013347 A2 | 1/2014 |
| WO | WO 2014013347 A3 | 4/2014 |
| WO | WO 2015004379 A1 | 1/2015 |
| WO | WO 2015030204 A1 | 3/2015 |
| WO | WO 2016035859 A1 | 3/2016 |
| WO | WO 2016046893 A1 | 3/2016 |
| WO | WO 2016082259 A1 | 6/2016 |
| WO | WO 2016/154271 A1 | 9/2016 |
| WO | WO 2016175346 A1 | 11/2016 |
| WO | WO 2017054227 A1 | 4/2017 |
| WO | WO 2017128167 A1 | 8/2017 |
| WO | WO 2017221204 A1 | 12/2017 |
| WO | WO 2018090874 A1 | 5/2018 |
| WO | WO 2018107559 A1 | 6/2018 |
| WO | WO 2018111178 A1 | 6/2018 |
| WO | WO 2019016524 A1 | 1/2019 |
| WO | WO 2019071058 A1 | 4/2019 |

OTHER PUBLICATIONS

Japanese Office Action and Translation, regarding Japanese Patent Application No. 2021-555425, dated Sep. 27, 2023, 12 pages.

International Search Report and Written Opinion dated Jun. 26, 2020, received in International Patent Application No. PCT/US2020/022441, in 18 pages.

European Office Action, regarding Application No. 20718028.2, dated May 30, 2023, 8 pages.

Office Action dated Sep. 19, 2024, received in Korean Patent Application No. KR 10-2021-7033412, in 12 pages.

\* cited by examiner

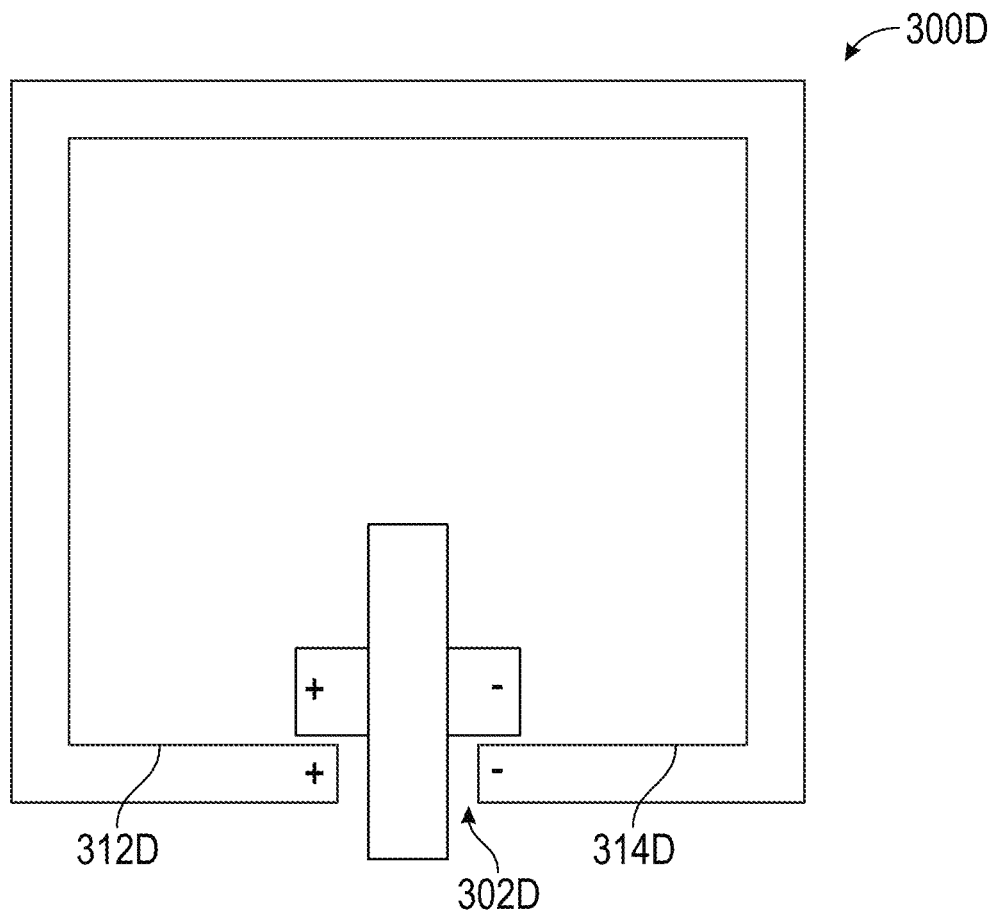
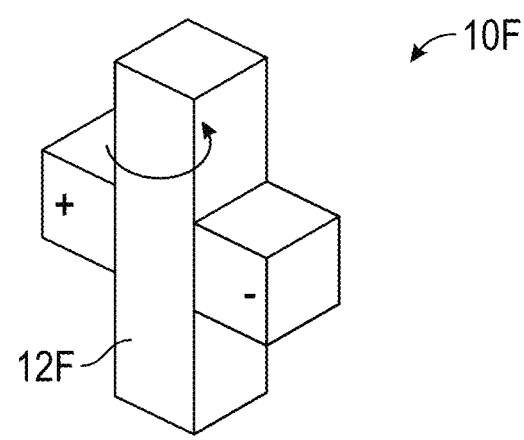
FIG. 10

ACTIVELY HEATED OR COOLED GARMENTS OR FOOTWEAR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention is directed to garments and footwear, and more particularly to actively heated or cooled garments or footwear.

Description of the Related Art

Garments (e.g., jackets, sweatshirts, pants, sweatpants, shirts) and footwear can have particular functionality (e.g., winterwear, summerwear, sportswear, etc.). However, the garments and footwear a user wears can depend on the weather (e.g., heavier or layered clothing in winter and lighter clothing in summer), which requires users to have various pieces of clothing for use depending on season, while storing away (e.g., in a closet, attic, etc.) clothing for a different season (e.g., storing winter clothing during summer). Additionally, sportswear is designed for use in a specific ambient temperature range. While sportwear can include material that wicks moisture or sweat, which can cool a user in hot weather, it may not properly keep a user warm if the temperature drops.

SUMMARY OF THE INVENTION

In accordance with one aspect of the disclosure, garments and/or footwear are provided with active temperature control.

In accordance with another aspect of the disclosure, garments have heating elements that can be powered (e.g., receive power from a power source, such as a battery) to heat one or more areas of the garment and thereby warm a portion of the user's body proximate the area of the garment being heated. The garment can optionally have one or more (e.g., multiple) areas that can be selectively heated (e.g., independently of each other, for example using MOSFETs in the circuitry to control such heaters) to warm one or more areas of the user's body wearing the garment. In one implementation, the garment can be a jacket or shirt with multiple (e.g., six) heating sections (e.g., upper chest, abdomen, upper back, lower back, left arm, right arm) that can be selectively heated (e.g., independently of each other).

In accordance with another aspect of the disclosure, garments and/or footwear are provided with active temperature control powered by one or more batteries carried by the garments and/or footwear. In one implementation, the one or more batteries are removable, allowing the washing of the garment (e.g., using a washing machine and dryer) without the batteries. In another implementation, the one or more batteries are configured to withstand the heat and impact in a washing machine and/or dryer during a washing process. Optionally, the batteries are rechargeable.

In accordance with another aspect of the disclosure, a hanger is provided for supporting and charging one or more batteries in a garment with active temperature control when the garment is hung on the hanger. The hanger can optionally include one or more power transmitters configured to transfer power to one or more power receivers in the garment when the garment is hung on the hanger, and circuitry to control delivery of power to the one or more power transmitters.

In one optional implementation, the one or more power transmitters of the hanger are inductive power transmitters (e.g., induction coils) that transfer power to inductive power receivers (e.g., induction coils) in the garment when the garment is hung on the hanger, e.g., such that the inductive power transmitters are proximate the inductive power receivers.

In one optional implementation, the one or more power transmitters of the hanger are galvanic power transmitters (e.g., electrical contacts) that transfer power to galvanic power receivers (e.g., contacts) in the garment when the garment is hung on the hanger, e.g., such that the galvanic power transmitters are proximate (e.g., in contact with) at least a portion of the galvanic power receivers.

In one optional implementation, the hanger is incorporated on top of a stand (e.g., a self-supporting stand).

In one optional implementation, the hanger can have one or more batteries (e.g., rechargeable batteries) that provide power to the circuitry and one or more power transmitters.

In another optional implementation, the hanger has one or more electrical contacts (e.g., in a hook of the hanger) configured to contact corresponding electrical contacts on a hook or bar (e.g., closet rod). The hook or bar can be connected to a power source (e.g., wall outlet) to provide power via the electrical contacts in the hook or bar and electrical contacts in the hanger to the one or more power transmitters in the hanger and/or to one or more batteries in the hanger (when optional batteries are included in the hanger). The one or more power transmitters in the hanger can transmit power to one or more power receivers in the garment (e.g., jacket, shirt) to charge one or more batteries of the garment.

In accordance with another aspect of the disclosure, the garment with active temperature control can be hung on a conventional hanger, which can be hung on a hook or bar (e.g., closet rod). The hook or bar can have one or more electrical connectors, and the hook or bar can be connected to a power source (e.g., via an electrical cord and electrical plug at the end of the cord). The garment can optionally include a tethered cable removably connected (e.g., with magnets) to an electrical contact on the garment. An opposite end of the tethered cable can be connected to the electrical connector of the hook or bar, thereby allowing power transfer to the garment (e.g., to one or more batteries of the garment) to charge the batteries, which can later power the one or more heating or cooling elements in the garment and other electronics (e.g., circuitry, sensors) of the garment.

In accordance with another aspect of the disclosure a drawer (e.g., in a dresser, chest of drawers) can have one or more connectors electrically connected to a power source (e.g., wall power via an electrical cord and electrical plug connected to a wall socket). One or more garments with active temperature control can be stored in the drawer. The garment(s) can optionally include a tethered cable removably connected (e.g., with magnets) to an electrical contact on the garment. An opposite end of the tethered cable can be connected to the electrical connector of the drawer, thereby allowing power transfer to the garment (e.g., to one or more batteries of the garment) to charge the batteries, which can later power the one or more heating or cooling elements in the garment and other electronics (e.g., circuitry, sensors) of the garment.

In accordance with another aspect of the disclosure, a shoe with active temperature control is provided. The shoe includes one or more batteries and circuitry operable to provide power to one or more heating elements. In one implementation, the one or more heating elements are incorporated into an insole of the shoe. In another implementation, the one or more heating elements are incorporated into (e.g., woven into) a fabric of a sock and electrical contacts between the sock an the shoe (e.g., insole of the shoe) transfer power from the one or more batteries in the shoe to the one or more heating elements in the sock.

In accordance with another aspect of the disclosure, gloves with active temperature control are provided. The gloves optionally have one or more batteries and circuitry that control delivery of power to one or more heating elements in the glove (e.g., woven into the fabric of the glove). In another implementation, the one or more batteries are excluded, and an electrical contact (e.g., a snap, electrically conductive Velcro, an induction coil) in the glove can be connected to an electrical contact (e.g., a snap, electrically conductive Velcro, an induction coil) in a sleeve of a garment with active temperature control to transfer power from the garment (e.g., from the batteries in the garment) to the heating elements in the glove.

In accordance with another aspect of the disclosure, pants with active temperature control are provided. The pants optionally have one or more batteries and circuitry that control delivery of power to one or more heating elements in the pants (e.g., woven into the fabric of the glove). In another implementation, the one or more batteries are excluded, and an electrical contact (e.g., a snap, electrically conductive Velcro, an induction coil) in the pants can be connected to an electrical contact (e.g., a snap, electrically conductive Velcro, an induction coil) in a waist of a garment (e.g., shirt) with active temperature control to transfer power from the garment (e.g., from the batteries in the garment) to the heating elements in the pants.

In accordance with another aspect of the disclosure, the active temperature control in the garment and/or footwear can be controlled wirelessly by the user via a user interface on a remote electronic device (e.g., screen on a smartphone via an app). The user can select with portion of the garment or footwear to heat and the heating level for it (e.g., high, medium, low). The remote electronic device can wirelessly communicate with a wireless receiver and/or transceiver in the garment or footwear (e.g., a wireless receiver or transceiver in the circuitry of the garment or footwear). Optionally, one or more sensors (e.g., temperature sensors, humidity sensors) in the garment or footwear can communicate with the circuitry in the garment or footwear and the circuitry can control the operation of the heating or cooling elements in the garment or footwear based on the sensed information (e.g., to automatically turn on, automatically turn off, or adjust an amount of power delivered to the heating or cooling elements).

BRIEF DESCRIPTION OF THE DRAWINGS

FIG. 10 is a schematic view of a hook of a hanger coupled to the hanging rod of FIG. 9.

DETAILED DESCRIPTION

Figure 1:
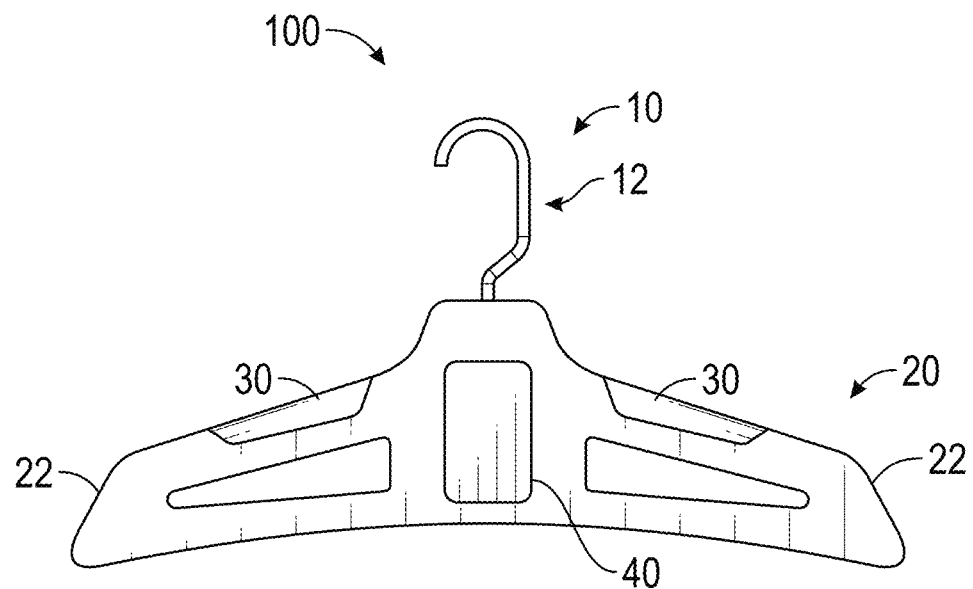
FIG. 1 is a schematic view of a hanger with power transmitters.

FIG. 1 shows a hanger 100. The hanger 100 has a hook 10 and a body 20 with two shoulder portions 22. The hook 10 has a body (e.g., curved body) 12 that can allow the hanger to be coupled (e.g., hung) from a hook or hanging rod (e.g., closet rod), as further discussed below.

The hanger 100 has one or more (e.g., a pair of) power transmitters 30 via which the hanger 100 can transfer power to a garment (e.g., shirt, jacket) with active temperature control electronics, as further discussed below. In one implementation, the hanger 100 optionally has one or more batteries (e.g., rechargeable batteries, lithium ion batteries) 40 that can power the power transmitter(s) 30 (e.g., when the hanger 100 is not coupled to a hook or rod that supplies power to the hanger 100). In one implementation, the one or more batteries 40 are removably coupled to the hanger 100 and can be detached for charging (e.g., on a charging pad or mat (e.g., via inductive coupling), or via electrical contacts between the batteries 40 and the charger.

Figure 2:
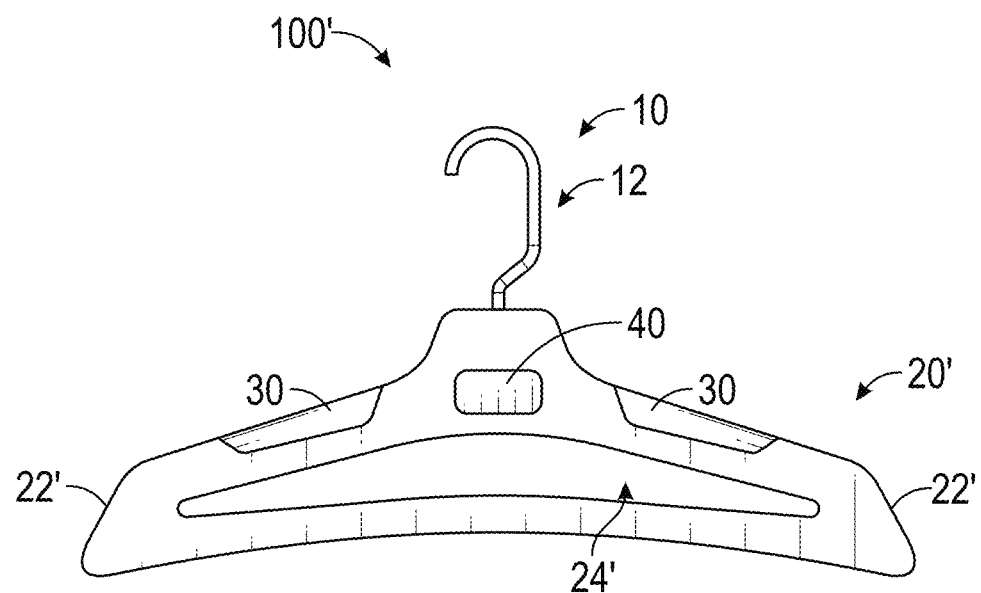
FIG. 2 is a schematic view of a hanger with power transmitters.

FIG. 2 schematically shows a hanger 100'. The hanger 100' is similar to the hanger 100 in FIG. 1. Thus, references numerals used to designate the various components of the hanger 100' are identical to those used for identifying the corresponding components of the hanger 100 in FIG. 1, except that a "'" is added to the numerical identifier. Therefore, the structure and description for the various components of the hanger 100 in FIG. 1 are understood to also apply to the corresponding components of the hanger 100' in FIG. 2, except as described below.

The hanger 100' differs from the hanger 100 in that the hanger body 20' has an opening 24' that allows a pair of pants or trousers to be hung from the hanger 100' (e.g., by extending the leg portions of the trousers or pants through the opening 24').

Figure 3A:
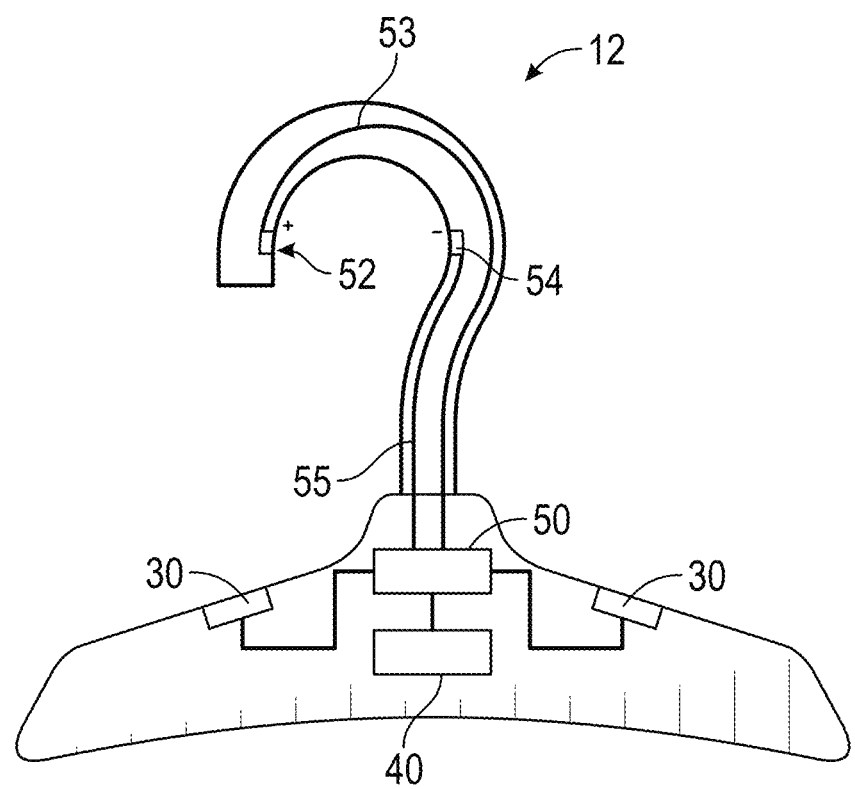
FIG. 3A is a schematic diagram of electronics in a hanger.

FIG. 3A is a schematic diagram of electronics in the hanger 100, 100'. The one or more (e.g., pair of) power transmitters 30 communicate (e.g., is electrically connected via electrical lines) with circuitry 50 (e.g., control circuitry). The circuitry 50 communicates (e.g., is electrically connected via electrical lines) with the one or more batteries 40. Electrical contacts 52, 54, which can be in one or more surfaces (e.g., opposing surfaces) of the hook body 12, communicate (e.g., are electrically connected) via electrical lines 53, 55, respectively, with the circuitry 50. The circuitry 50 can optionally control the delivery of power from one or both of a) the one or more batteries 40 and b) a power source connected to the electrical contacts 52, 54 to the power transmitter(s) 30. The circuitry 50 can optionally control the charging (e.g., via a charging circuit) of the one or more batteries 40 with power received from the power source via the electrical contacts 52, 54. In one implementation, the one or more batteries 40 are excluded, and the circuitry 50 controls delivery of power from a power source via the electrical contacts 52, 54 to the power transmitter(s) 30. The circuitry 50 can power one or more lights (not shown) on the hanger 100, 100' (e.g., on the hook 10), to indicate to the user one or more parameters of the operation of the hanger 100, 100' (e.g., batteries 40 fully charged, batteries 40 at low power, power being transferred via power transmitter(s) 30, etc.).

Figure 3B:
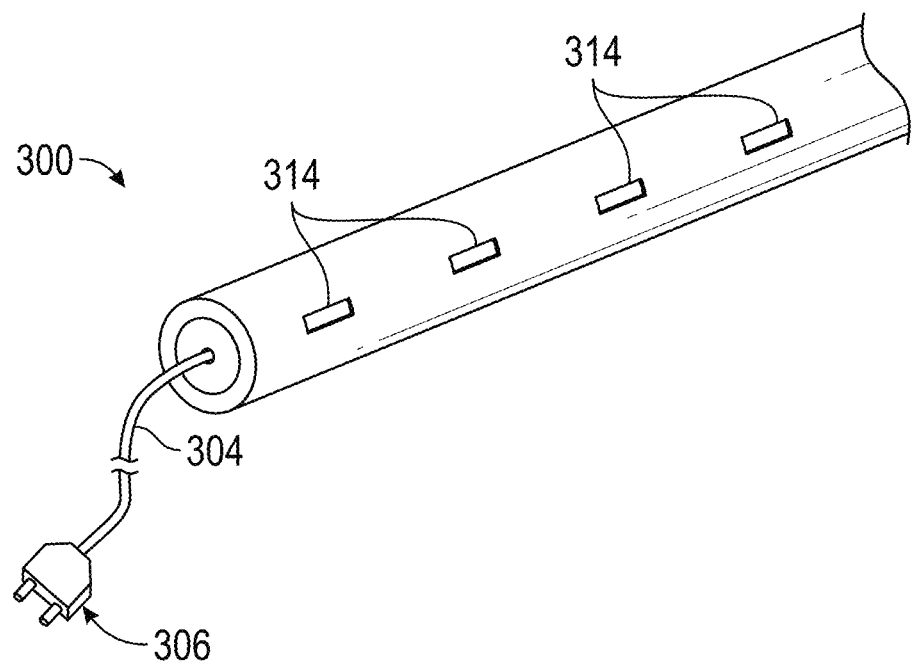
FIG. 3B is a schematic view of a hanging rod for use with one or more hangers.

FIG. 3B is a schematic view of a hanging rod 300 (e.g., a closet rod) on which a hanger, such as the hanger 100, 100' can be mounted. Optionally, the hanging rod 300 has a generally cylindrical shape (e.g., with a substantially circular cross-section transverse to a central axis of the rod 300). However, the hanging rod 300 can have other suitable shapes. The rod 300 can have one or more electrical connectors or contacts 314 on opposite sides of the rod 300. Though FIG. 3B only shows connectors or contacts 314 on one side of the rod 300, similar connectors or contacts are diametrically opposed on an opposite surface of the rod 300. The electrical connectors or contacts 314 can removably engage (e.g. contact) electrical contacts (such as electrical contacts 52, 54) of the hanger 100, 100' to transmit power from the rod 300 to the hanger 100, 100'. The hanging rod 300 has an electrical cord 304 electrically connected to the electrical connectors or contacts 314 and to an electrical plug 306 that can be connected to a wall outlet to provide power to the electrical connectors or contacts 314. Optionally, the electrical cord 304 can connect to the electrical connectors or contacts 314 via an adapter (not shown) to convert AC power to DC power and to reduce voltage from 120 VAC to a lower DC voltage suitable for powering the hanger 100, 100' and/or charging the one or more optional batteries 40 in the hanger 100, 100'. Optionally, the rod 300 can have one or more lights (not shown) that illuminate, to indicate to the user that power is being transferred from the rod 300 to the hanger 100, 100', 100".

Figure 4:
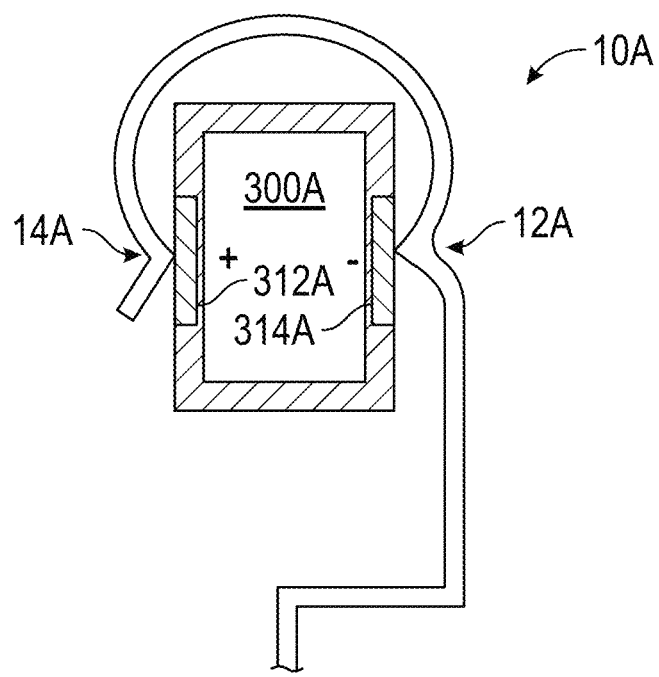
FIG. 4 is a schematic view of a hook of a hanger coupled to a hanging rod.

FIG. 4 shows a schematic view of a hook 10A for a hanger, such as the hanger 100, 100', that can hang from a hanging rod 300A (e.g., closet rod). The hook 100A has a pair of bent portions 12A, 14A that contact electrical contacts or connectors 312A, 314A of the rod 300A. The bent portions 12A, 14A can have electrical contacts (such as contacts 52, 54 in FIG. 3) that contact the electrical contacts or connectors 312A, 314A to transfer power from the hanging rod 300A (shown in cross-section) to the hanger via the hook 10A. The hanging rod 300A can optionally have a square cross-section (at least in portions of the rod 300A that receive the hook 10A). This allows conventional hangers to be hung on the rod 300B without the metal portion of the hook of such hanger (if metal hangers are used) inadvertently touching the electrical contacts 312A, 314A and causing a short circuit.

Figure 5:
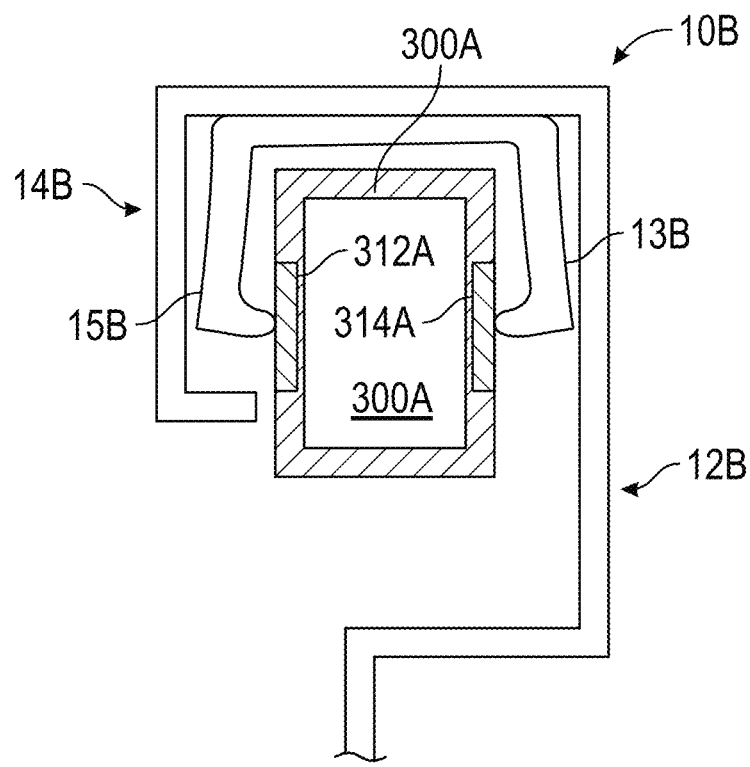
FIG. 5 is a schematic view of a hook of a hanger coupled to a hanging rod.

FIG. 5 shows a schematic view of a hook 10B for a hanger, such as hanger 100, 100'. The hook 10B is similar to the hook 10A in FIG. 4. Thus, references numerals used to designate the various components of the hook 10B are identical to those used for identifying the corresponding components of the hook 10A in FIG. 4, except that a "B" instead of an "A" is added to the numerical identifier. Therefore, the structure and description for the various components of the hook 10A in FIG. 4 are understood to also apply to the corresponding components of the hook 10B in FIG. 4, except as described below.

The hook 10B differs from the hook 10A in that it has deflectable (e.g., spring biased) electrical contacts 13B, 15B that contact the electrical connectors or contacts 312A, 314A of the hanging rod 300A. The deflectable electrical contacts 13B, 15B are disposed inward of hook portions 12B, 14B on opposite sides of the hook 10B.

Figure 6:
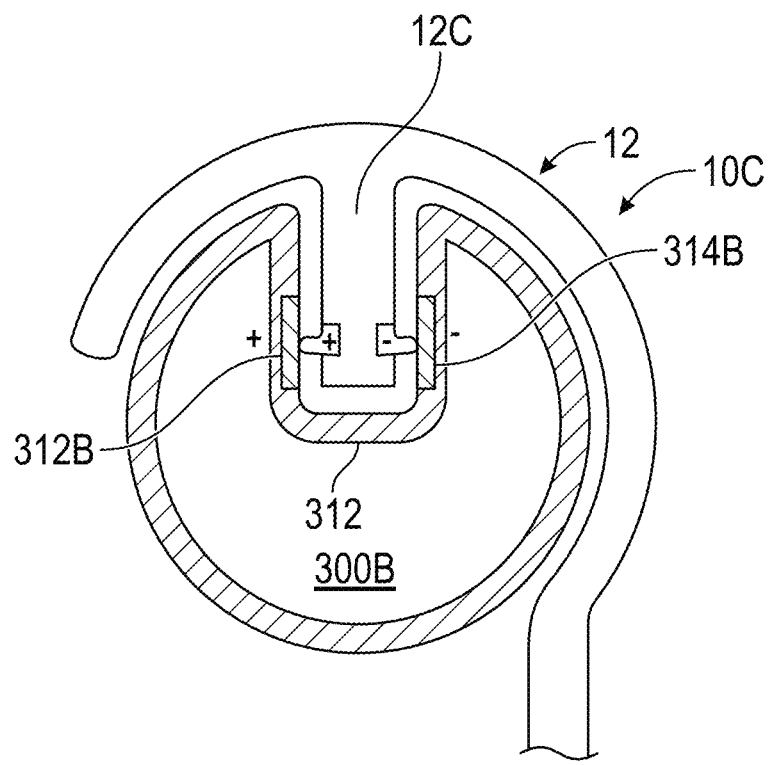
FIG. 6 is a schematic view of a hook of a hanger coupled to a hanging rod.

FIG. 6 shows a schematic view of a hook 10C for a hanger, such as the hanger 100, 100', that can hang from a hanging rod 300B (e.g., closet rod). The hook 100C has a body 12 with a prong 12C with electrical contacts on opposite sides of the prong 12C. The rod 300B (shown in cross-section) has a recess or cavity 312 on an upper end of the rod 300B into which the prong 12C of the hook 10C can extend (e.g., be inserted) when the hook 10C is disposed over the hanging rod 300B. The electrical contacts of the prong 12C of the hook 10C engage (e.g., contact) electrical connectors or contacts 312B, 314B of the rod 300B, where the electrical connectors or contacts 312B, 314B are disposed in walls that define the cavity or recess 312 of the rod 300B, thereby providing an electrical connection in a recessed portion of the rod 300B. The hanging rod 300B has an outer curved (e.g., circular) surface, except for locations on the top of the rod 300B that have the recess or cavity 312. This allows conventional hangers to be hung on the rod 300B without the metal portion of such hanger inadvertently touching the electrical contacts 312B, 314B and causing a short circuit, as well as inadvertent contact by a user (e.g., fingers of a user) with the electrical connectors or contacts 312B, 314B.

Figure 7:
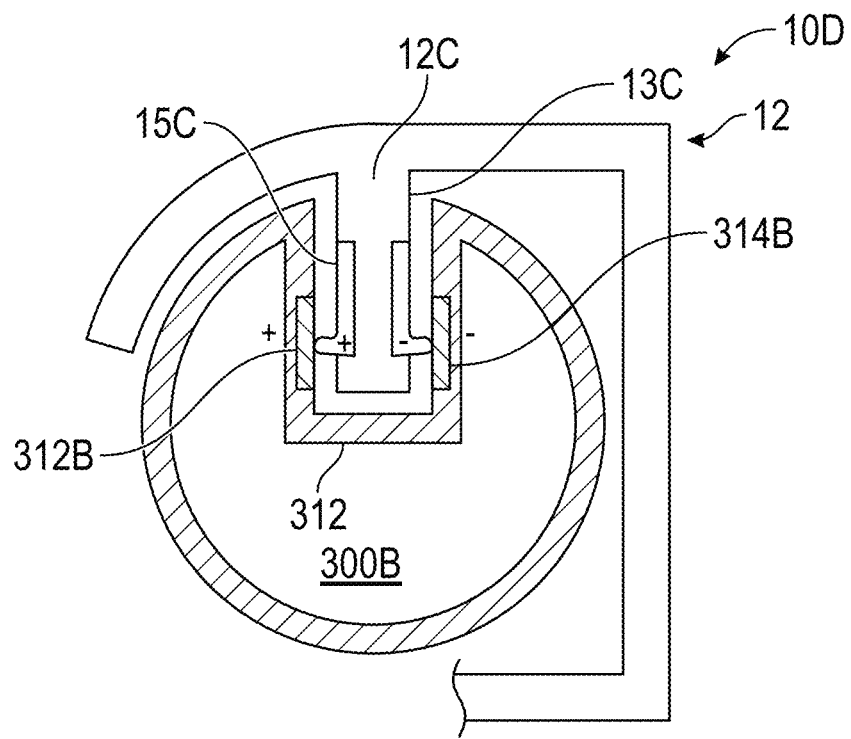
FIG. 7 is a schematic view of a hook of a hanger coupled to a hanging rod.

FIG. 7 shows a schematic view of a hook 10D for a hanger, such as hanger 100, 100'. The hook 10D is similar to the hook 10C in FIG. 6. Thus, references numerals used to designate the various components of the hook 10D are identical to those used for identifying the corresponding components of the hook 10C in FIG. 6, except that a "D" instead of an "C" is added to the numerical identifier. Therefore, the structure and description for the various components of the hook 10C in FIG. 6 are understood to also apply to the corresponding components of the hook 10B in FIG. 7, except as described below.

The hook 10D differs from the hook 10C in that it has deflectable (e.g., spring biased) electrical contacts 13D, 15D that contact the electrical connectors or contacts 312B, 314B of the hanging rod 300B (shown in cross-section). The deflectable electrical contacts 13D, 15D are disposed on the prong 12D that extends into the cavity or recess 312 of the hanging rod 300B.

Figure 8:
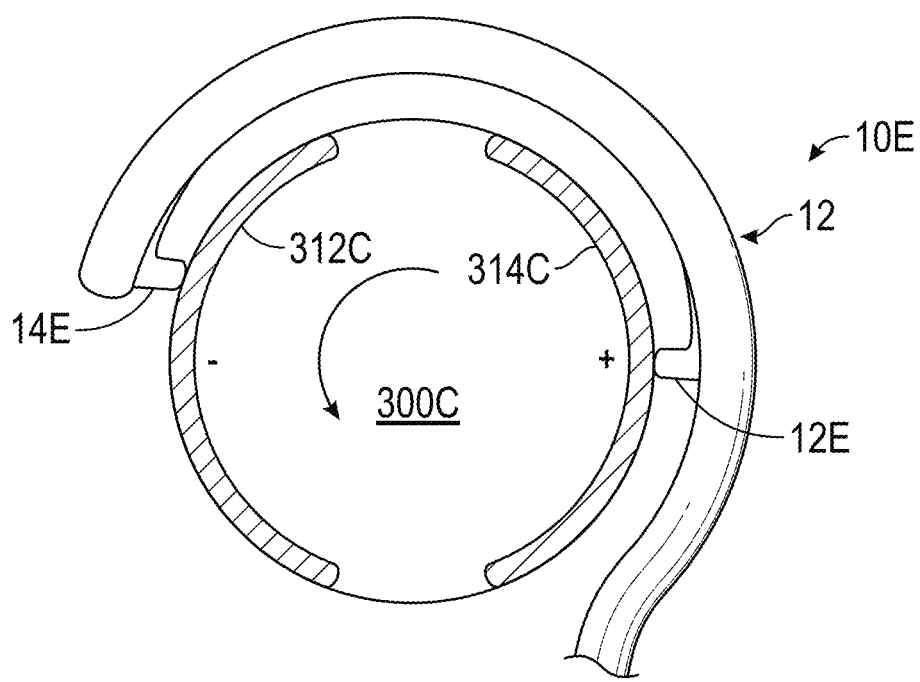
FIG. 8 is a schematic view of a hook of a hanger coupled to a hanging rod.

FIG. 8 shows a schematic view of a hook 10E for a hanger, such as hanger 100, 100'. The hook 10E is similar to the hook 10A in FIG. 4. Thus, references numerals used to designate the various components of the hook 10E are identical to those used for identifying the corresponding components of the hook 10A in FIG. 4, except that a "E" instead of an "A" is added to the numerical identifier. Therefore, the structure and description for the various components of the hook 10A in FIG. 4 are understood to also apply to the corresponding components of the hook 10E in FIG. 8, except as described below.

The hook 10E differs from the hook 10A in that the hook body 12 is curved (e.g., continuously curved) and has contacts 12E, 14E that engage electrical connectors or contacts 312C, 314C on opposite outer surfaces of the hanging rod 300C (e.g., closet rod). The hanging rod 300C (shown in cross-section) optionally has a circular shape or configuration.

Figure 9:
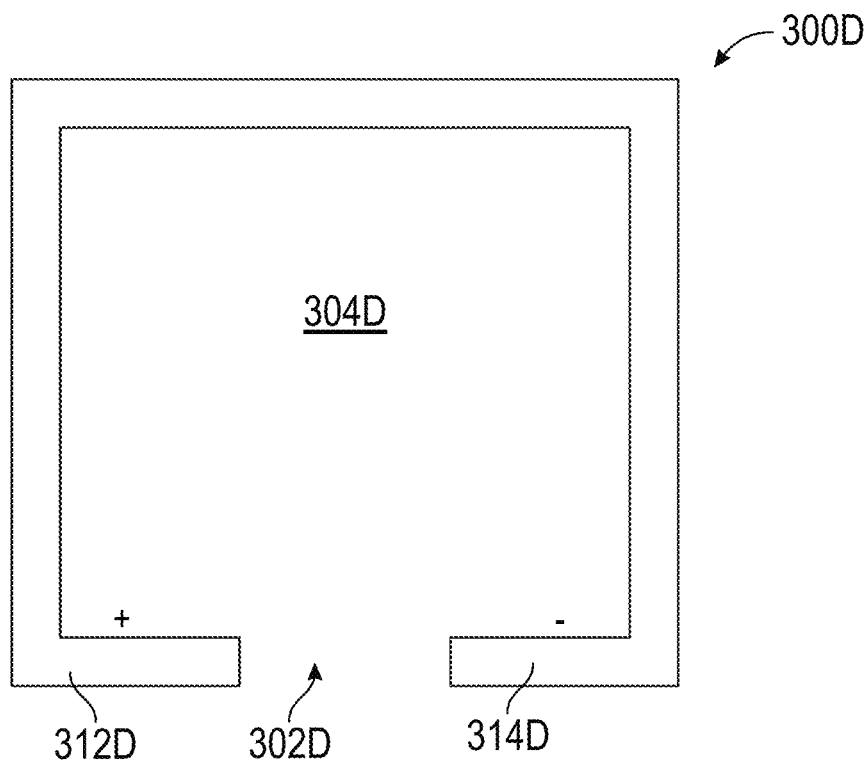
FIG. 9 is a schematic cross-sectional view of a hanging rod on which a hanger is hung.

FIG. 9 shows a schematic (cross-sectional) view of a hanging rod 300D, on which one or more hangers can be hung. The hanging rod 300D has a generally square or rectangular cross-section and defines a channel or cavity 304D accessible via an opening 302D. Walls of the channel (opposite each other across the opening 302D) can have electrical connectors or contacts 312D, 314D.

FIG. 10 shows a schematic view of a connector 10F of a hanger, such as the hanger 100, 100', that can have one or more prongs (a pair of prongs) 12F with electrical contacts. The connector 12F can have a pair of prongs 12F in a cross-shape. The connector 12F can be rotated to fit through the opening 302D in the hanging rod 300D so that the connector 12B extends into the cavity or channel 304D. The connector 12F can then be rotated to that the electrical contacts of the connector 12F engage (e.g., contact) the electrical connectors or contacts 312D, 314D of the hanging rod 300D. Accordingly, the connector 10F is supported from the hanging rod 300D by the same structure (e.g., cross-shaped or T-shaped connector 12F) that effects the electrical connection with the electrical connectors or contacts 312D, 314D of the hanging rod 300D.

Figure 11:
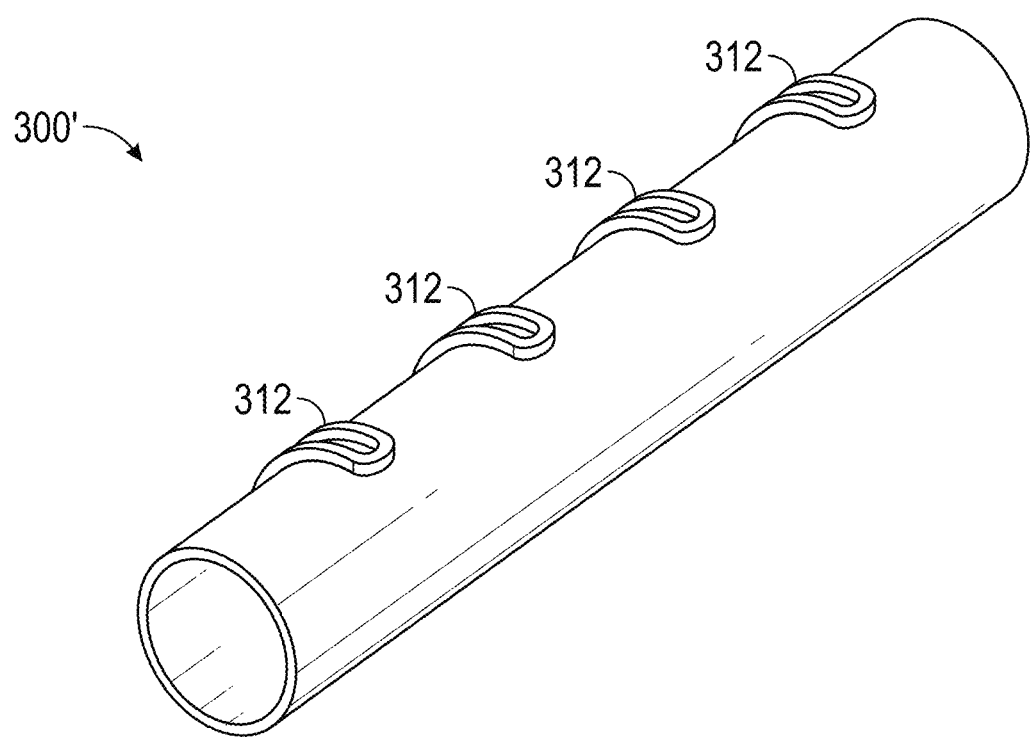
FIG. 11 is a schematic view of a hanging rod for use with one or more hangers.

FIG. 11 shows a schematic view of a rod 300' (e.g., a closet rod) from which hangers, such as hangers 100, 100' can hang. The rod 300' is similar to the rod 300 in FIG. 3B. Thus, references numerals used to designate the various components of the rod 300' are identical to those used for identifying the corresponding components of the rod 300 in FIG. 3B, except that a "'" is added to the numerical identifier. Therefore, the structure and description for the various components of the rod 300 in FIG. 3B are understood to also apply to the corresponding components of the rod 300' in FIG. 11, except as described below.

The rod 300' differs from the rod 300 in that the electrical contacts 312 are provided on a top surface or portion of the rod 300' instead of a side surface as in the rod 300.

Figure 12:
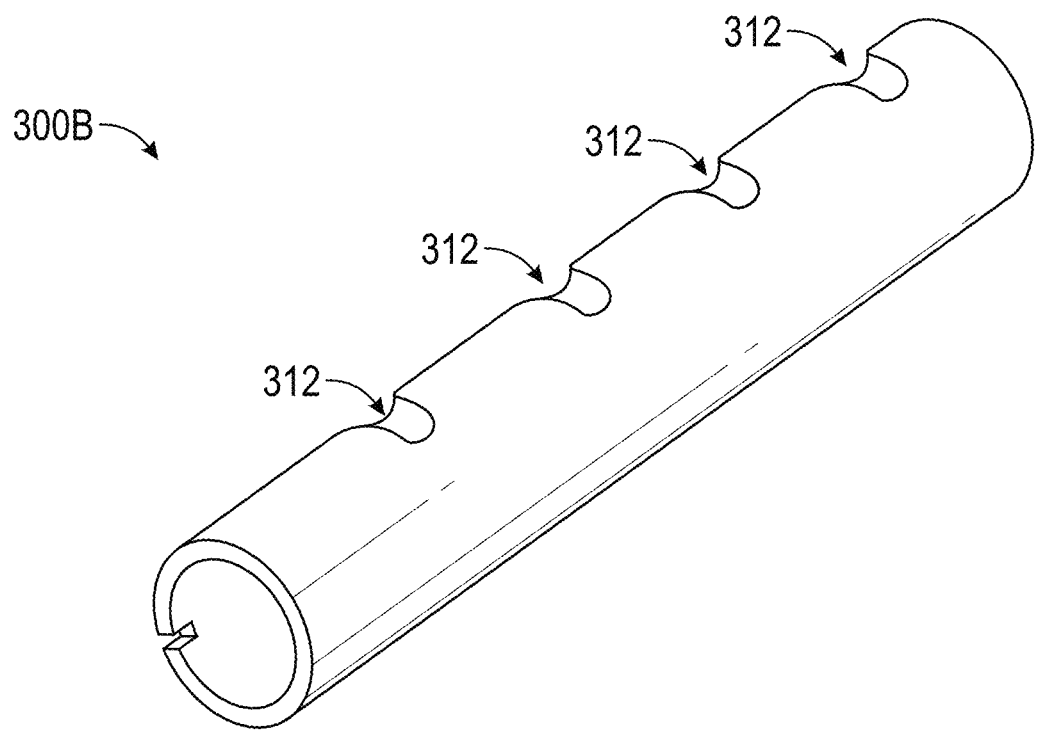
FIG. 12 is a schematic view of a hanging rod for use with one or more hangers.

FIG. 12 shows a schematic perspective view of the rod 300B (e.g., also shown in FIGS. 6-7). The rod 300B can have a plurality of recesses or cavities 312 via which electrical connectors or contacts 312B, 314B can be accessed and contacted by electrical contacts in a hook, such as hook 10C, 10D of a hanger, such as hanger 100, 100'.

Figure 13:
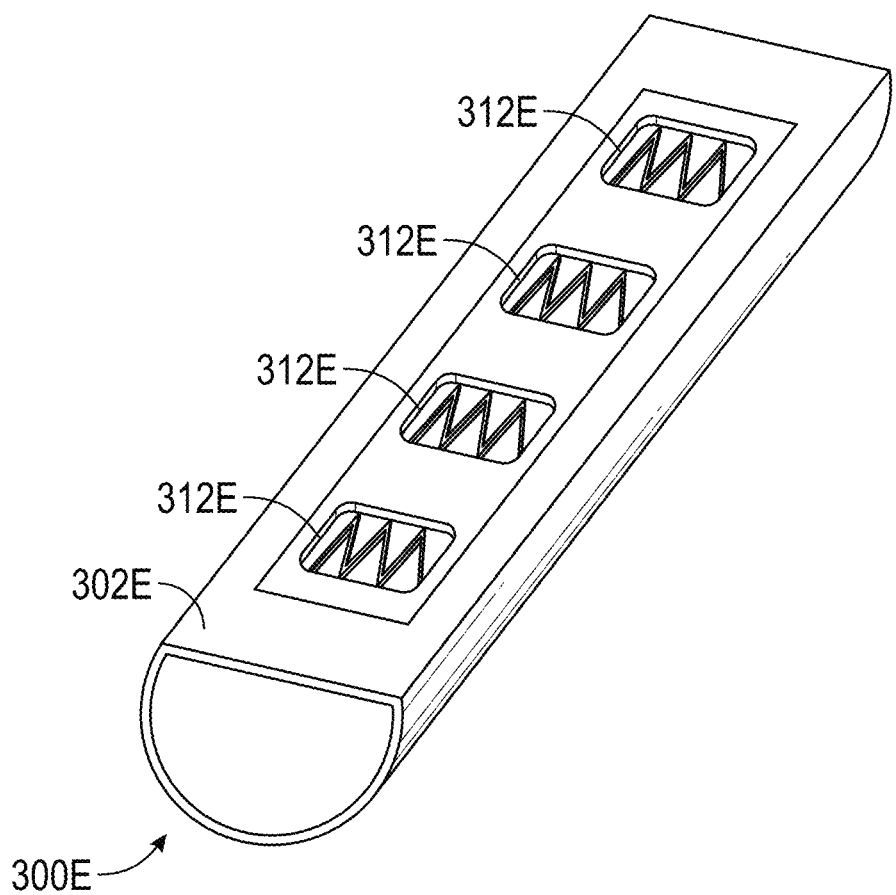
FIG. 13 is a schematic view of a hanging rod for use with one or more hangers.
Figure 14:
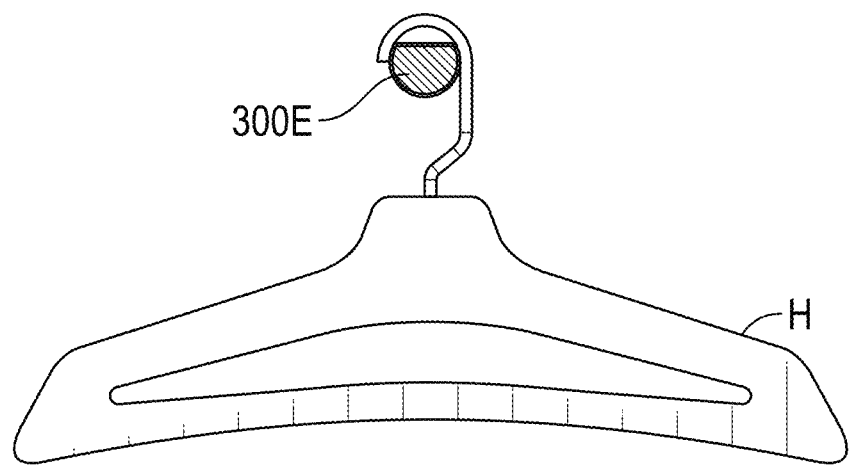
FIG. 14 is a schematic view of a conventional hanger hung on the hanging rod of FIG. 13.

FIG. 13 shows a schematic perspective view of a rod 300E (e.g., closet rod) from which hangers, such as hangers 100, 100' can hang. FIG. 14 shows a cross-sectional view of the rod 300E. The rod 300E is similar to the rod 300 in FIG. 3B. Thus, references numerals used to designate the various components of the rod 300E are identical to those used for identifying the corresponding components of the rod 300 in FIG. 3B, except that an "E" is added to the numerical identifier. Therefore, the structure and description for the various components of the rod 300 in FIG. 3B are understood to also apply to the corresponding components of the rod 300E in FIG. 13, except as described below.

The rod 300E differs from the rod 300 in that the rod 300E has a generally planar (e.g., flat) top surface 302E and the electrical contacts or connectors 312E are provided on the top surface 302E instead of a side surface as in the rod 300. The flat surface 302E and electrical contacts or connectors 312E on the top surface 302E allows conventional hangers H (see FIG. 14) to be hung on the rod 300E without the metal portion of such hanger H inadvertently touching the electrical contacts 312E and causing a short circuit.

Figure 15A:
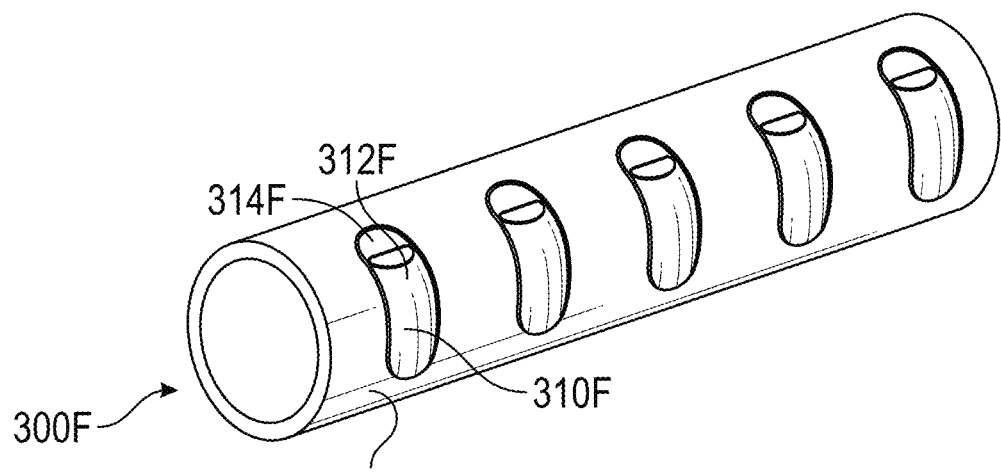
FIG. 15A is a schematic view of a hanging rod with one or more movable hooks for hanging a garment or hanger, with the hooks in the retracted position.
Figure 15B:
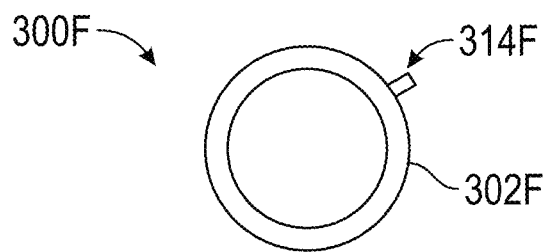
FIG. 15B is an end view of the hanging rod of FIG. 15A with the hooks in the retracted position.
Figure 15C:
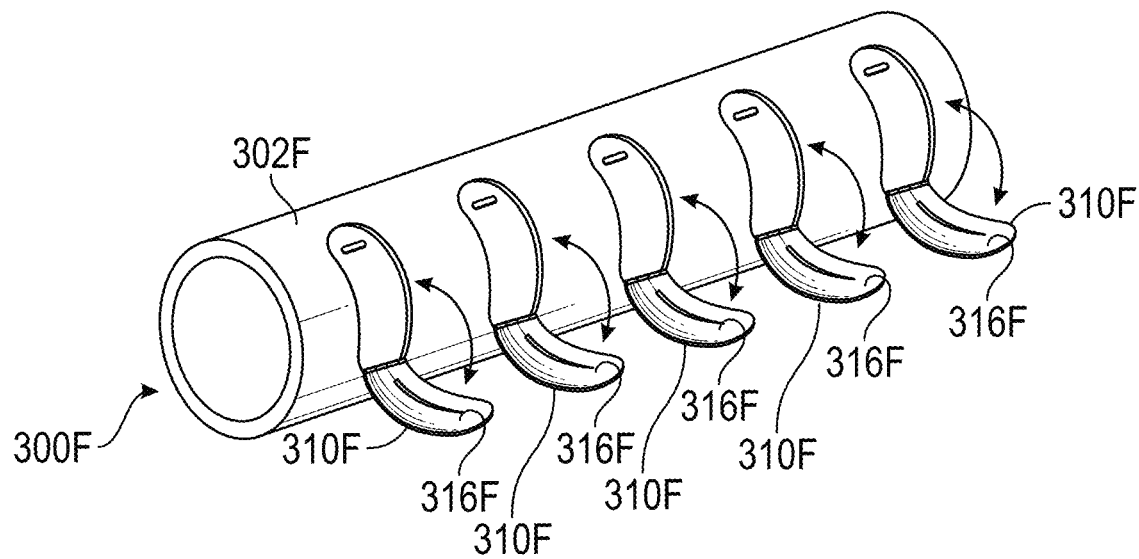
FIG. 15C is a schematic view of the hanging rod of FIG. 15A with the one or more movable hooks in the unfolded or extended position.

FIG. 15A shows a schematic perspective view of a hanging rod 300F with one or more (a plurality of) hooks 310F for hanging a garment or hanger, such as a hanger 100, 100'. FIG. 15A shows the rod 300F with the hooks 310F in the closed or retracted position. FIG. 15B shows an end view of the rod 300F. In one implementation, the rod 300F has a circular profile or cross-section. In another implementation, the rod 300F can have another suitable profile or cross-sectional shape, such as oval, rectangular, etc. FIG. 15C shows a perspective view of the rod 300F with the hooks 310F in the open or extended position.

The rod 300F can be similar to the rod 300 in FIG. 3B in that it can have an electrical cord and electrical plug that can be connected to a wall outlet to provide power to the rod 300F. The rod 300F has an outer surface 302F. As shown in FIGS. 15A-15B, when the hooks 310F are in the closed or retracted position, a surface 312F of the hooks 310F can be flush or retracted relative to the surface 302F of the rod 300F. The hooks 310F can have a handle or tab 314F that can be engaged (e.g., grabbed) by a user to move the hooks 310F into the extended or retracted position. As shown in FIG. 15C, which shows the hooks 310F in the extended position, the hooks 310F can have one or more electrical contacts 316F on an inner surface thereof that can contact electrical contacts on a hook of a hanger, such as hanger 100, 100F, to transfer power to the hanger 100, 100'.

Figure 16:
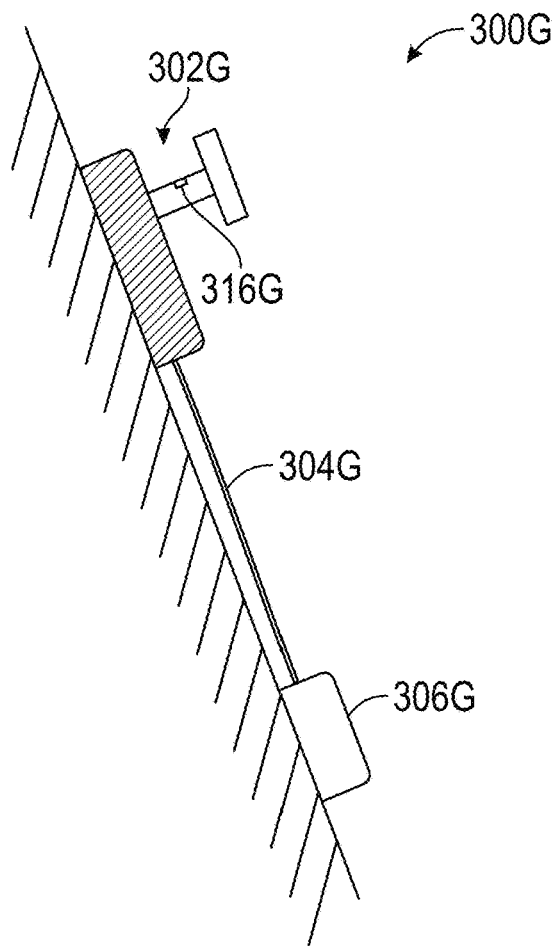
FIG. 16 is a schematic view of a wall mounted hook for hanging a garment or hanger.

FIG. 16 shows a side view of a hook 300G mounted on a wall. The hook 300G can have an electrical cord 304G that extends from the hook 300G to an electric plug 306G that can be connected to a wall outlet to provide power to a hook member 302G of the hook 300G. In one implementation, the hook member 302G has one or more electrical contacts 316G that can contact one or more electrical contacts on a hook of a hanger, such as the hanger 100, 100', to transfer power to the hanger 100, 100'.

Figure 17:
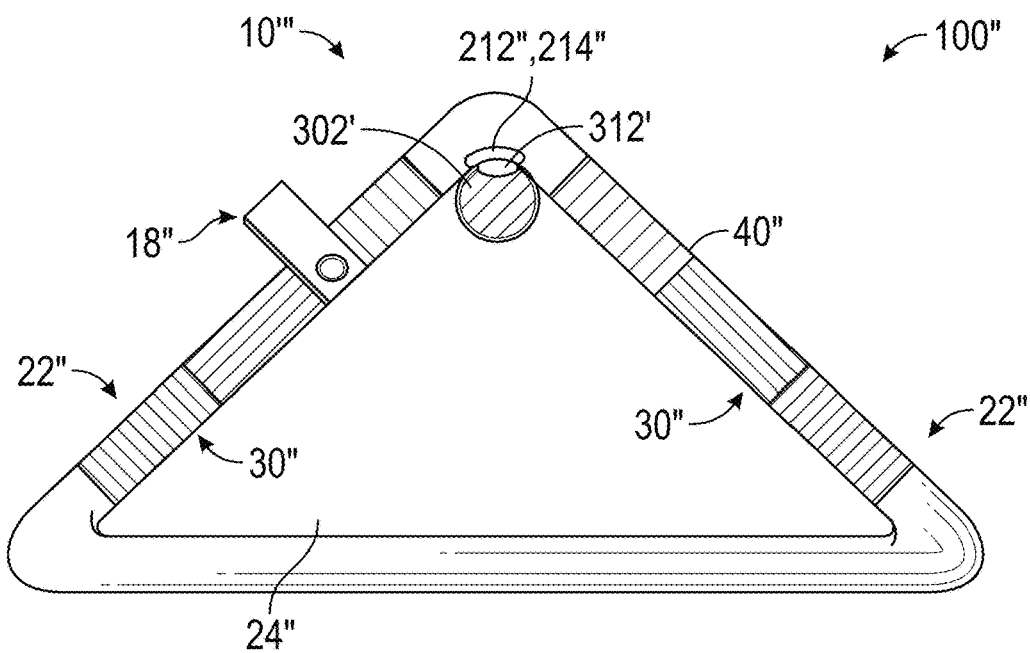
FIG. 17 is a schematic view of a hanger mounted on a hanging rod.

FIG. 17 shows a schematic (cross-sectional) view of a hanger 100" (e.g., a travel hanger) that can be hung on the rod 300' (shown in cross-section). The hanger 100" has a generally triangular shape with shoulders 22" and defines an opening 24" through which trousers or pants can be hung. The apex of the hanger 100" provides a hook 100'" to position the hanger 100" on the rod 300'. The hook 100'" has electrical contacts 212", 214" that can contact the electrical contacts or connectors 312' of the rod 300'. The outer surface 302' of the rod 300' can be circular; other suitable shapes are possible. The hanger 100" has a latch 18" movable between an open position to allow the hanger 100" to be hung about the rod 300' and a closed position to inhibit (e.g., prevent) the hanger 100" from decoupling from the rod 300'. Like the hanger 100, 100', the hanger 100" has power transmitters 30" and optionally has one or more batteries 40".

Advantageously, the hook 10A-10E, 10', 10" or connector 10F can be used instead of the hook 10 on the hanger 100, 100', 100" to transfer power to the hanger 100, 100', 100" (e.g., to one or both of the power transmitter(s) 30 and optional batteries 40 of the hanger 100, 100', 100") from the hanging rod 300, 300A, 300B, 300C, 300D, 300E, 300' via the electrical connectors or contacts 312A-312D, 314A-314D, 312E, 312' in the hanging rod 300, 300A, 300B, 300C, 300D, 300E, 300'. In one implementation, at least a portion of (e.g., an entire length of) the rod 300, 300A, 300B, 300C, 300D, 300E, 300' can have electrical connectors or contacts to provide power to a plurality of hangers 100, 100', 100" hung on the rod 300, 300A, 300B, 300C, 300D, 300E, 300'.

Figure 18:
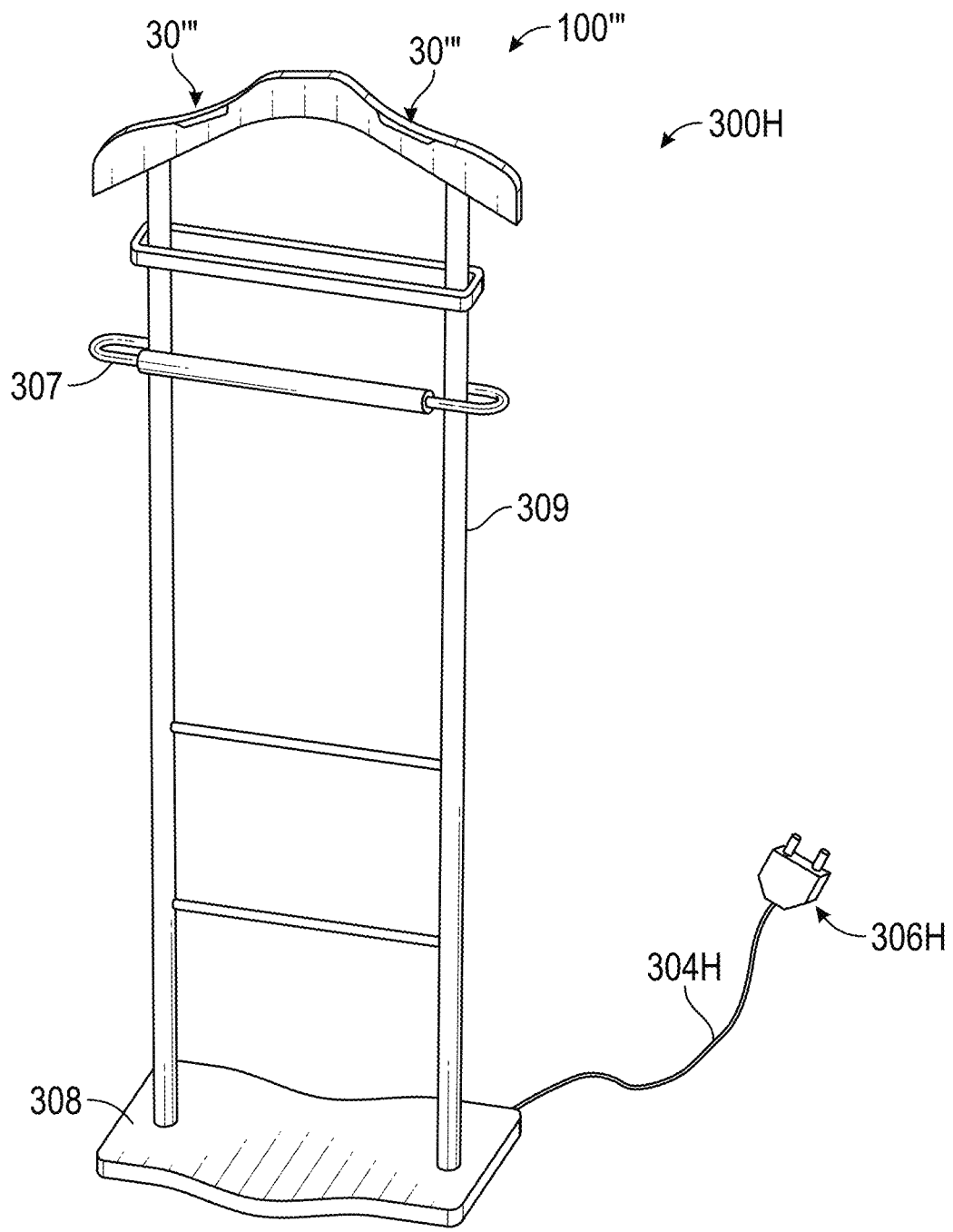
FIG. 18 is a schematic view of a stand with a hanger.

FIG. 18 shows a schematic perspective view of a stand 300H with a hanger 100'''. The stand 300H can have a base 308 on which support rods 309 are supported. The support rods 309 extend between the base 308 and the hanger 100'''. The stand 300H has a power cord 304H and electric plug 306H that can be connected to a wall power socket to provide power to one or more power transmitters 30'" in the hanger 100'''. The hanger 100'" can be similar to the hanger 100 and optionally have circuitry as shown in FIG. 3A. The stand 300H optionally has a separate hanging rod 307 for hanging trousers or pants. Alternatively, the stand 300H can be a coat stand with one or more hooks to hang garments with active temperature control (e.g. coats) thereon, where an electrical contact on the hooks of the coat stand can engage (e.g., contact) one or more electrical contacts on the garment (e.g., in a hanging tab or loop of the garment.

Figure 19:
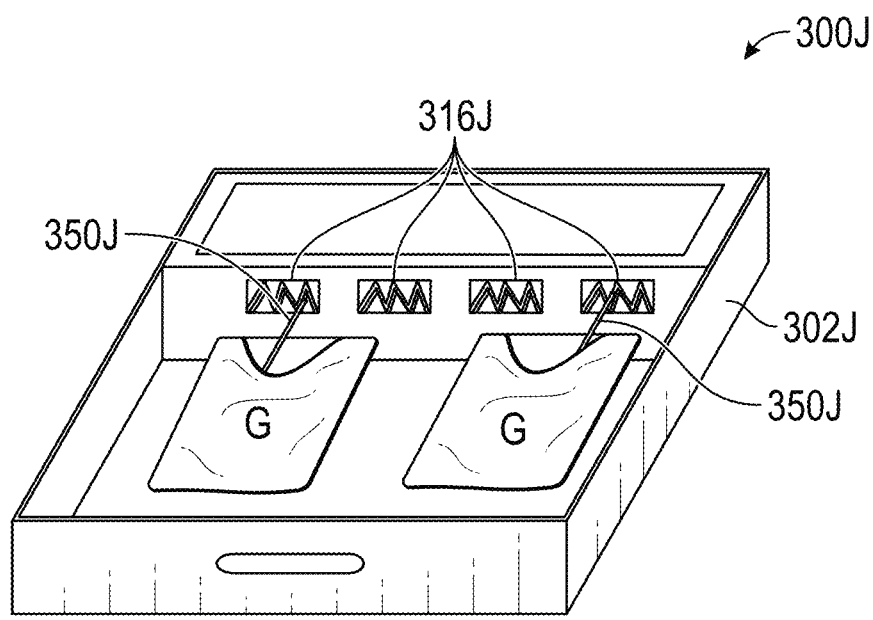
FIG. 19 is a schematic view of a drawer for a dresser or chest of drawers.

FIG. 19 is a schematic perspective view of a drawer 300J, such as for a dresser or chest of drawers. The drawer 300J bounds a space 302J in which one or more garments G with active temperature control (as further described below) can be folded and stored. The drawer 300J can have one or more electrical connectors or contacts 316J on a surface thereof (e.g., a rear drawer surface). The electrical connectors or contacts 316J can be USB ports that receive USB plugs of the cables 350J. Alternatively, electrical connector or contacts 316J can be magnetic induction power transmitter that transmit power (via induction) to magnetic contact of cables 350J that connect to the garment G. Power can be provided to the electrical connectors or contacts 316J via an electrical cord and electric plug or contact (not shown) that can be connected to power socket in a wall near the dresser, as discussed above. One or more cables 350J can be removably connected to one or both the electrical contacts or connectors 316J of the drawer 300J and one or more electrical contacts in the garment G, such as to charge batteries (e.g., rechargeable batteries) of the garment G for later use in powering the temperature control system of the garment G.

Figure 20:
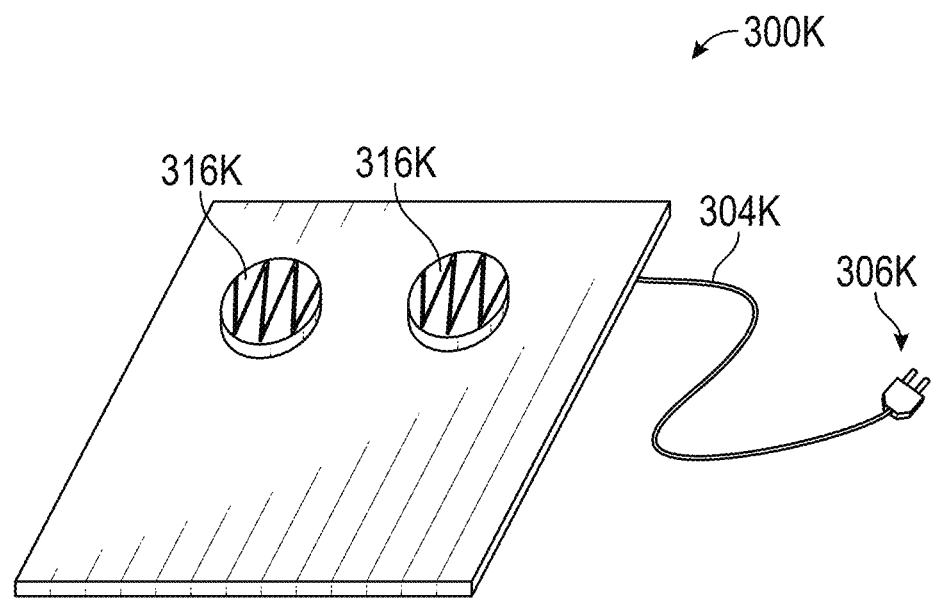
FIG. 20 is a schematic view of a power mat for use in a drawer for a dresser or chest of drawers.

FIG. 20 is a schematic perspective view of a power mat 300K that can be removably inserted into, for example, a preexisting drawer (of a dresser or chest of drawers). The power mat 300K can have an electrical cord 304K and electric plug 306K to connect to wall power to provider power to one or more electrical contacts 316K of the power mat 300K. One or more garments G with active temperature control can be placed on the power mat 300K (e.g., and in the drawer of the dresser) so that electrical contacts in the garment G are electrically connected to the electrical contacts 316K (e.g., via one or more cables, such as cables 350J) to provide power from the power mat 300K to one or more batteries of the garment G to charge them for later use of the garment G with active temperature control.

Figure 21:
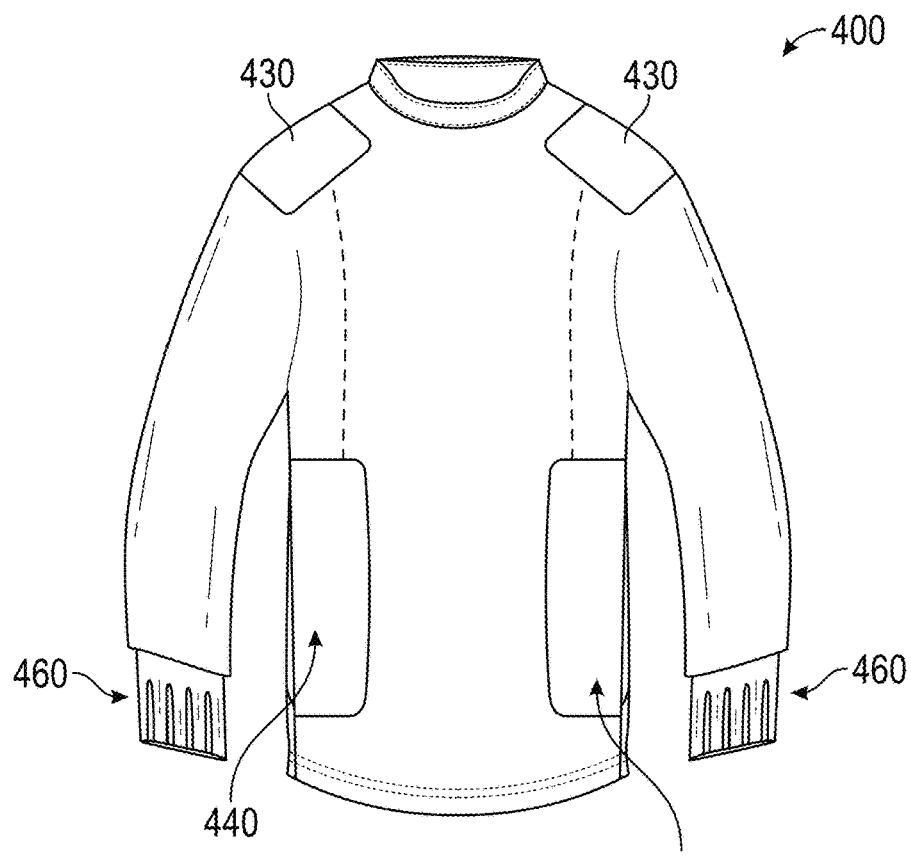
FIG. 21 is a schematic view of a garment (e.g., shirt) with active temperature control.

FIG. 21 shows a garment 400 (e.g., shirt) with active temperature control. The garment 400 has one or more power receivers 430 in shoulder portions of the garment 400, one or more batteries 440, which can be housed in one or more pockets (e.g., housed in a plurality of pockets) of the garment 400, circuitry 450 (e.g., control circuitry) and one or more heating elements, as further discussed below, the circuitry 450 can control delivery of power from the one or more batteries 440 to the one or more heating elements to selectively adjust a temperature of at least a portion of the garment. The garment 400 can optionally include one or more power transmitters 460, for example in sleeves of the garment 400, that can connect to accessories (e.g., gloves, ear warmer, as discussed further below) to allow transfer of power to the accessories.

In one implementation, the one or more batteries 440 are rechargeable, for example, via power delivered via the power receiver(s) 430. In one implementation, the one or more batteries 440 are permanently housed in the garment 400 (e.g., the batteries 440 are not removable). The batteries 440 can be housed (e.g. encased) in a phase change material (e.g., in a case housing the batteries 440) that can absorb the heat and/or impact when the garment 400 is washed in a washing machine and dried in a dryer. In another implementation, the one or more batteries 440 are removable for charging. For example, the one or more batteries can have electrical contacts that contact electrical contacts in the garment 440 to electrically connect the batteries with one or more of the power receiver(s) 430, circuitry 450 and one or more heating elements. Once removed from the garment 400, the batteries 440 can be charged using a charging module (e.g., charging module connected to wall power) so that electrical contacts of the batteries 440 contact electrical contacts of the charging module. Also, once the batteries are removed from the garment 400, the garment can be washed (e.g., using a washing machine and dryer). Advantageously, the circuitry and electrical connections between the electrical wires and circuitry as well as battery contacts can be water-tight (e.g., using epoxy potting) to inhibit (e.g., prevent) damage to electronics (e.g., circuitry 450, power receiver(s) 430, etc.) when the garment is exposed to water (e.g., in washing machine).

Figure 22:
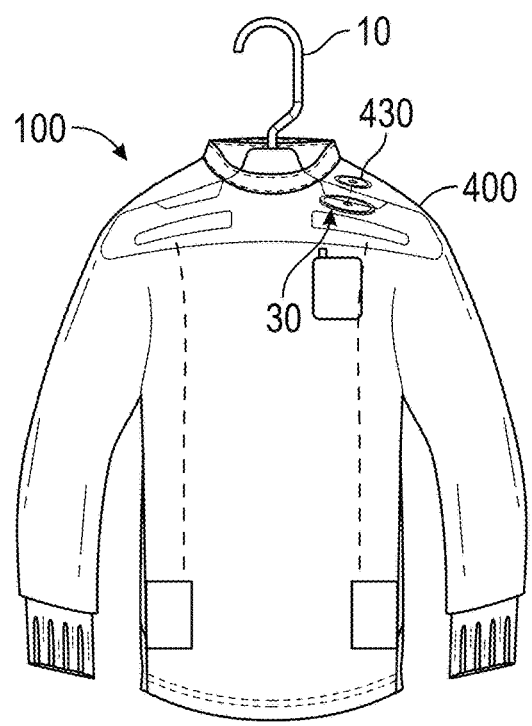
FIG. 22 is a schematic view of a garment (e.g., shirt) with active temperature control hung on a hanger.

With reference to FIG. 22, the one or more power receivers 430 in the garment 400 can receive power from the one or more power transmitters 30 in the hanger 100, 100' (e.g., via the battery 40 in the hanger 100, 100' and/or directly via power transmitted from the rod on which the hanger is hung). In one implementation, the power transmitter(s) 30 in the hanger 100, 100' and power receiver(s) 430 in the garment 400 can be induction coils so that power is transferred via induction. One of the garment 400 and hanger 100, 100' can have magnets and the other of the garment 400 and hanger 100, 100' can have a metal component or a magnet of different polarity to facilitate alignment of the power transmitter(s) 30 and power receiver(s) 430 to allow for efficient power transfer. In another implementation, the power transmitter(s) 30 and power receiver(s) 430 in the garment 400 provide a galvanic electrical connection via electrical contacts in the transmitter(s) 30 and receiver(s) 430.

Figure 23:
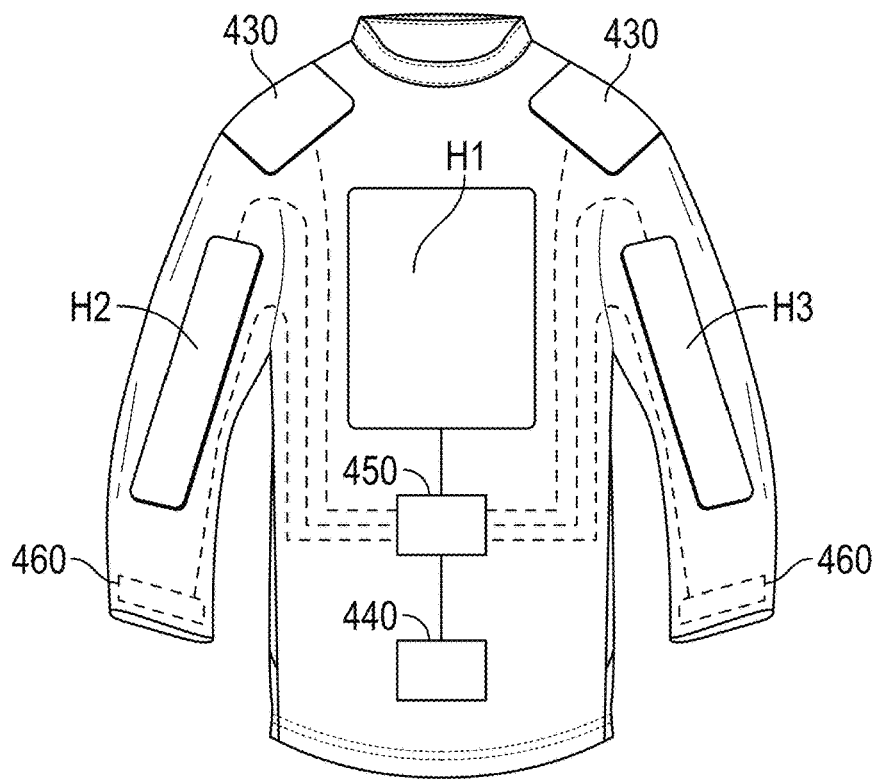
FIG. 23 is a schematic diagram of electronics in a garment (e.g., shirt) with active temperature control.

FIG. 23 shows a schematic diagram of electronics in the garment 400. The garment 400 includes one or more (e.g., a pair of) power receivers 430 proximate shoulder portions of the garment 400, one or more batteries 440 and circuitry 450 (e.g., control circuitry). The garment 400 also includes one or more heating elements distributed throughout the garment, as described herein. The one or more heating elements can include one or more heating elements H1 in a torso portion of the garment 400, one or more heating elements H2 in a left sleeve portion of the garment 400 and one or more heating elements H3 in a right sleeve portion of the garment 400. Additional heating elements can be provided in other portions of the garment 400. The one or more heating elements 400 can be connected (e.g., with electrical lines) to one or both of the circuitry 450 and one or more batteries 440. The power receivers 430 can connect to the circuitry 430.

The one or more heating elements in the garment 400, such as one or more heating elements H1, H2, H3 can in one implementation be heater wire woven into fabric material of garment 400. In another implementation, the one or more heating elements H1, H2, H3 can be metal etched heater pattern on the fabric material of the garment 400. In another implementation, the one or more heating elements H1, H2, H3 can be formed by electroplating directly on the fabric of the garment 400. In another implementation, the one or more heating elements H1, H2, H3 can include a heat spreader to facilitate a uniform temperature feel by the user during actuation of the heating elements (e.g., inhibit or prevent hot spots). In one implementation, the heat spreader can be aluminum woven mesh material. In another implementation, the heat spreader can be graphite. The heating elements and/or spreader can have other suitable configurations or materials.

Figure 24:
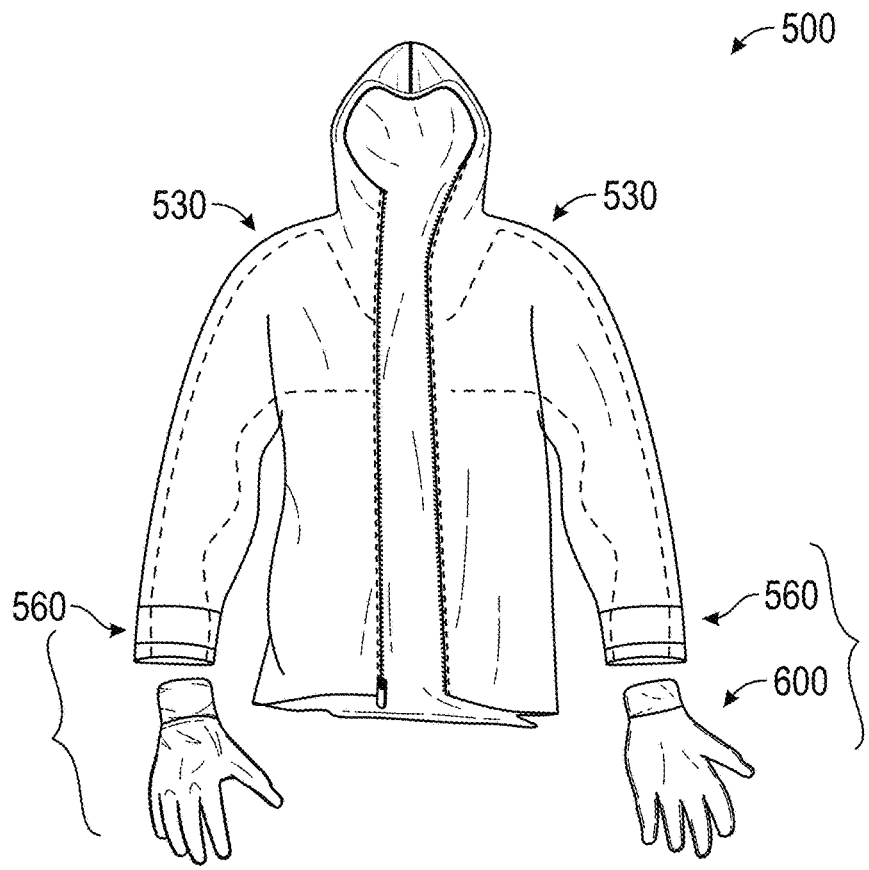
FIG. 24 is a schematic view of a garment (e.g., jacket) with active temperature control and pair of gloves.

FIG. 24 shows a garment 500 (e.g., jacket) with active temperature control. The garment 500 is similar to the garment 400 in FIG. 21. Thus, references numerals used to designate the various components of the garment 500 are identical to those used for identifying the corresponding components of the garment 400 in FIG. 21, except that the numerical identifier begins with a "5" instead of a "4". Therefore, the structure and description for the various components of the garment 400 in FIG. 21 are understood to also apply to the corresponding components of the garment 500 in FIG. 24, except as described below.

The garment 500 differs from the garment 400 in that it is a jacket and includes a hood. Optionally, the garment 500 can be made of different material (e.g., water resistant material). The garment 500 has power receiver(s) in the shoulder portions of the garment 500 and power transmitter(s) 560 in wrist portions of the sleeves of the garment 500. FIG. 24 shows accessories (e.g., gloves) 600 that can have one or more heating elements and can receive power from the power transmitter(s) 560, as further discussed below.

Figure 25:
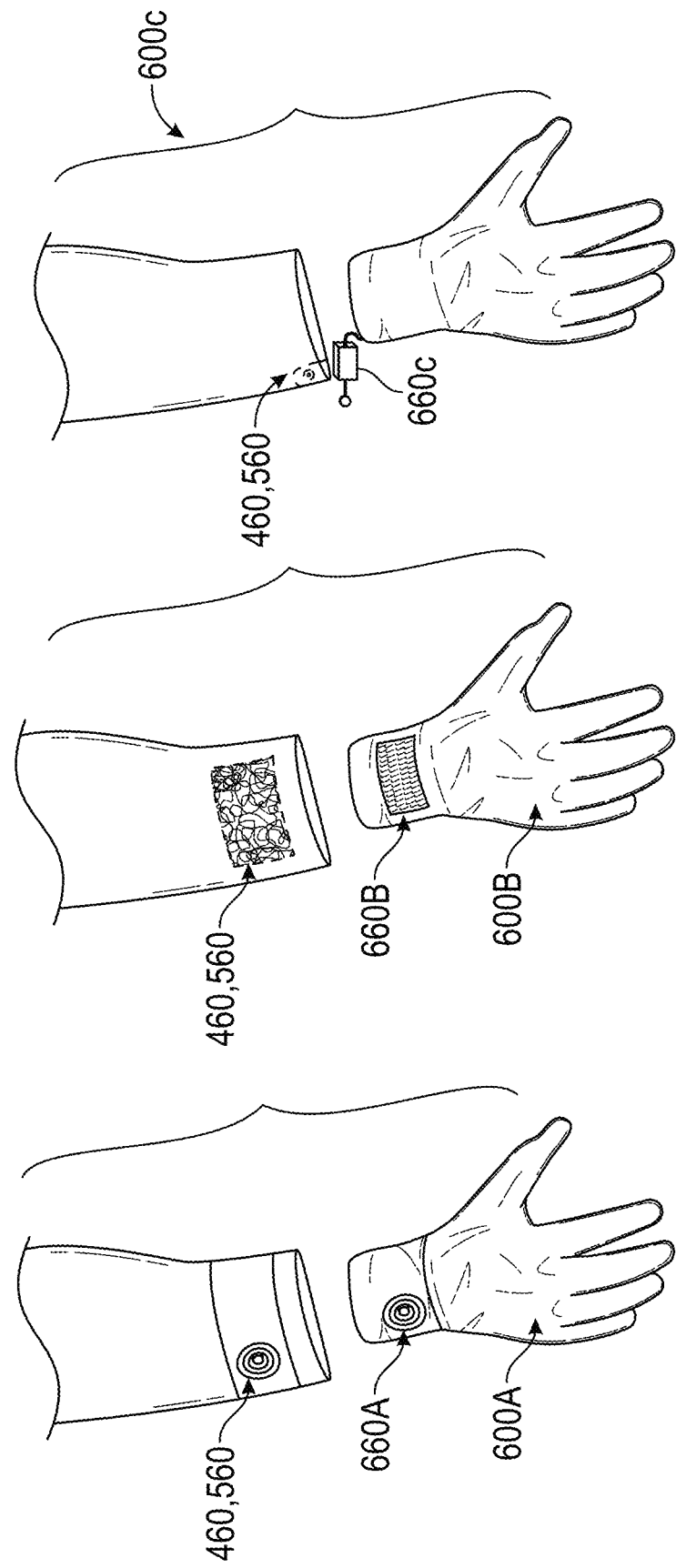
FIG. 25A is a schematic view of a glove with active temperature control and power transfer connection for connecting with a sleeve of a garment.
FIG. 25B is a schematic view of a glove with active temperature control and power transfer connection for connecting with a sleeve of a garment.
FIG. 25C is a schematic view of a glove with active temperature control and power transfer connection for connecting with a sleeve of a garment.

FIG. 25A shows a schematic view of a glove 600A with one or more power receivers 660A that can receive power from one or more power transmitters 460, 560 in a garment 400, 500. The power receiver(s) 660A and power transmitter(s) 460, 560 can be induction coils so that power is transmitted to the glove 600A via induction to power one or more heating elements in the glove 600. One of the garment 400, 500 and glove 600A can have magnets and the other of the garment 400, 500 and glove 600A can have a metal component or a magnet of different polarity to facilitate alignment of the power transmitter(s) 460, 560 and power receiver(s) 660 to allow for efficient power transfer to the glove 600A.

FIG. 25B shows a schematic view of a glove 600B with one or more power receivers 660B that can receive power from one or more power transmitters 460, 560 in a garment 400, 500. The power receiver(s) 660B and power transmitter(s) 460, 560 can be a conductive hoop and loop (e.g., VELCRO®) material so that power is transmitted to the glove 600B via a direct connection to power one or more heating elements in the glove 600.

FIG. 25C shows a schematic view of a glove 600C with one or more power receivers 660C that can receive power from one or more power transmitters 460, 560 in a garment 400, 500. The power receiver(s) 660C can be an electric cable, and the power transmitter 460, 560 includes a connector to which the electric cable is coupled so that power is transmitted to the glove 600C via a direct connection to power one or more heating elements in the glove 600.

Figure 26:
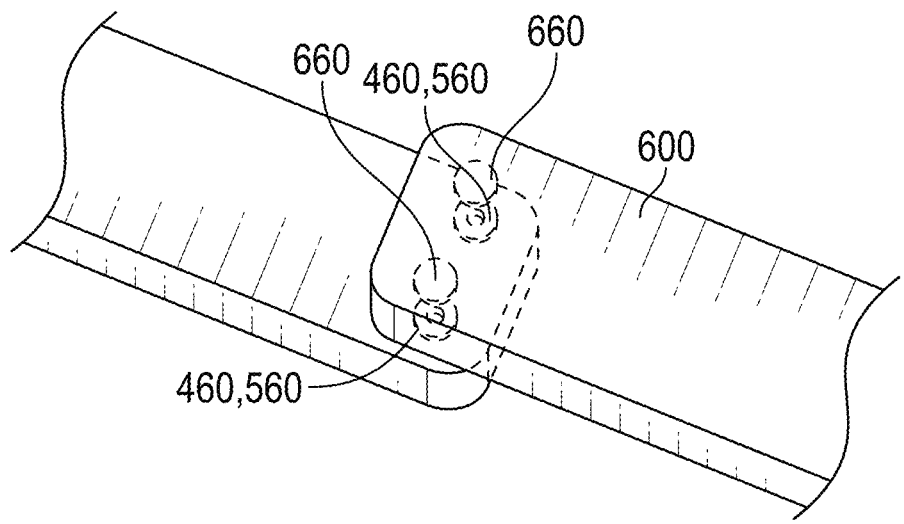
FIG. 26 is a schematic view of a power transfer connection for use in garments or accessories with active temperature control.

FIG. 26 is a schematic view of a power transfer connection between power transmitter(s) 460, 560 in a garment and power receiver(s) 660 in an accessory (e.g., glove). In the illustrated embodiment, the power transmitter(s) 460, 560 and power receiver(s) 660 are snaps that can removably couple to each other to effect the electrical connection to transfer power to the accessory (e.g., glove).

Figure 27:
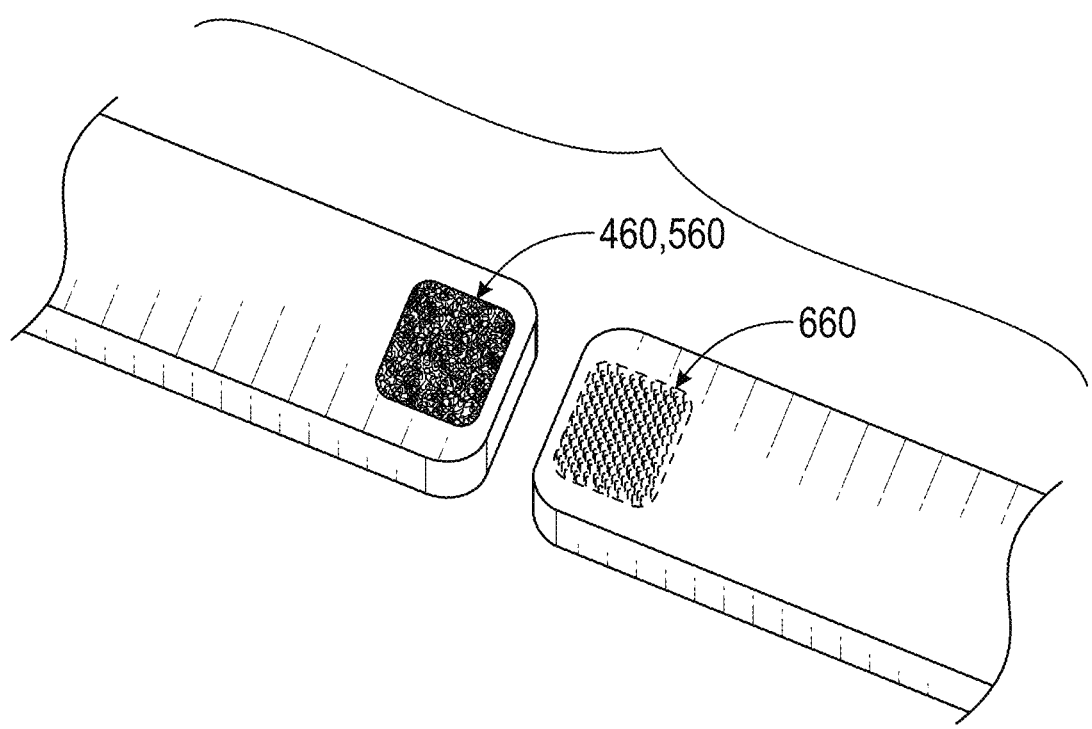
FIG. 27 is a schematic view of a power transfer connection for use in garments or accessories with active temperature control.

FIG. 27 is a schematic view of a power transfer connection between power transmitter(s) 460, 560 in a garment and power receiver(s) 660 in an accessory (e.g., glove). In the illustrated embodiment, the power transmitter(s) 460, 560 and power receiver(s) 660 are conductive hoop and loop connectors (e.g., VELCRO®) that can removably couple to each other to effect the electrical connection to transfer power to the accessory (e.g., glove).

Figure 28:
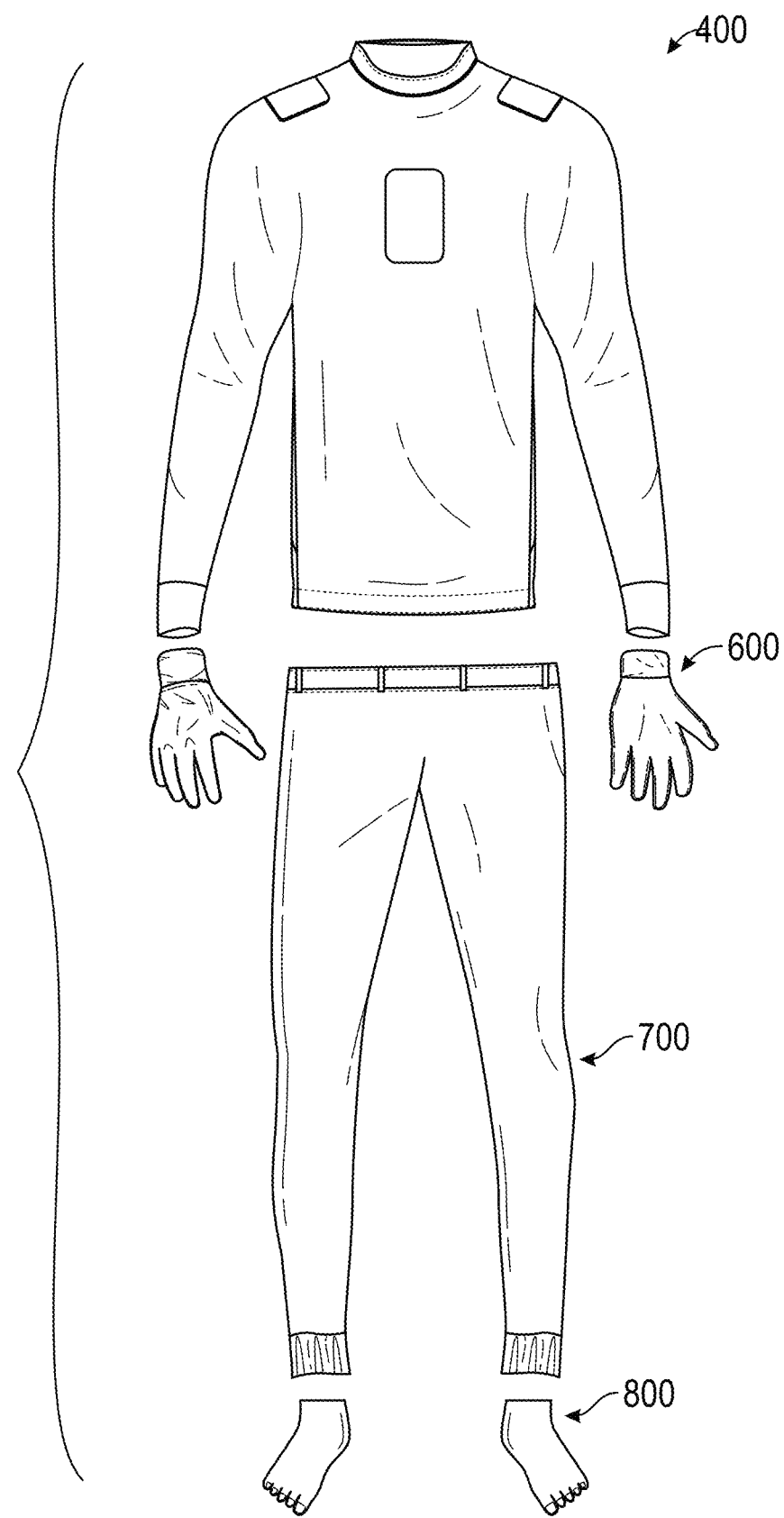
FIG. 28 is a schematic view of a sportswear outfit (e.g., top, pants, gloves, socks) with active temperature control and power transfer connections for connecting them.

FIG. 28 is a schematic view of a sportswear outfit that includes a shirt or top 400, pants 700 and optionally includes gloves 600 and socks 800, all of which can have one or more heating elements and electronics to effect active temperature control. The gloves 600 can receive power from the top 400 in the manner discussed above. The pants 700 can optionally have their own power source (e.g., batteries, circuitry, etc.). In another implementation, the pants 700 can exclude batteries and have an electrical connection with the shirt 400 (e.g. via the waist of the pants 700 and bottom of the shirt 400) to facilitate power transmission from the shirt 400 to the pants 700. The socks 800 can have an electrical connection with the bottom end of the pants 700 to facilitate power transmission from the pants 700 to the socks 800.

Figure 29:
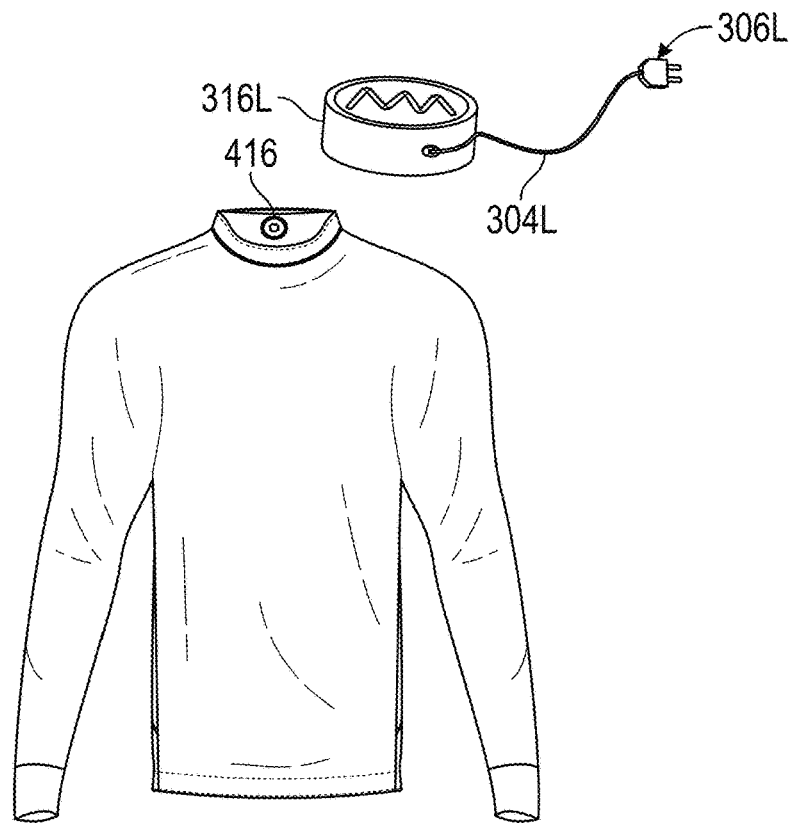
FIG. 29 is a schematic view of a garment (e.g., shirt) with an electric power receiver and an electric power transmitter connectable to the electric power transmitter.

FIG. 29 is a schematic view of a garment (e.g., shirt) G with an electric power receiver 416 that can be connected to an electric power transmitter 316L (e.g., to charge batteries of the garment G). The power transmitter 316L can have a power cord 304L and electric plug 304K that can be connected to a wall outlet.

Figure 30:
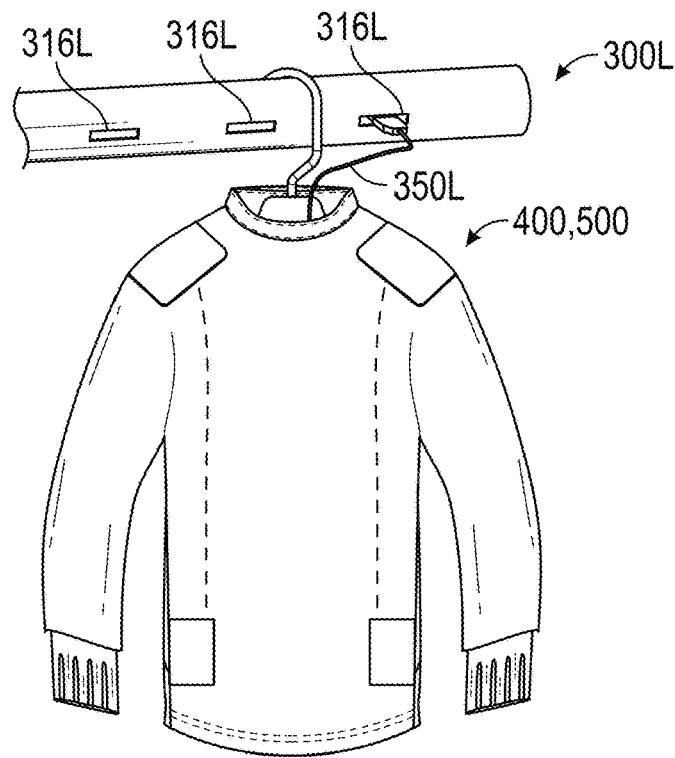
FIG. 30 is a schematic view of a garment (e.g., shirt) with active temperature control hung on a conventional hanger, which his hung on a hanging rod, the garment connected to the hanging rod via an electrical connector for power transfer to the garment.

FIG. 30 is a schematic view of the garment 400, 500 with active temperature control hung on a conventional hanger on a hanging rod 300L that has one or more connectors (e.g. USB connectors) 316L. An electric cable 350L can connect to the connectors 316L and to an electric contact in the garment 400, 500 to transfer power from the rod 300L to the garment 400, 500 (e.g., to the batteries of the garment 400, 500 to charge the batteries).

Figure 31:
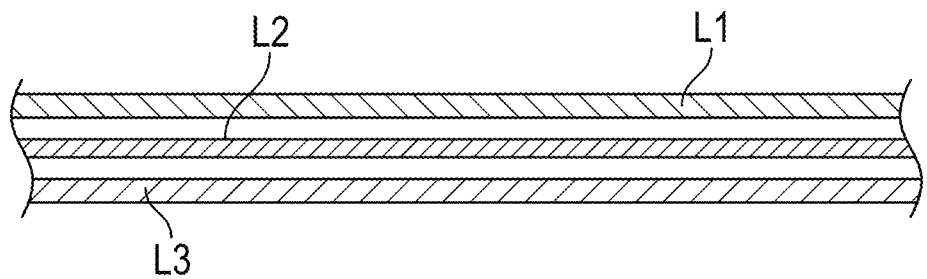
FIG. 31 is a schematic cross-sectional view of a portion of a garment with active temperature control.

FIG. 31 is a schematic cross-sectional view of a portion of the garment 400, 500, 700. The garment can optionally have a first layer L1 (e.g., outer layer) that can be made of an insulative or breathable fabric. The garment can have a second layer L2 that can include one or more heating elements, as discussed above. The one or more heating elements may be woven into the fabric. The garment can optionally have a third layer L3, which can optionally be insulative fabric or moisture wicking.

Figure 32A:
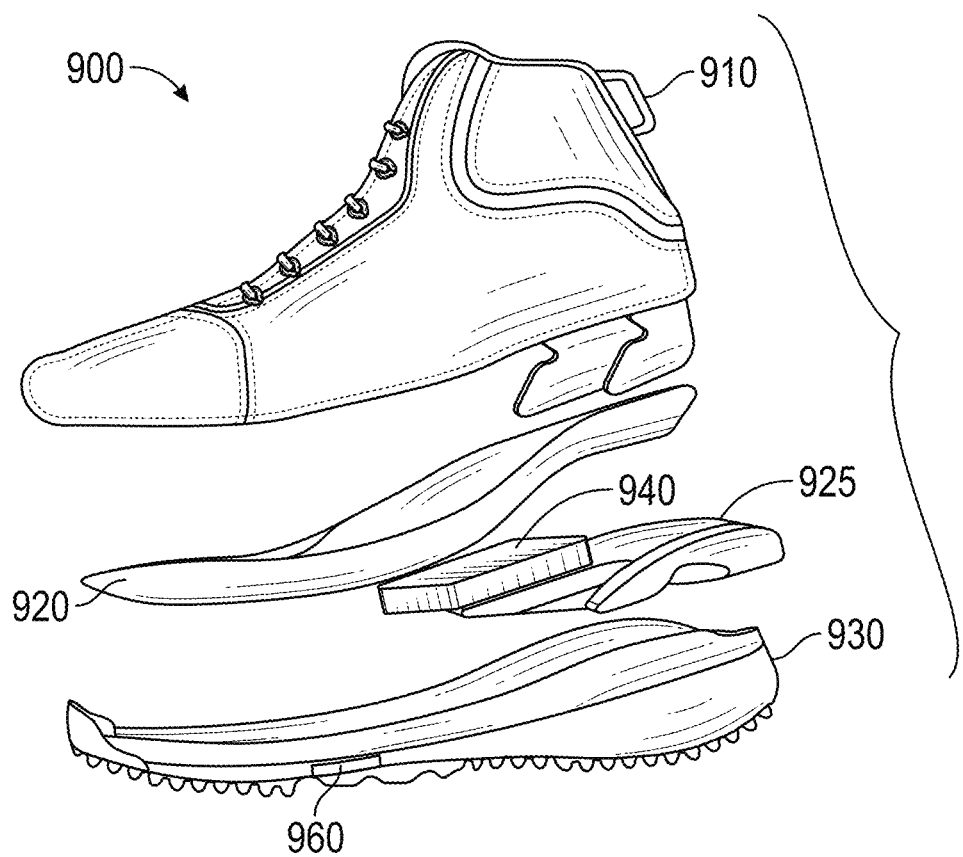
FIG. 32A is a schematic exploded view of footwear (a shoe) with active temperature control.
Figure 32B:
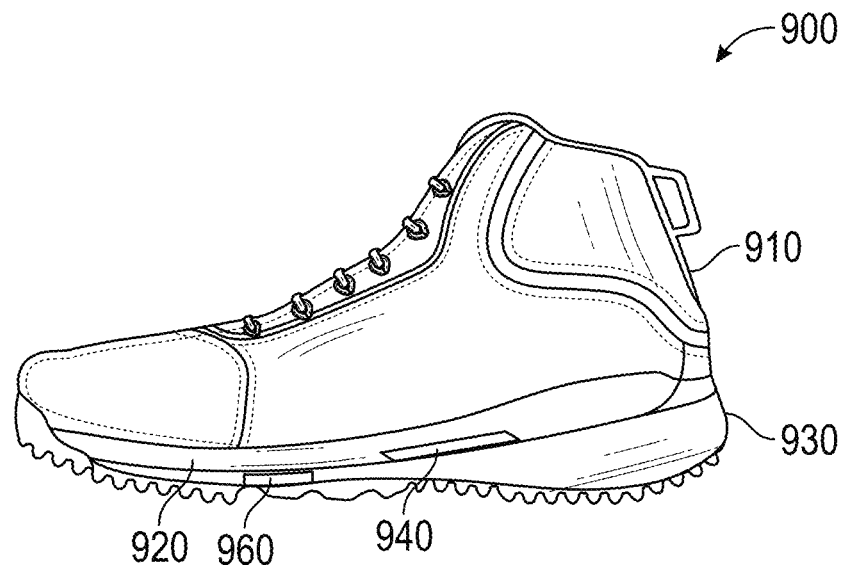
FIG. 32B is a schematic assembled view of the footwear (a shoe) of FIG. 32A.
Figure 32C:
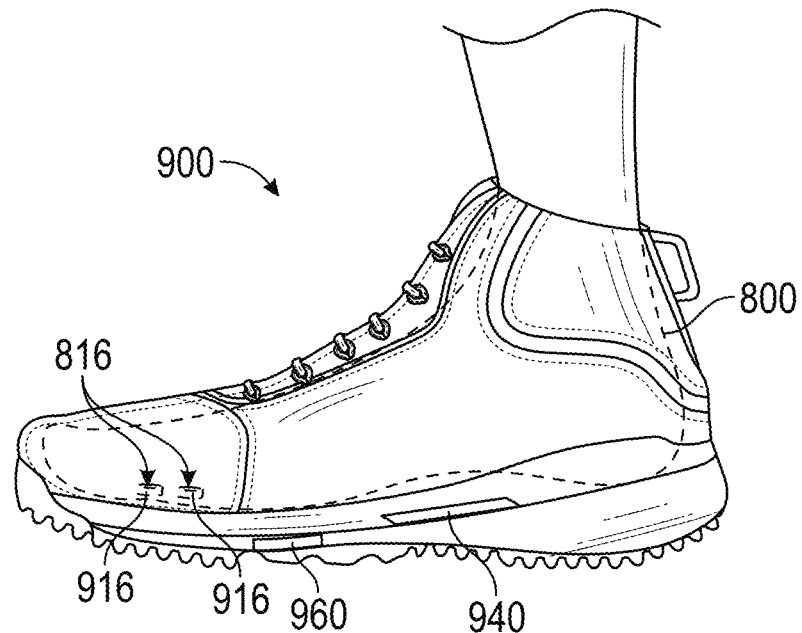
FIG. 32C is a schematic cross-sectional view of footwear (a shoe) with a sock with active temperature control.

FIGS. 32A-32C show footwear (a shoe) 900 with active temperature control. The shoe 900 has an upper 910, a sole 930, and insole 920, support padding 925 and one or more batteries 940. The shoe 900, though not shown, also has circuitry that electrically connects to the one or more batteries 940 and one or more heating elements actuatable (by the circuitry) to heat one or more surfaces of a foot wearing the shoe 900. In one implementation, the one or more heating elements are in the insole 920 and heats a sole of a human foot wearing the shoe 900. In another implementation, the one or more heating elements are in a sock 800. The sock 800 has one or more electrical contact 816 that contact one or more electrical contacts 916 in the shoe 900 to receive power from the batteries 940 in the shoe 900.

The batteries 940 in the shoe 900 can be charged via a power receiver in the shoe that receives power form a power transmitter (e.g., on a shoe rack on which the shoe 900 is placed). The power receiver in the shoe 900 can in one implementation be an induction coil that is aligned with an induction coil in the shoe rack to transfer power from the shoe rack to the shoe 900 (to charge the batteries 940). In another implementation, the power receiver in the shoe 900 is an electrical contact that contacts an electrical contact in the shoe rack to transfer power to the shoe 900 (e.g., to charge the batteries 940). In another implementation, the shoe 900 can have a USB port that can receive a connector of an electric cable, which can be connected to a wall power outlet to charge the batteries 940.

Figure 33:
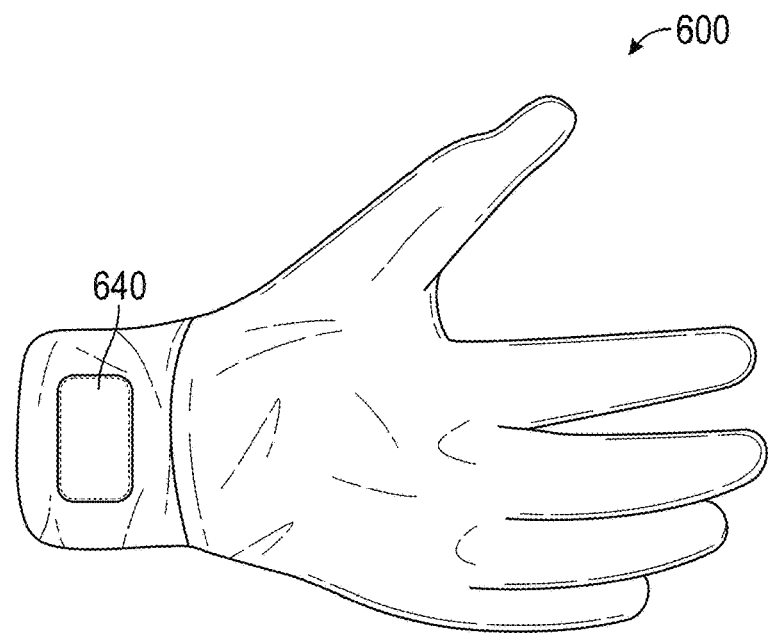
FIG. 33 is a schematic view of a glove with active temperature control.

FIG. 33 is a schematic view of a the glove 600. In this implementation, the glove 600 has one or more batteries 640 that power the one or more heating elements in the glove 600.

Figure 34:
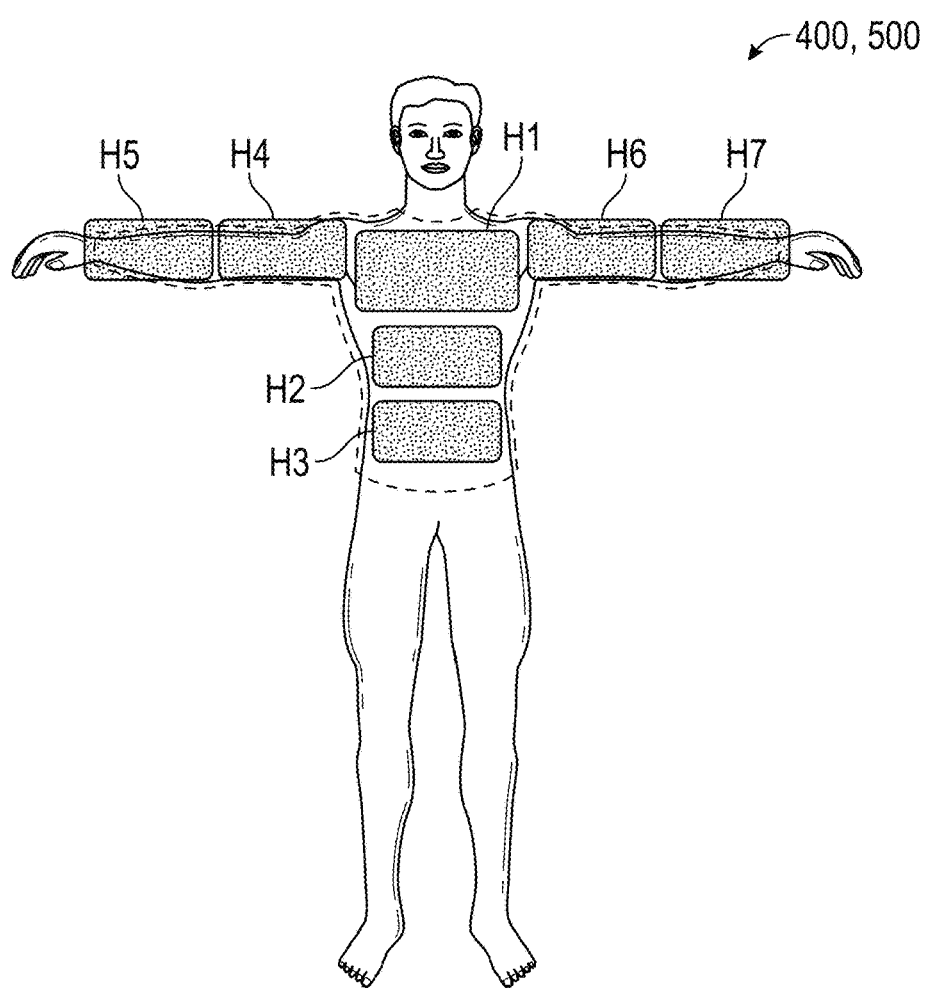
FIG. 34 is a schematic view of a garment with multiple heating areas worn by a user.
Figure 35:
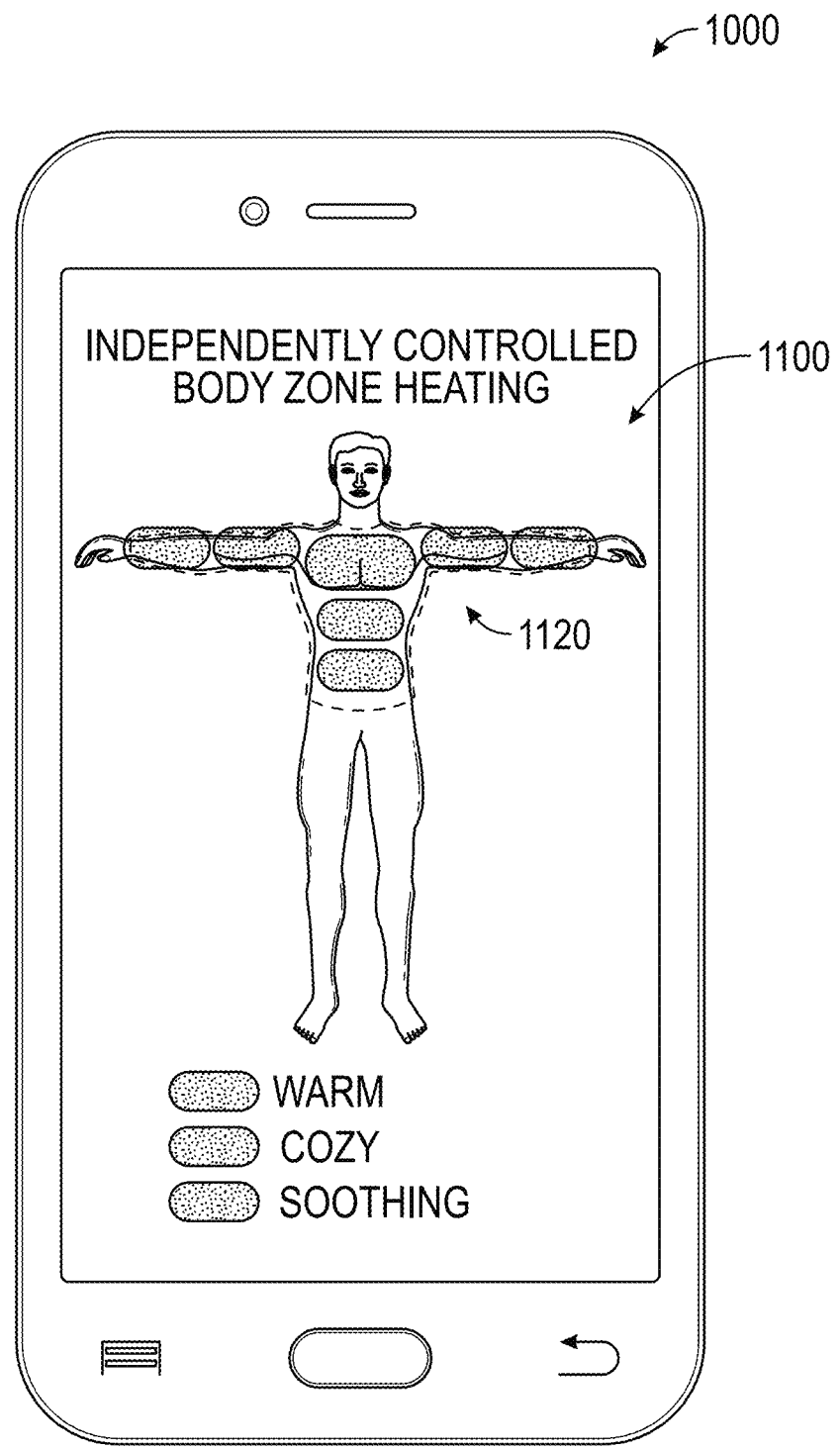
FIG. 35 is a graphical user interface on a remote electronic device (smartphone) for use in controlling an active temperature control system in a garment.

FIG. 34 shows a schematic view of a garment 400, 500, with one or more heating elements H1-H7. One or more heating elements H1 can be located in the upper chest portion, one or more heating elements H2 can be located in a back portion, one or more heating elements H3 can be located in an abdomen portion, one or more heating elements H4 can be located in an upper right arm portion, one or more heating elements H5 can be located in a lower right arm portion, one or more heating elements H6 can be located in an upper left arm portion, and one or more heating elements H7 can be located in a lower left arm portion of the garment 400, 500. Each of the heating elements H1-H7 can be selectively operated (by the circuitry 450, 550) to heat its associated portion of the user's body. In one implementation, one or more of the heating elements H1-H7 are independently operated of the rest of the heating elements H1-H7 (e.g., at different power or heating levels).

The operation of the one or more heating elements H1-H7 can be controlled via a user interface 1120 of an app 1100 on a remote electronic device (e.g., smartphone, tablet computer) 1000. The app 1100 displays on the graphical user interface or GUI 1120 a human body (e.g., human torso) and the user can select a portion of the garment 400, 500 to heat (e.g., by touching the portion of the human torso on the GUI 1120 associated with the one or more heating elements H1-H7 of the garment 400, 500) and heating level for it (e.g., high, medium, low; warm, cozy, soothing), such as by continuing to tap or press the portion of the human torso on the GUI 1120, causing the heating or power level of the one or more heating or cooling elements H1-H7 associated with the touched portion of the torso on the GUI 1120 to cycle through the heating or power level setting options. A user can optionally press or touch on an icon on the user interface 1200 that corresponds to one of the heating elements H1-H7 to change the operating level of the heating element H1-H7. In one implementation, the heating level of the heating elements H1-H7 can be varied between a variety of preset power/heating levels (e.g., high, medium, low; or warm, cozy, soothing). The user selection is communicated wirelessly to the circuitry 450, 550 in the garment 400, 500 (via a wireless receiver or transceiver in the circuitry 450, 550). Accordingly, a user can use the app 1100 to set different heating levels for different portions of the garment 400, 500 to provide a personalized climate control. The app 1100 can learn user habits (e.g., time of workouts) and send instructions to the circuitry 450, 550 in the garment 400, 500 to preheat the garment before it is worn by the user for physical activity. The user can optionally also add a custom workout schedule via the app 1100, and the app 1100 can communicate instructions to the garment 400, 500 (via the circuitry 450, 550) to have the garment 400, 500 automatically pre-heat before the user puts the garment 400, 500 on.

In another implementation, the heating elements H1-H7 can controlled via gestures (e.g., rubbing portion of the heating elements H1-H7) and capacitive touch sensors or accelerometer in the garment associated with each heating element H1-H7 can sense the gesture and communicate a signal to the circuitry 450, 550 to operate the heating elements H1-H7 (e.g., turn on, turn off, adjust a temperature of the heating elements H1-H7). In another implementation, the heating elements H1-H7 can be controlled via voice control or any wearable electronic device that has wireless communication capability (e.g., an Apple® watch). In another implementation, the circuitry 450, 550 can communicate wirelessly with a weather app (e.g., in the smartphone 1000) and automatically control the heating elements H1-H7 based on the forecast ambient temperature.

Optionally, a button on the garment 400, 500, 700 or footwear 900 can be used to pair it with the smartphone 1000 to allow control of the heating elements H1-H7 via the app 1100 on the smartphone 1000.

Figure 36:
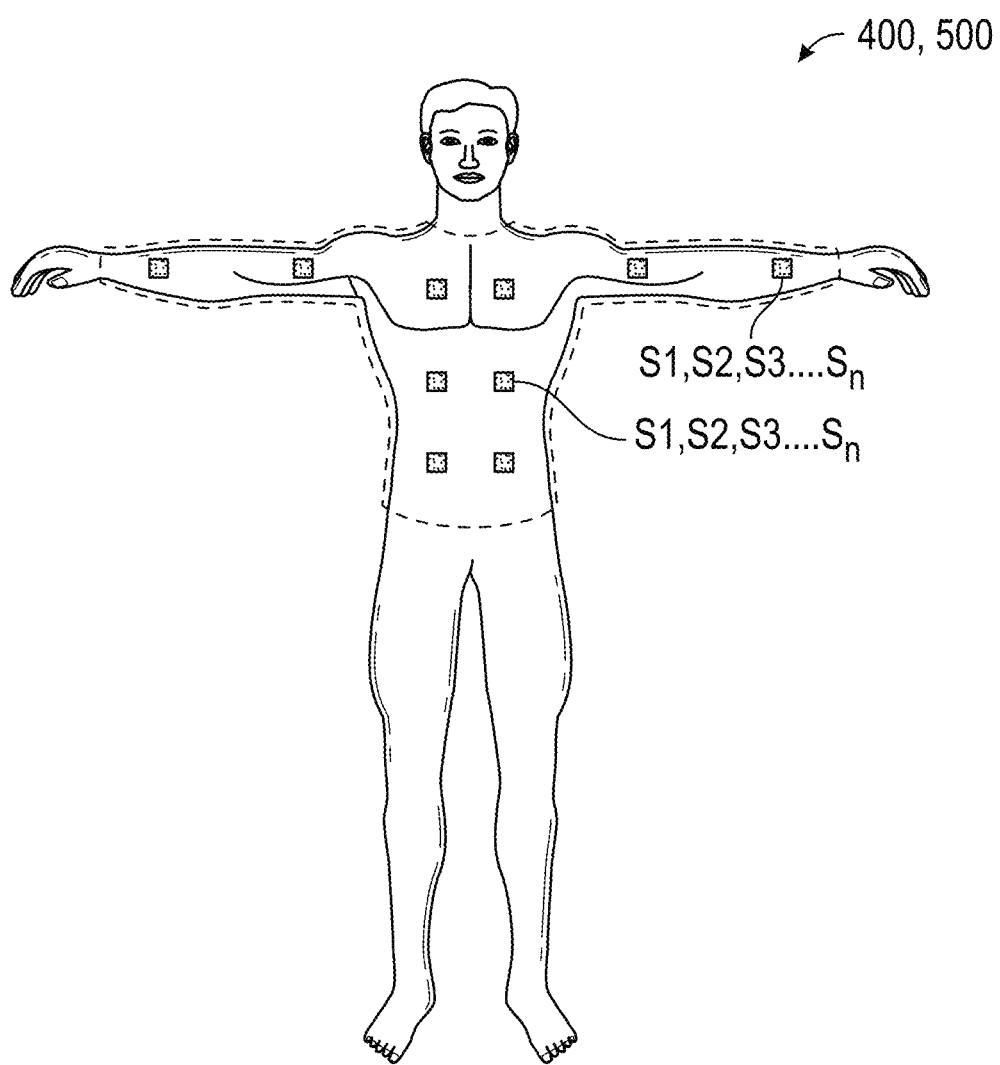
FIG. 36 is a schematic view of a garment with multiple sensors worn by user, the garment having active temperature control.

With reference to FIG. 36, the garment 400, 500, 700 can have one or more (e.g., a plurality of) sensors S1, S2, S3 ... Sn, which can include temperature sensors (that sense user body temperature, ambient temperature), humidity sensors, heart rate sensors, oxygen level sensors, etc. The sensors S1, S2, S3 ... Sn can monitor such parameters continuously and communicate with the circuitry 450, 550, and the circuitry 450, 550 can control the operation of the heating elements H1-H7 based on the sensed information (e.g., to auto calibrate heating applied at each location of the garment by the heating elements H1-H7, for example based on sensed body temperature, based on sensed ambient temperature or humidity, etc.). For example, the sensors S1, S2, S3 ... Sn can sense when the desired temperature has been reached and can automatically turn off one or more of the heating elements H1-H7. The garment 400, 500 can provide dynamic adjustments of heating levels by the heating elements H1-H7 based on ambient temperature (sensed by temperature sensors as discussed further herein) and desired user selected comfort level.

Though the garment 400, 500, 700, accessories 600 or footwear 900 described above include heating elements H1-H7, which can be resistive heating elements, they can instead include heating or cooling elements (e.g., thermoelectric elements or Peltier elements that can be operated to provide heating or cooling to areas of the user's body associated with the garment or footwear location that has the Peltier element or thermoelectric module).

Figure 37:
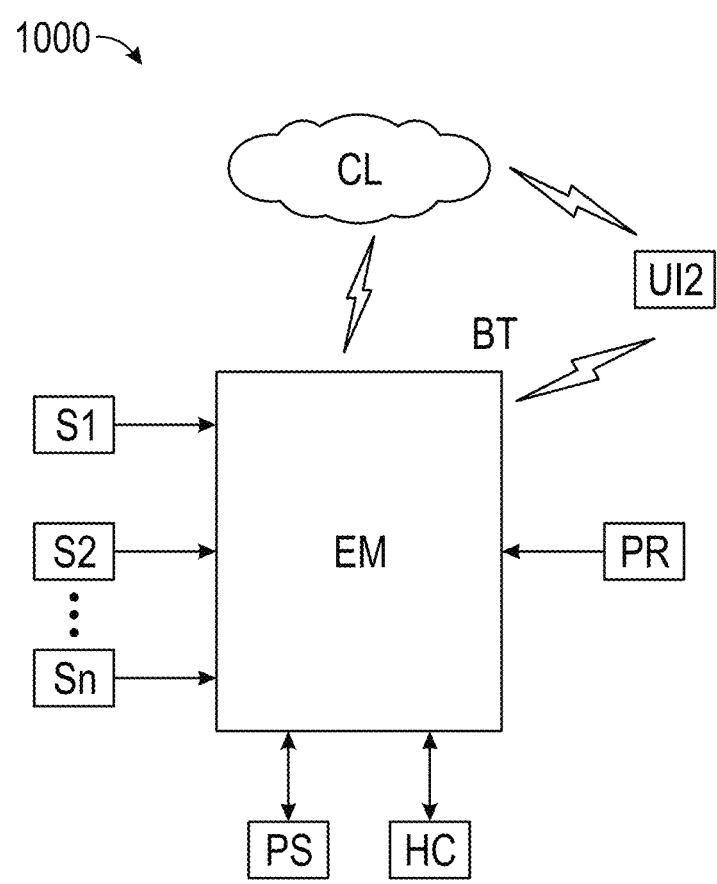
FIG. 37 is a schematic block diagram showing electronics in a garment (shirt, jacket, pants), accessory (gloves) or footwear (socks, shoes) with active temperature control.

FIG. 37 is a schematic block diagram showing electronics in a garment 400, 500, 700, accessory 600 or footwear 900 with active temperature control. In the illustrated embodiment, circuitry EM (e.g., circuitry 450, 550) can receive sensed information from one or more sensors S1-Sn (e.g., temperature sensors, humidity sensors, heart rate sensors, oxygen level sensors). A power receiver PR (e.g., power receiver(s) 430, 530, 660A, 660B, 660C, 960) can communicate with (e.g., be electrically connected to) the circuitry EM to transmit power from a power source (e.g., hanger 100, 100', 100", rod 300, 300A, 300B, 300C, 300D, 300E, 300', hook 300F, 300G, stand 300H or shoe rack) to the circuitry EM. The circuitry EM can receive information from and/or transmit information (e.g., instructions) to one or more heating or cooling elements HC, such as heating elements H1-H7, to operate each of the heating or cooling elements H1-H7 in a heating mode and/or in a cooling mode (when the heating element is a Peltier element), turn off, turn on, vary power output of, etc. and optionally to one or more power storage devices PS (e.g., batteries 440, 540, 640) such as to charge the batteries or manage the power provided by the batteries to the one or more heating or cooling elements H1-H7.

Optionally, the circuitry EM can include a wireless transmitter, receiver and/or transceiver to communicate with, e.g., transmit information, such as sensed temperature, humidity, heart rate, oxygen level to and receive information, such as user instructions, from an electronic device ED (e.g., a mobile electronic device such as a mobile phone or smartphone, PDA, tablet computer, laptop computer, electronic watch, a desktop computer, remote server), or the cloud CL (e.g., a cloud-based data storage system) via a wireless communication system such as WiFi and Bluetooth BT, or using a cell radio. The electronic device ED (such as electronic device 1000) can have a user interface UI2 (such as graphical user interface or GUI 1100), that can display information associated with the operation of the container system, and that can receive information (e.g., instructions) from a user and communicate said information to the garment 400, 500, 700, accessories (gloves) 600 or footwear 900.

Optionally, the circuitry EM can communicate (e.g., wirelessly) information to a remote location (e.g., cloud based data storage system, remote computer, remote server, mobile electronic device such as a smartphone or tablet computer or laptop or desktop computer) and/or to the individual wearing the garment 400, 500, 700, accessories 600 or footwear 900, such as a temperature history, heart rate history, oxygen level history to provide a record for the user (e.g., during exercise intervals, trainings, such as for a marathon or triathlon) that can be used to evaluate user performance.

Additional Embodiments

In embodiments of the present invention, a garment or footwear with active temperature control or hanger assembly for a garment with active temperature control may be in accordance with any of the following clauses Clause 1: A garment with active temperature control, comprising:
 one or more heating or cooling elements;
 one or more batteries;
 one or more power receivers; and
 circuitry, the circuitry configured to control the delivery of power to the one or more heating or cooling elements to heat or cool one or more portions of the garment associated with the one or more heating or cooling elements.

Clause 2: The garment of clause 1, wherein the garment is a shirt or jacket.

Clause 3: The garment of any preceding clause, wherein the one or more heating or cooling elements are woven into the fabric of the garment or disposed between two layers of fabric.

Clause 4: The garment of any preceding clause, wherein the one or more batteries are removable, allowing the garment to be washed without the batteries.

Clause 5: The garment of any preceding clause, wherein the batteries are enclosed in a phase change material, allowing the batteries to remain in the garment during washing and drying of the garment.

Clause 6: The garment of any preceding clause, wherein at least one of the power receivers are induction coils configured to receive power via induction.

Clause 7: The garment of any of clauses 1-5, wherein at least one of the power receivers are electrical contacts configured to receive power via a galvanic connection.

Clause 8: The garment of any preceding clause, wherein the garment is a shirt or jacket and the one or more heating or cooling elements include one or more heating elements in a left sleeve and a right sleeve of the garment, one or more heating elements in one or both of an upper chest and abdomen portion of the garment, and one or more heating elements in one or both of an upper back and lower back portion of the garment, an operation of each of the one or more heating elements being independently controllable by the circuitry.

Clause 9: The garment of any preceding clause, wherein the power receivers receive power from power transmitters in hanger or hook or stand or drawer or power mat, the power receivers generally aligning with the power transmitters or connecting with the power transmitters via a cable.

Clause 10: The garment of any preceding clause, wherein the garment is a shirt or jacket and the one or more power receivers are located in shoulder portions of the garment, the power receivers configured to generally align with one or more power transmitters on a hanger or hook or stand via which power is transmitted to the garment.

Clause 11: The garment of any preceding clause, wherein the circuitry is configured to wirelessly communicate with a remote electronic device, the circuitry configured to control the operation of the one or more heating or cooling elements based at least in part on user provided input on the remote electronic device that the circuitry wirelessly receives from the remote electronic device.

Clause 12: The garment of any preceding clause, further comprising one or more power transmitters configured to transmit power from the garment to one or more additional garment pieces or accessory pieces with active temperature control.

Clause 13: The garment of clause 12, wherein the garment is one of a shirt or jacket, pants and shoes, and wherein the one or more additional garment pieces are the others of a shirt or jacket, pants and shoes, and where accessories are gloves or socks, where each of the shirt or jacket, pants, shoes, gloves and socks have one or more heating or cooling elements operable by the circuitry to heat or cool a surface associated with the one or more heating or cooling elements.

Clause 14: The garment of any preceding clause, further comprising one or more sensors located in one or more portions of the garment and configured to sense one or more parameters chosen from a temperature, a humidity, an oxygen level and a heart rate, the one or more sensors configured to communicate the sensed parameter information to the circuitry, the circuitry configured to control the operation of the one or more heating or cooling elements based at least in part on the sensed parameter information.

Clause 15: A hanger assembly for use with a garment with active temperature control, the hanger comprising:
one or more power receivers;
one or more power transmitters in a body of the hanger; and
circuitry in the body of the hanger, the circuitry configured to communicate with the one or more power transmitters and to control delivery of power from the one or more power transmitters in the hanger to one or more power receivers in the garment with active temperature control when the garment is hung on the hanger.

Clause 16: The hanger assembly of clause 15, wherein the one or more power receivers are one or more electrical contacts in a hook attached to the body of the hanger.

Clause 17: The hanger assembly of clause 15, wherein the one or more power receivers is an electrical cord and electric plug configured to connect to wall power.

Clause 18: The hanger assembly of any of clauses 15-17, wherein the hanger body is disposed on a stand.

Clause 19: The hanger assembly of any of clauses 15-18, wherein the one or more power transmitters are in shoulder portions of the hanger body.

Clause 20: The hanger assembly of any of clauses 15-19, further comprising one or more batteries in communication with one or more of the power receivers, power transmitters and circuitry, the one or more batteries configured to one or both of receive power from the power receivers to charge the batteries and transmit power to the power transmitters to thereby transmit power to a garment with active temperature control hung on the hanger body.

Clause 21: The hanger assembly of any of clauses 15-20, further comprising a closet rod or wall-mounted hook or rod with hooks having a power cord and electrical plug connectable to a wall power outlet to transmit power to one or more electrical connectors or contacts of the closet rod or wall-mounted hook or rod with hooks that receiver at least partially thereon or therein a hook or connector of the hanger body or the garment with active temperature control to thereby transfer power to the hanger or garment.

Clause 22: The hanger assembly of clause 21, wherein the closet rod has one or a circular, square, crescent shaped, and at least partially hollow shape.

While certain embodiments of the inventions have been described, these embodiments have been presented by way of example only, and are not intended to limit the scope of the disclosure. Indeed, the novel methods and systems described herein may be embodied in a variety of other forms. For example, instead of batteries, 40, 440, 540, 640, super capacitors can be used, which can charge faster but allow for less energy storage capacity. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A garment with active temperature control, comprising:
   a plurality of separate heating or cooling elements disposed in different portions of the garment;
   one or more batteries;
   one or more power receivers;
   one or more sensors; and
   circuitry configured to control delivery of power to the heating or cooling elements to heat or cool the different portions of the garment associated with the heating or cooling elements and configured to wirelessly communicate with a remote electronic device, the circuitry configured to independently control operation of each of the heating or cooling elements based at least in part on user provided input on the remote electronic device that the circuitry wirelessly receives from the remote electronic device, wherein at least one of the power receivers are induction coils configured to receive power via induction.

2. The garment of claim 1, wherein the garment is a shirt or jacket.

3. The garment of claim 1, wherein the plurality of heating or cooling elements are woven into a fabric of the garment or disposed between two layers of fabric.

4. The garment of claim 1, wherein the one or more batteries are removable, allowing the garment to be washed without the batteries.

5. The garment of claim 1, wherein the batteries are enclosed in a phase change material, allowing the batteries to remain in the garment during washing and drying of the garment.

6. The garment of claim 1, wherein the one or more power receivers are configured to receive power from corresponding power transmitters of a hanger, a hook, a stand, a drawer or a power mat, the power receivers configured to generally align with the power transmitters or to connect with the power transmitters via a cable.

7. The garment of claim 1, wherein the garment is a shirt or jacket and the one or more power receivers are located in shoulder portions of the garment, the power receivers configured to generally align with one or more power transmitters on a hanger, a hook or a stand via which power is transmitted to the garment.

8. The garment of claim 1, further comprising one or more power transmitters configured to transmit power from the garment to one or more additional garments or one or more accessories.

9. The garment of claim 8, wherein the garment is a shirt, a jacket, a pair of pants or a pair of shoes, and wherein the one or more additional garments is another of the shirt, the jacket, the pair of pants or the pair of shoes, and where the one or more accessories are a pair of gloves or a pair of socks, where each of the shirt, the jacket, the pair of pants, the pair of shoes, the pair of gloves and the pair of socks have one or more heating or cooling elements operable by the circuitry to heat or cool a surface associated with the one or more heating or cooling elements.

10. A garment with active temperature control, comprising:
a plurality of separate heating or cooling elements disposed in different portions of the garment;
one or more batteries;
one or more power receivers;
one or more sensors; and
circuitry configured to control delivery of power to the heating or cooling elements to heat or cool the different portions of the garment associated with the heating or cooling elements and configured to wirelessly communicate with a remote electronic device, the circuitry configured to independently control operation of each of the heating or cooling elements based at least in part on user provided input on the remote electronic device that the circuitry wirelessly receives from the remote electronic device, wherein the one or more sensors are located in one or more portions of the garment and configured to sense one or more parameters chosen from a body temperature, an ambient temperature, a humidity, an oxygen level and a heart rate, the one or more sensors configured to communicate sensed parameter information to the circuitry, the circuitry configured to automatically control the operation of the one or more heating or cooling elements based at least in part on the sensed parameter information.

11. The garment of claim 10, wherein the garment is a shirt or jacket.

12. The garment of claim 11, wherein the one or more power receivers are located in shoulder portions of the garment.

13. The garment of claim 10, wherein the plurality of heating or cooling elements are woven into a fabric of the garment or disposed between two layers of fabric.

14. The garment of claim 10, wherein the one or more power receivers are configured to receive power from corresponding power transmitters of a hanger, a hook, a stand, a drawer or a power mat.

15. The garment of claim 10, wherein the one or more sensors are chosen from a body temperature sensor, an ambient temperature sensor, a humidity sensor, an oxygen level sensor, and a heart rate sensor.

16. A garment with active temperature control, comprising:
a plurality of separate heating or cooling elements disposed in different portions of the garment;
one or more batteries;
one or more power receivers configured to receive power to charge the one or more batteries;
one or more power transmitters;
one or more sensors located in one or more portions of the garment and configured to sense one or more parameters; and
circuitry configured to control delivery of power to the heating or cooling elements to heat or cool the different portions of the garment associated with the heating or cooling elements and configured to wirelessly communicate with a remote electronic device, the one or more sensors configured to communicate sensed parameter information to the circuitry, the circuitry configured to independently and automatically control operation of the plurality of heating or cooling elements based at least in part on the sensed parameter information, wherein the garment is a shirt or jacket, and wherein the one or more power receivers are a plurality of induction power receivers, and wherein the one or more power transmitters are induction power transmitters disposed in one or both sleeves or a waist of the shirt or jacket and configured to transmit power to one or more other garments or one or more accessories coupleable to the garment.

17. The garment of claim 16, wherein the circuitry is configured to wirelessly receive user provided input from the remote electronic device and to control the operation of each of the plurality of heating or cooling elements based at least in part on the user provided input.

18. The garment of claim 16, wherein the one or more sensors are chosen from a body temperature sensor, an ambient temperature sensor, a humidity sensor, an oxygen level sensor, and a heart rate sensor.

19. The garment of claim 16, wherein the plurality of heating or cooling elements are woven into a fabric of the garment or disposed between two layers of fabric.

20. The garment of claim 16, wherein the one or more batteries are removable, allowing the garment to be washed without the batteries.

21. The garment of claim 16, wherein the batteries are enclosed in a phase change material, allowing the batteries to remain in the garment during washing and drying of the garment.

* * * * *